US012595233B2

(12) United States Patent
Al-Abed et al.

(10) Patent No.: US 12,595,233 B2
(45) Date of Patent: Apr. 7, 2026

(54) THIOSEMICARBAZATES AND USES THEREOF

(71) Applicant: THE FEINSTEIN INSTITUTES FOR MEDICAL RESEARCH, Manhasset, NY (US)

(72) Inventors: Yousef Al-Abed, Manhasset, NY (US); Ahmad Altiti, Manhasset, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 932 days.

(21) Appl. No.: 17/831,504

(22) Filed: Jun. 3, 2022

(65) Prior Publication Data

US 2022/0306577 A1 Sep. 29, 2022

Related U.S. Application Data

(62) Division of application No. 16/869,749, filed on May 8, 2020, now Pat. No. 11,440,881.

(60) Provisional application No. 62/845,694, filed on May 9, 2019.

(51) Int. Cl.
*C07D 209/48* (2006.01)
*C07D 403/12* (2006.01)

(52) U.S. Cl.
CPC ......... *C07D 209/48* (2013.01); *C07D 403/12* (2013.01)

(58) Field of Classification Search
CPC ............................ C07D 209/48; C07D 403/12
See application file for complete search history.

(56) References Cited

U.S. PATENT DOCUMENTS

| | | | | |
|---|---|---|---|---|
| 4,282,169 | A | 8/1981 | Rothgery | A01N 47/24 564/150 |
| 4,713,381 | A | 12/1987 | Ao | C07D 471/04 544/182 |
| 5,602,231 | A | 2/1997 | Cotton et al. | |
| 7,531,533 | B2 * | 5/2009 | Shoda | C07D 417/14 544/8 |
| 8,563,565 | B2 | 10/2013 | Norimine et al. | |
| 9,186,371 | B2 | 11/2015 | Taniguchi et al. | |
| 10,919,882 | B2 | 2/2021 | Al-Abed et al. | |
| 11,414,405 | B2 | 8/2022 | Al-Abed et al. | |
| 11,440,881 | B2 | 9/2022 | Al-Abed et al. | |
| 11,471,507 | B2 | 10/2022 | Al-Abed et al. | |
| 11,471,508 | B2 | 10/2022 | Al-Abed et al. | |
| 11,524,048 | B2 | 12/2022 | Al-Abed | |
| 2006/0281686 | A1 | 12/2006 | Lopez Areiza et al. | |
| 2011/0086836 | A1 | 4/2011 | Soeberdt et al. | |
| 2018/0344808 | A1 | 12/2018 | Tracey et al. | |
| 2019/0055283 | A1 | 2/2019 | Ekici et al. | |
| 2020/0354404 | A1 | 11/2020 | Al-Abed | |
| 2020/0354418 | A1 | 11/2020 | Al-Abed | |
| 2021/0188837 | A1 | 6/2021 | Shikanai et al. | |
| 2022/0372022 | A1 | 11/2022 | Al-Abed et al. | |

FOREIGN PATENT DOCUMENTS

| | | | |
|---|---|---|---|
| CN | 101932568 | A | 12/2010 |
| EP | 1 847 533 | A1 | 10/2007 |
| GB | 826300 | | 12/1959 |
| JP | 2001 075232 | A | 3/2001 |
| WO | WO 01/40515 | A1 | 6/2001 |
| WO | WO 2009/096609 | A1 | 8/2009 |
| WO | WO 2016/094899 | A2 | 6/2016 |
| WO | WO 2019/131582 | A1 | 7/2019 |

OTHER PUBLICATIONS

Cécile Abbas et al., "Original and efficient synthesis of 2:1-[α/aza]-oligomer precursors", Tetrahedron Letters, vol. 50, No. 28, pp. 4158-4160, Jul. 15, 2009.
Noam S. Freeman et al., "Microwave-Assisted Solid-Phase Aza-peptide Synthesis: Aza Scan of a PKB/Akr Inhibitor Using Aza-arginine and Aza-proline Precursors", The Journal of Organic Chemistry, vol. 76, No. 9, pp. 3078-3085, May 6, 2011.
Mariappan Anbazhagan et al., "Conversion of Carbonimidodithioates into Unsymmetrical Di- and tri-substituted. Ureas including Urea Dipeptides", Tetrahedron Letters, vol. 39, No. 21, pp. 3609-3612, 1998.
European Search Report issued on Dec. 19, 2022, in corresponding European Application No. EP 20 80 2822.
Nathalie Ollivier et al., "Silver Catalyzed azaGly Ligation. Application to the Synthesis of Azapeptides and of Lipid-Peptide Conjugates", Bioconjugate Chem, vol. 20, pp. 1397-1403, 2009.
Ramesh Chingle et al., "Azapeptide Synthesis Methods for Expanding Side-Chain Diversity for Biomedical Applications", Accounts of Chemical Research, vol. 50, pp. 1541-1556, 2017.
(Continued)

*Primary Examiner* — Kamal A Saeed
(74) *Attorney, Agent, or Firm* — Davidson Kappel LLC

(57) ABSTRACT

Thioesters, thiocarbamates, thiocarbazates, semithiocarbazates, peptides, aza-amino acid conjugates, and azapeptides; and a chemoselective and site-specific functionalization protocol of protected thiocarbazates and semithiocarbazates are described. The protocol features the use of Mitsunobu reaction to alkylate specifically the nitrogen atom close to the acylthiol moiety with alcohols to produce protected mono-substituted thiocarbazates that can be stored for months, activated under mild conditions at low temperature using halonium reagents and integrated orthogonally to make substituted semicarbazides that can be used, e.g., as synthons in synthesis of aza-amino acid conjugates, azapeptides and other peptidomimetics. Methods for preparing and using ureases, carbazides, semicarbazides, beta-peptides, azapeptides, and other peptidomimetics and azapeptide conjugates, and uses of ureases, carbazides, semicarbazides, beta-peptides, azapeptides in drug discovery, diagnosis, inhibition, prevention and treatment of diseases are also described.

21 Claims, 8 Drawing Sheets

(56) References Cited

OTHER PUBLICATIONS

Branka Zorc et al., "Benzotriazole as a Synthetic Auxiliary", Croatica Chemica Acta, 85(4), pp. 959-601, 2012.
Ye Che et al., "Impact of Cis-Proline Analogs Peptide Conformation", Biopolymers, vol. 81, pp. 392-406, 2006.
Harper, H.A. et al. "Review of physiological chemistry" *LANGE Medical Publications*. 16th Ed. pp. 50-51. 1977.
Carine B. Bourguet et al., "Solution-phase submonomer diversification of the aza-dipeptide building blocks and their application in aza-peptide and aza-DKP synthesis", Journal of Peptide Science, vol. 16, No. 6, Jun. 1, 2010, pp. 284-296.
International Search Report issued on Sep. 2, 2020, from corresponding International Application No. PCT/US20/31998.
Written Opinion of the International Searching Authority issued on Sep. 2, 2020, from corresponding International Application No. PCT/US20/31998.
PubChem CID-136595533 "(2,5-Dioxopyrrol-1-yl) N-(2,5-dihydroxypyrrol-1-yl)-N-(1,3-dioxoisoindol-2-yl)carbamate" Created on Jan. 4, 2019.
PubChem CID-132255576 "(2S)-2-(Imidazole-1-carbonylamino)pentanedioic acid" Created on Jan. 29, 2018.
International Search Report issued on Jul. 31, 2020, from corresponding International Application No. PCT/US20/32025.
Written Opinion of the International Searching Authority issued on Jul. 31, 2020, from corresponding International Application No. PCT/US20/32025.
Yang et al. "MD-2 is required for disulfide HMGB1-dependent TLR4 signaling" The Journal of Experimental Medicine; Published on Jan. 5, 2015; vol. 212; p. 5-14.
Sun et al. "Folic acid derived-P5779 mimetics regulate DAMP-mediated inflammation through disruption of HMGB1:TLR4: MD-2 axes" PLOS One; Published on Feb. 15, 2018; vol. 13; p. 1-14.
International Search Report issued on Sep. 10, 2020, from corresponding International Application No. PCT/US20/31992.
Written Opinion of the International Searching Authority issued on Sep. 10, 2020, from corresponding International Application No. PCT/US20/31992.
PubChem CID-519335 "Methanethioic S-acid" Created on Mar. 27, 2005.
Heffeter et al. "Anticancer Thiosemicarbazones: Chemical Properties, Interaction with Iron Metabolism, and Resistance Development" ANTIOXIDANTS & Redox Signaling; vol. 30, No. 8, 2019.
International Search Report issued on Sep. 16, 2020, from corresponding International Application No. PCT/US20/31988.
Written Opinion of the International Searching Authority issued on Sep. 16, 2020, from corresponding International Application No. PCT/US20/31988.
PubChem CID-67548889 "Methyl (2S)-1-(imidazole-1-carbonyl)pyrrolidine-2-carboxylate" Created on Nov. 30, 2012.
PubChem CID-1089188 "(2s)-1-(1-Imidazolylcarbonyl)pyrrolidine-2-carboxylic acid benzyl ester" Created on Oct. 26, 2006.
Riemschneider, R. JACS 1955, 844-847.

* cited by examiner

A7123

A790

| | RT (min) | Area (µV*sec) | % Area | Height (µV) | % Height |
|---|---|---|---|---|---|
| 1 | 4.309 | 38400 | 0.39 | 9163 | 0.37 |
| 2 | 4.789 | 89621 | 0.92 | 37991 | 1.53 |
| 3 | 4.891 | 9482598 | 97.06 | 2386787 | 96.34 |
| 4 | 5.011 | 159576 | 1.63 | 43541 | 1.76 |

| | RT (min) | Area (µV*sec) | % Area | Height (µV) | % Height |
|---|---|---|---|---|---|
| 1 | 4.606 | 218196 | 2.34 | 39578 | 1.99 |
| 2 | 5.072 | 9111469 | 97.66 | 1944765 | 98.01 |

| | RT (min) | Area (µV*sec) | % Area | Height (µV) | % Height |
|---|---|---|---|---|---|
| 1 | 4.339 | 327849 | 3.25 | 115800 | 4.80 |
| 2 | 4.823 | 64789 | 0.64 | 11269 | 0.47 |
| 3 | 4.939 | 79828 | 0.79 | 22626 | 0.94 |
| 4 | 5.066 | 9361219 | 92.67 | 2188564 | 90.81 |
| 5 | 5.212 | 242020 | 2.40 | 63276 | 2.63 |
| 6 | 5.509 | 26367 | 0.26 | 8612 | 0.36 |

| | RT (min) | Area (µV*sec) | % Area | Height (µV) | % Height |
|---|---|---|---|---|---|
| 1 | 4.336 | 41106 | 0.46 | 8532 | 0.36 |
| 2 | 4.738 | 17100 | 0.19 | 2996 | 0.13 |
| 3 | 4.940 | 8813631 | 98.53 | 2373161 | 99.17 |
| 4 | 5.095 | 45460 | 0.51 | 5259 | 0.22 |
| 5 | 5.403 | 28064 | 0.31 | 3092 | 0.13 |

THIOSEMICARBAZATES AND USES THEREOF

This application is a divisional of U.S. patent application Ser. No. 16/869,749, filed May 8, 2020, which claims the benefit of U.S. Provisional Application No. 62/845,694, filed on May 9, 2019, the disclosures of which are hereby incorporated by reference herein.

FIELD OF THE INVENTION

The present invention is directed to compounds for use in synthesis of aza-amino acid conjugates, azapeptides, peptoids, azapeptoids, and other peptidomimetics; processes for preparing ureases, thioesters, thiocarbamates, thiocarbazates, thiosemicarbazides (collectively "acylthiols"), beta-peptides, and azapepeptides; aza-amino acid conjugates, azapeptides, beta-peptides and other peptidomimetics prepared from the acylthiols; and uses of the aza-amino acid conjugates, azapeptides, beta-peptides and other peptidomimetics in drug discovery, diagnosis, prevention, inhibition, and treatment of diseases.

BACKGROUND OF THE INVENTION

The in vitro and in vivo stability and in vitro and in vivo half-lives of peptides are limited, e.g., by their rate of hydrolysis and enzymatic degradation.

Azapeptides are analogs of peptides. An azapeptide contains a substituted semicarbazide instead of one or more of the amino acid residue(s) of the parent peptide. In other words, one or more of α-carbon atom(s) of the parent peptide are replaced with a nitrogen atom in the azapeptide. Due to the reduced reactivity of the carbonyl moiety in the aza-amino acid residue relative to a natural amino acid counterpart, an aza-peptide bond is more stable under the effect of peptidases. Thus, azapeptides are hydrolysed and degraded by peptidases at a slower rate and exhibit, e.g., an improved metabolic stability, than the parent peptides.

The rate of formation of the aza-peptide bond is much slower than that of a typical peptide bond. Consequently, there is a greater potential of formation of unwanted side products during azapeptide synthesis with aza-amino acids than with conventional amino acids. An additional obstacle in utilizing aza-amino acids in syntheses of azapeptides is the orthogonal functionalization of the two available nitrogen atoms in the hydrazine system, peptidomimetics azapeptides with aza-amino acids and conventional coupling agents was challenging prior to the present invention.

There is a need for compounds which overcome the limitations of conventional aza-amino acids and/or allow for a faster, cheaper and more efficient synthesis of azapeptides, aza-amino acid conjugates and other peptidomimetics.

SUMMARY OF THE INVENTION

It is an object of the invention to provide compounds for synthesis of aza-amino acid conjugates, azapeptides and other peptidomimetics.

It is another object of the invention to provide aza-amino acid conjugates, azapeptides and other peptidomimetics that are more stable and more efficacious than their parent peptides.

It is yet an additional object of the invention to provide azapeptide diagnostic and therapeutic agents.

It is also an object of the invention to provide new and efficacious means and processes for the amide bond formation and coupling of amino acids, aza-amino acids, aza-amino acid conjugates, peptides, and aza-peptides.

In connection with the above objects and others, the invention provides thiocarbazates, thiosemicarbazates, thiocarbamates and thioesters (collectively, "acylthiols") and uses of these acylthiols in preparation of various peptides, aza-amino acid conjugates, azapeptides, and other peptidomimetics. These acylthiols are stable entities and, prior to use, can be stored for extended periods of time without being compromised. As compared to the conventional amino acids and aza-amino acids, the acylthiols could be activated under milder conditions and at lower temperatures using halonium reagents (e.g., trichloroisocyanuric acid ("TCCA), or a combination of tetrabutyl ammonium chloride ("TBACl") with tetrabutyl ammonium chloride ("TBACl")). TBACl enhances reaction performance when added prior to TCCA.

These milder conditions and temperatures are compatible with, e.g., the protecting groups that are commonly used in the synthesis of amino acids, aza-amino acids, aza-amino acid conjugates, peptides, azapeptides, and side chains of conventional amino acids. Accordingly, the acylthiols could be efficiently and practically activated and orthogonally integrated into semicarbazides, azapeptides and other peptidomimetics and used to prepare aza-amino acid conjugates, both during solution and solid-phase protein syntheses. Thus, in certain embodiments, acylthiols are used as building blocks or synthons in synthesises of aza-amino acid conjugates, semicarbazides, azapeptides, and other peptidomimetics. The use of the acylthiols allows, e.g., for the synthesis of aza-amino acid conjugates, semicarbazides, azapeptides, and other peptidomimetics at greater yields and/or faster times and/or higher purity, as compared to syntheses of these compounds from natural amino acids and aza-amino acids.

The invention also provides a chemoselective and site-specific functionalization protocol for protected thiocarbazates and semithiocarbazates. The protocol features the use of Mitsunobu reaction to alkylate specifically the nitrogen atom close to the acylthiol moiety with alcohols to produce protected mono-substituted thiocarbazates that are stable and can be stored for prolonged periods of times (e.g., months) without being compromised. These protected mono-substituted thiocarbazates can be practically activated under mild conditions using halonium reagents (e.g., TCCA or a mixture of TCCA and TBACl) at low temperatures, and integrated orthogonally to make substituted semicarbazides. The substituted semicarbazides can then be used as building blocks or synthons in the preparation of aza-amino acid conjugates, azapeptides and other peptidomimetics. The protocol is compatible with the side chains of commonly used amino acids and protecting groups used in peptide syntheses and, consequently, is suitable for the synthesis of substituted chiral urease and the chiral beta-amino peptides from the corresponding thiocarbamates and thioester respectively, e.g., without epimerization, both in solution phase and solid-phase protein synthesis.

The invention further provides semicarbazides, azapeptides, azapeptide conjugates, aza-amino acid conjugates and other peptidomimetics prepared from the acylthiols and/or by the chemoselective and site-specific functionalization protocol.

Thus, in one aspect, the invention provides unsubstituted and substituted S-alkylthiocarbazates that can be used in synthesis of aza-amino acid conjugates, substituted and unsubstituted semicarbazides, azapeptides and other peptidomimetics.

The invention further provides substituted and unsubstituted semicarbazides and semithiocarbazides that can be used in synthesis of aza-amino acid conjugates, azapeptides and other peptidomimetics.

In one aspect, the invention is directed to compounds of Formula (I):

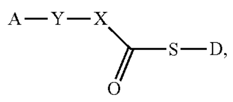
(I)

wherein A is selected from the group consisting of H, substituted or unsubstituted branched and unbranched alkyls, substituted or unsubstituted aryls, substituted or unsubstituted heteroaryls, peptides, azapeptides, phthaloyl (Phth), N-phthalimidyl, tert-butoxycarbonyl (Boc), 9-fluorenylmethoxycarbonyl (Fmoc), carboxybenzyl (Cbz), 2-(3,5-dimethoxyphenyl)propan-2-yloxycarbonyl (Ddz), 2,2,4,6,7-pentamethyl-dihydrobenzofuran-5-sulfonyl (Pbf), trityl or triphenylmethyl (Trt), t-butyl ester (OtBu), t-butyl ether (tBu), allyloxycarbonyl (Aloc), methoxytrimethylbenzene sulfonyl (Mtr), 4,4-dimethyloxybenzhydryl (Mbh), 2,2,5,7,8-pentamethyl-chroman-6-sulfonyl chloride (Pmc), 2,4,6-trimethoxybenzyl (Tmob), allyl ester (OAl), and acetamidomethyl (Acm);

Y is selected from the group consisting of a bond, $NR_1$, $CHR_2$, $CHR_3CONR_4$, and side chain radicals of amino acids;

X is selected from the group consisting of a bond, $NR_5$ or $CH_2$;

D is an H, Cl, alkyl, an aryl or heteroaryl, $R_1$, $R_2$, $R_3$, $R_4$, and $R_5$, is each independently selected from the group consisting of a bond, H, alkyls, alkoxyls, alkyl ether, or a protected alkyl amine. The alkyl, the aryl and heteroaryl may each be substituted or unsubstituted. In some embodiments, alkyl is selected from the group consisting of side chain radicals of amino acids (e.g., aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine. The alkyl, aryl, heteroaryl and side chain radical may each independently be substituted with one or more of the following: a halogen (Cl, F), a $C_1$-$C_6$ alkyl (e.g., methyl), —COOR, —COR, methoxyl, ethoxyl, propoxyl, a $C_1$-$C_6$ haloalkyl (e.g., a chloromethyl, a fluromethyl, etc.) or a protecting group (e.g., N-phthalimidyl, tert-butoxycarbonyl, 9-fluorenylmethoxycarbonyl, 2-(3,5-dimethoxyphenyl)propan-2-yloxycarbonyl, etc.), wherein R is selected from the group consisting of alkyls, alkoxyls, alkyl ethers, and protected alkyl amines.

The invention is also directed to compounds of Formula (II):

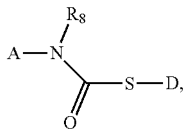
(II)

wherein A is N-phthalimidyl;

D is H, Cl, an alkyl, an aryl or heteroaryl;

$R_8$ is H or a side chain radical of an amino acid. The alkyl, the aryl and heteroaryl may each independently be substituted or unsubstituted with one or more of the following: a halogen (Cl, F), a $C_1$-$C_6$ alkyl (e.g., methyl), —COOR, —COR, methoxyl, ethoxyl, propoxyl, a $C_1$-$C_6$ haloalkyl (e.g., a chloromethyl, a fluromethyl, etc.) or a protecting group (e.g., N-phthalimidyl, tert-butoxycarbonyl, 9-fluorenylmethoxycarbonyl, 2-(3,5-dimethoxyphenyl)propan-2-yloxycarbonyl etc.), wherein R is selected from the group consisting of alkyls, alkoxyls, alkyl ethers, and protected alkyl amines.

The invention is further directed to compounds of Formula (IIIA):

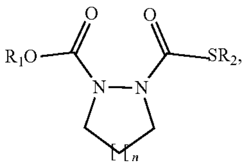
(IIIA)

wherein $R_1$ and $R_2$ is each independently selected from the group consisting of H, halogens, OH, $NR_3R_4$, alkyls, aryls, and heteroaryls;

$R_3$ and $R_4$ is each independently selected from the group consisting of a bond, H, alkyls, alkoxyls, alkyl ether, or a protected alkyl amine; and n is 1, 2, 3, or 4. $R_1$, $R_2$, $R_3$ and $R_4$ may each independently be unsubstituted or substituted with one or more of the following: a halogen (Cl, F), a $C_1$-$C_6$ alkyl (e.g., methyl), —COOR, —COR, methoxyl, ethoxyl, propoxyl, a $C_1$-$C_6$ haloalkyl (e.g., a chloromethyl, a fluromethyl, etc.) or a protecting group (e.g., N-phthalimidyl, tert-butoxycarbonyl, 9-fluorenylmethoxycarbonyl, 2-(3,5-dimethoxyphenyl)propan-2-yloxycarbonyl, etc.).

The invention is further directed to compounds of Formula (IIIB):

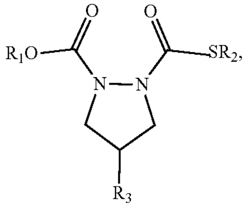
(IIIB)

wherein $R_1$ and $R_2$ is each independently selected from a group consisting of H, halogens, OH, $NR_3R_4$, alkyls, aryls, and heteroaryls; $R_3$ and $R_4$ is each independently selected from the group consisting of a bond, H, alkyls, alkoxyls, alkyl ether, or a protected alkyl amine;

Ri is selected from a group consisting of halogens (e.g., Cl, F), a $C_1$-$C_6$ alkyl (e.g., methyl), —COOR, —COR, methoxyl, ethoxyl, propoxyl, a $C_1$-$C_6$ haloalkyl (e.g., a chloromethyl, a fluromethyl, etc.) or a protecting group (e.g., N-phthalimidyl, tert-butoxycarbonyl, 9-fluorenylmethoxycarbonyl, 2-(3,5-dimethoxyphenyl)propan-2-yloxycarbonyl, etc.);

R is selected from the group consisting of alkyls, alkoxyls, alkyl ethers, and protected alkyl amines;

and n is 1, 2, 3, or 4. $R_1$, $R_2$, $R_3$ and $R_4$ may each be unsubstituted or independently substituted with one or more of the following: a halogen (Cl, F), a $C_1$-$C_6$ alkyl (e.g., methyl), —COOR, —COR, methoxyl, ethoxyl, propoxyl, a $C_1$-$C_6$ haloalkyl (e.g., a chloromethyl, a fluromethyl, etc.) or a protecting group (e.g., N-phthalimidyl, tert-butoxycarbonyl, 9-fluorenylmethoxycarbonyl, 2-(3,5-dimethoxyphenyl)propan-2-yloxycarbonyl, etc.).

The invention is further directed to compounds of Formula (III):

(III)

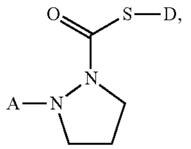

wherein A is a carbamate based protecting group selected from the group consisting of tert-butoxycarbonyl, 9-fluorenylmethoxycarbonyl, carboxybenzyl; and D is H, Cl, an alkyl, an aryl or heteroaryl.

In an additional aspect, the invention is directed to compounds of Formula (IV):

(IV)

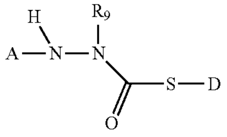

wherein A is selected from the group consisting of tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

D is H, Cl, an unsubstituted or substituted alkyl, an unsubstituted or substituted aryl or an unsubstituted or substituted heteroaryl;

$R_9$ is H, alkyl, alkoxyl, alkyl ether, or a protected alkyl amine. In certain embodiments, $R_9$ is an alkyl selected from the group consisting of side chain radicals of amino acids (e.g., aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine. The alkyl, aryl, heteroaryl, and side chain radicals may independently be unsubstituted or substituted with one or more of the following: a halogen (Cl, F), a $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group, e.g., (e.g., N-phthalimidyl, tert-butoxycarbonyl, 9-fluorenylmethoxycarbonyl, 2-(3,5-dimethoxyphenyl)propan-2-yloxycarbonyl etc.).

The invention is also directed to compounds of Formula (V):

(V)

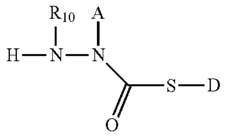

wherein A is selected from the group consisting of tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

D is H, Cl, an unsubstituted or substituted alkyl, an unsubstituted or substituted aryl or an unsubstituted or substituted heteroaryl;

$R_{10}$ is H, alkyl, alkoxyl, alkyl ether, or a protected alkyl amine. In certain embodiments, $R_{10}$ is an alkyl selected from the group consisting of side chain radicals of amino acids (e.g., aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine. The alkyl, aryl, heteroaryl may independently be unsubstituted or substituted with one or more of the following: a halogen (Cl, F), a $C_1$-$C_6$ alkyl (e.g., methyl), —COOR, methoxyl, ethoxyl, propoxyl, a $C_1$-$C_6$ haloalkyl (e.g., —$CF_3$, $CHF_2$, $CH_2F$, —$CCl_3$, —$CHCl_2$, —$CH_2Cl$)) or a protecting group (e.g., N-phthalimidyl, tert-butoxycarbonyl, 9-fluorenylmethoxycarbonyl, 2-(3,5-dimethoxyphenyl)propan-2-yloxycarbonyl, etc.), wherein R is selected from the group consisting of alkyls, alkoxyls, alkyl ethers, and protected alkyl amines.

The invention is further directed to compounds of Formula (VI):

(VI)

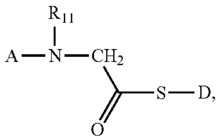

wherein A is selected from the group consisting of N-phthalimidyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

D is H, Cl, an unsubstituted or substituted alkyl, an unsubstituted or substituted aryl, or an unsubstituted or substituted heteroaryl; and $R_{11}$ is H, alkyl, aryl, heteroaryl, lipid, peptide, or a side chain radical of an amino acid.

The invention is also directed to compounds of Formula (VII):

(VII)

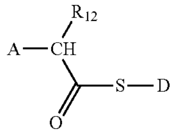

wherein A is selected from the group consisting of peptides, azapeptides, N-phthalimidyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

D is H, Cl, an unsubstituted or substituted alkyl, an unsubstituted or substituted aryl or an unsubstituted or substituted heteroaryl; and $R_{12}$ is H, alkyl, aryl, heteroaryl, lipid, or a side chain radical of an amino acid.

The invention is also directed to compounds of Formula (VIII):

(VIII)

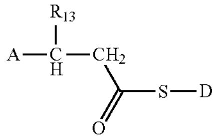

wherein A is selected from the group consisting of peptides, azapeptides, phthalimidyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

D is H, Cl, an unsubstituted or substituted alkyl, unsubstituted or substituted aryl, or an unsubstituted or substituted heteroaryl; and $R_{13}$ is H or a side chain radical of an amino acid.

The invention is also directed to compounds of Formula (IX):

(IX)

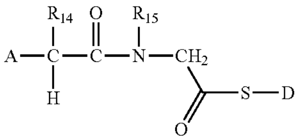

wherein A is selected from the group consisting of peptides, azapeptides, N-phthalimidyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

D is H, Cl, an unsubstituted or substituted alkyl, an unsubstituted or substituted aryl, or an unsubstituted or substituted heteroaryl; and $R_{14}$ and $R_{15}$ is each independently selected from the group consisting of a bond, H, alkyls, alkoxyls, and side chain radicals of amino acids.

The invention is also directed to compounds of Formula (X):

(X)

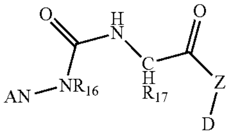

wherein A is phthaloyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

Z is O or S;

$R_{16}$ and $R_{17}$ is each independently a bond, H, an alkyl, alkoxyls, or a side chain radicals of an amino acid; and D is H or an unsubstituted or substituted alkyl, an unsubstituted or substituted aryl, an unsubstituted or substituted heteroaryl, phthalimidyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, or acetamidomethyl. In certain embodiments, Z-D is replaced with a moiety selected from the group consisting of $—NH_2$, $—NHR_1$, or $—NR_2R_3$, wherein $R_1$, $R_2$ and $R_3$ is each independently selected from the group consisting of alkyls, alkoxyls, alkyl ether, or protected alkyl amines.

The invention is also directed to compounds of Formula (XI):

(XI)

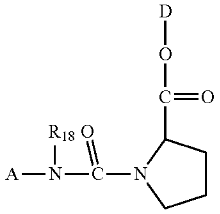

wherein A is phthaloyl, phthalimidyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

$R_{18}$ is a bond, H, an alkyl, an alkoxyl, an alkylalkoxyl, or a side chain radicals of an amino acid; and D is H or an unsubstituted or substituted alkyl, an unsubstituted or substituted aryl, or an unsubstituted or substituted heteroaryl. In certain embodiments, OB is $-NH_2$, $-NHR_1$, or $-NR_2R_3$, wherein $R_1$, $R_2$ and $R_3$ is each independently selected from the group consisting of alkyls, alkoxyls, alkyl ether, or protected alkyl amines.

In addition, the invention is also directed to compounds of Formula (XII):

(XII)

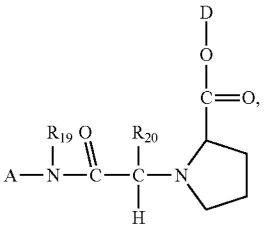

wherein A is N-phthalimidyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

$R_{19}$ and $R_{20}$ is each independently a bond, H, an alkyl, an alkoxyl, an alkylalkoxyl, an alkylaryloxyl, or a side chain radicals of an amino acid; and D is H or an unsubstituted or substituted alkyl, an unsubstituted or substituted aryl, or an unsubstituted or substituted heteroaryl. In certain embodiments, OB is $-NH_2$, $-NHR_1$, or $-NR_2R_3$, wherein $R_1$, $R_2$ and $R_3$ is each independently selected from the group consisting of alkyls, alkoxyls, alkyl ether, or protected alkyl amines.

The invention is further directed to compounds of Formula (XIII):

(XIII)

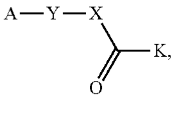

wherein A is selected from the group consisting of peptides, azapeptides, phthaloyl, tert-butoxycarbonyl, 9-fluorenylmethoxycarbonyl, carboxybenzyl, 2-(3,5-dimethoxyphenyl)propan-2-yloxycarbonyl, 2,2,4,6,7-pentamethyl-dihydrobenzofuran-5-sulfonyl, trityl or triphenylmethyl, t-butyl ester, t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, and acetamidomethyl;

Y is selected from the group consisting of a bond, $-NR_{16}$, $-CHR_{17}$, and side chain radicals of amino acids;

X is selected from the group consisting of a bond, $-NR_{18}$ and $-CHR_{19}$;

K is a halogen; and $R_{15}$, $R_{16}$, $R_{17}$ and $R_{18}$ is each independently selected from the group consisting of a bond, H, alkyls, alkoxyls, and side chain radicals of amino acids.

The invention is also directed to compounds of Formula (XIV):

(XIV)

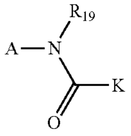

wherein A is phthalimidyl;

K is a halogen (e.g., chloride); and $R_{19}$ is H or a side chain radical of an amino acid.

The invention is further directed to compounds of Formula (XV):

(XV)

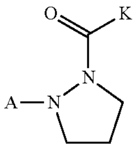

wherein A is selected from the group consisting of, tert-butoxycarbonyl, 9-fluorenylmethoxycarbonyl, carboxybenzyl, and 2-(3,5-dimethoxyphenyl)propan-2-yloxycarbonyl; and K is a halogen (e.g., chloride).

In certain embodiments, A of compounds of Formulas (I)-(XV) is selected from the group consisting of, tert-butoxycarbonyl, 9-fluorenylmethoxycarbonyl, carboxybenzyl.

In some embodiments, B of compounds of Formulas (I) to (X) is an unsubstituted or substituted alkyl, an unsubstituted or substituted aryl, or an unsubstituted or substituted heteroaryl. In some embodiments, B is of compounds of Formulas (I) to (X) is an unsubstituted or substituted alkyl. In some embodiments, the unsubstituted or substituted alkyl is a branched or unbranched $C_2$-$C_{26}$ alkyl.

In certain embodiments, the alkyl of compounds of Formulas (I)-(XV) is a $C_1$-$C_9$ alkyl. In some of these embodiments, the alkyl is selected from the group consisting of methyl, ethyl, propyl, isopropyl, and tert-butyl. In some of these embodiments, the alkyl is ethyl.

$R_1$ to $R_{18}$ of compounds of Formulas (I)-(XV) could each be independently selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, and glutamine.

In certain embodiments, B of compounds of Formula (I)-(XII), is selected from an alkyl, phthalimidyl, tert-butoxycarbonyl, 9-fluorenylmethoxycarbonyl, and carboxybenzyl. In some of these embodiments, B is phthalimidyl (Phth).
In certain embodiments, compounds of Formula (I or II) are selected from the group consisting of:
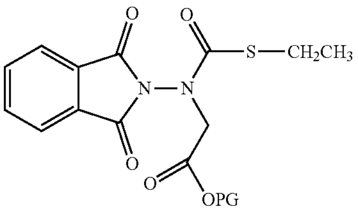
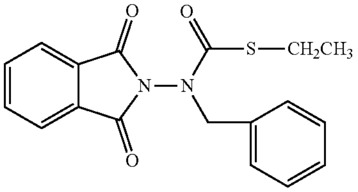
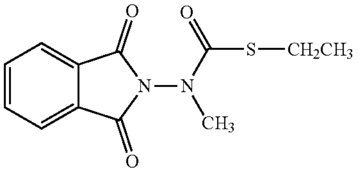
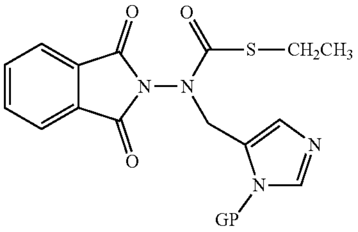
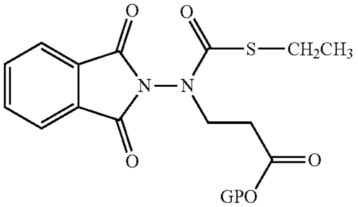
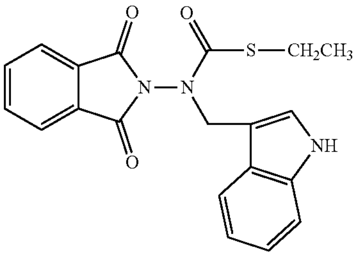
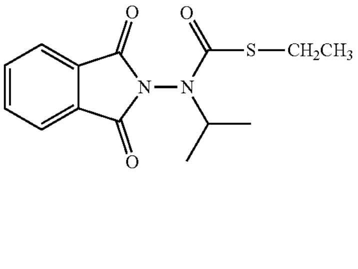
-continued
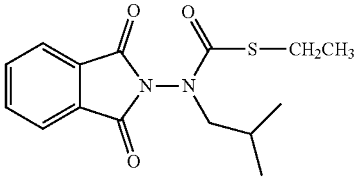
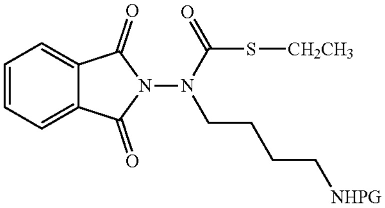
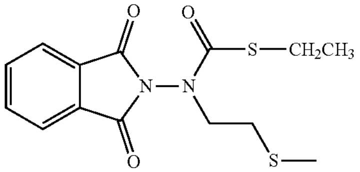
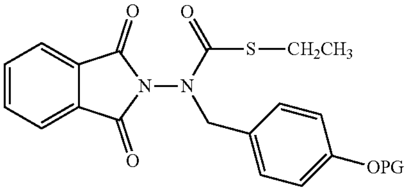
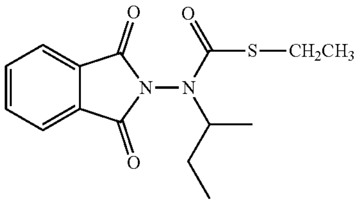
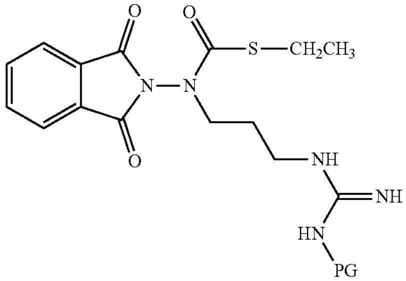
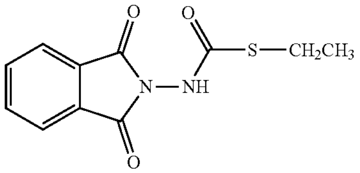
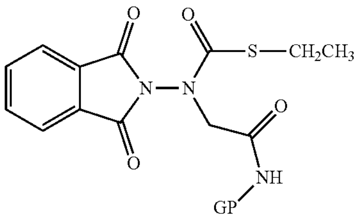

-continued

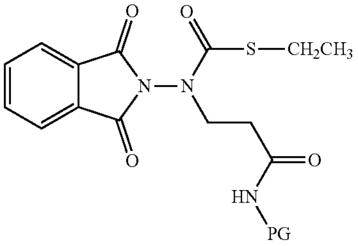

and pharmaceutically acceptable salts thereof, wherein "PG" is H or a protecting group. The protecting group could, e.g., be N-phthalimidyl, tert-butoxycarbonyl, 9-fluorenylmethoxycarbonyl, or 2-(3,5-dimethoxyphenyl)propan-2-yloxycarbonyl.

In certain embodiments, compounds of Formula (I or II) are selected from the group consisting of tert-butyl N-(1,3-dioxoisoindolin-2-yl)-N-((ethylthio)carbonyl)glycinate (N-Phthaloyl Aza-t-butyl aspartate S-ethyl ester), S-ethyl benzyl(1,3-dioxoisoindolin-2-yl)carbamothioate (N-Phthaloyl Aza-phenylalanine S-ethyl ester), S-ethyl (1,3-dioxoisoindolin-2-yl)(methyl)carbamothioate (N-Phthaloyl Aza-alanine S-ethyl ester), S-ethyl ((1H-imidazol-5-yl)methyl)(1,3-dioxoisoindolin-2-yl)carbamothioate or (N-Phthaloyl Aza-histidine S-ethyl ester), dioxoisoindolin-2-yl)((ethylthio)carbonyl)amino)propanoate or (N-Phthaloyl Aza-(t-butyl Glutamate)S-ethyl ester), S-ethyl ((1H-indol-3-yl)methyl)(1,3-dioxoisoindolin-2-yl)carbamothioate (N-Phthaloyl Aza-tryptophan S-ethyl ester), S-ethyl (1,3-dioxoisoindolin-2-yl)(isopropyl)carbamothioate (N-Phthalyol Aza-Valine S-ethyl ester), S-ethyl (1,3-dioxoisoindolin-2-yl)(isobutyl)carbamothioate (N-phthaloyl Aza-Leucine S-ethyl ester), S-ethyl (4-aminobutyl)(1,3-dioxoisoindolin-2-yl)carbamothioate (N-Phthalyol Aza-lysine S-Ethyl ester), S-ethyl (1,3-dioxoisoindolin-2-yl)(2-(methylthio)ethyl)carbamothioate (N-Phthalyol Aza-Methionine S-ethyl ester), S-ethyl (1,3-dioxoisoindolin-2-yl)(4-hydroxybenzyl)carbamothioate (N-Phthalyol Aza-tyrosine S-ethyl ester), S-ethyl sec-butyl(1,3-dioxoisoindolin-2-yl)carbamothioate (N-Phthalyol Aza-isoleucine S-ethyl ester), S-ethyl (1,3-dioxoisoindolin-2-yl)(3-guanidinopropyl)carbamothioate (N-Phthalyol Aza-arginine S-ethyl ester), S-ethyl (1,3-dioxoisoindolin-2-yl) carbamothioate (N-Phthalyol Aza-Glycine S-ethyl ester), S-ethyl (2-amino-2-oxoethyl)(1,3-dioxoisoindolin-2-yl)carbamothioate (N-Phthalyol Aza-aspargine S-ethyl ester), and pharmaceutically acceptable salts thereof.

In certain embodiments, compounds of Formula (IV) are selected from the group consisting of:

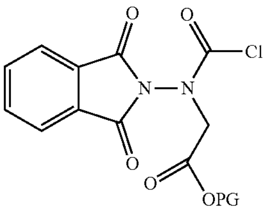

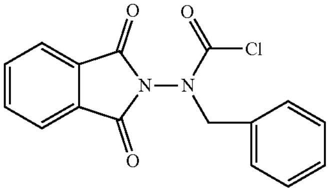

-continued

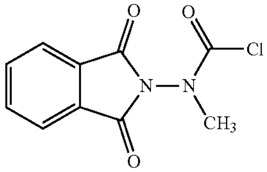

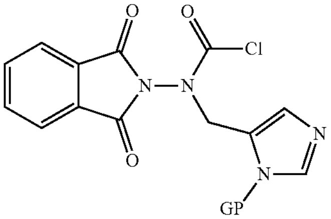

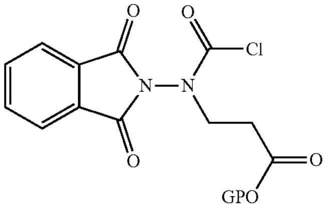

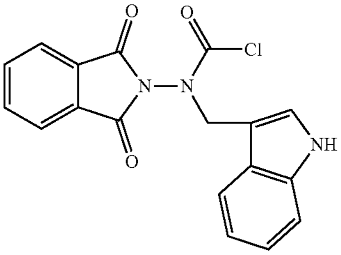

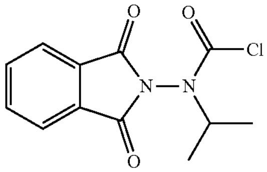

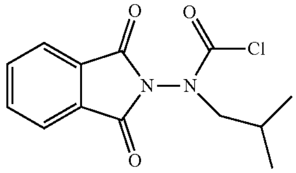

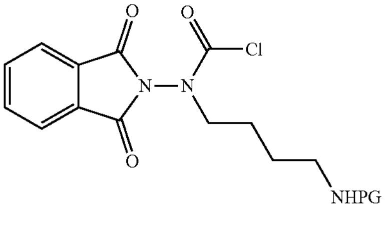

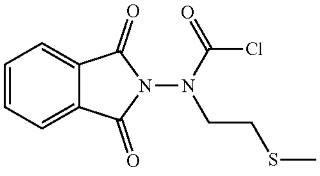

-continued

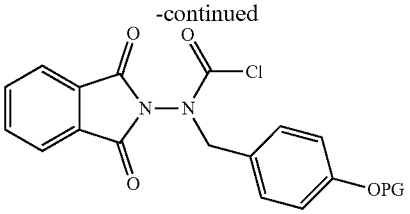

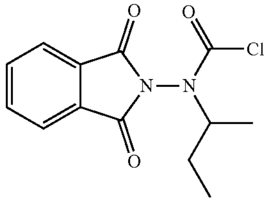

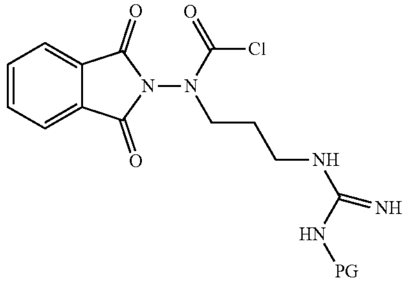

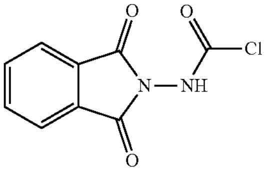

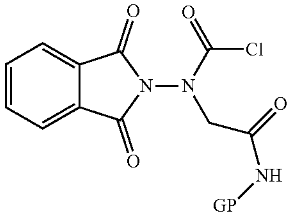

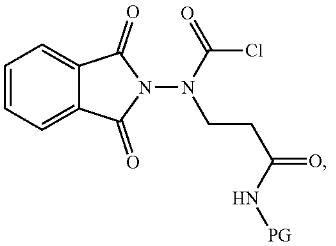

wherein "PG" is H or a protecting group. The protecting group could, e.g., be N-phthalimidyl, tert-butoxycarbonyl, 9-fluorenylmethoxycarbonyl, or 2-(3,5-dimethoxyphenyl) propan-2-yloxycarbonyl.

In certain embodiments, compounds of Formula (IV) are selected from the group consisting of N-Phthalyol-aza-aspartic acyl chloride, N-Phthalyol-aza-phenylalanine acyl chloride, N-Phthalyol-aza-alanine acyl chloride, N-Phthalyol-aza-histidine acyl chloride, N-Phthalyol-aza-glutamic acyl chloride, N-Phthalyol-aza-tryptophan acyl chloride, N-Phthalyol-aza-valine acyl chloride, N-Phthalyol-aza-leucine acyl chloride, N-Phthalyol-aza-lysine acyl chloride, N-Phthalyol-aza-cysteine acyl chloride, N-Phthalyol-aza-tyrosine acyl chloride, N-Phthalyol-aza-leucine acyl chloride, N-Phthalyol-aza-arginine acyl chloride, N-Phthalyol-aza-glycine acyl chloride, N-Phthalyol-aza-asparagine acyl chloride, and N-Phthalyol-aza-glytamine acyl chloride.

The invention also provides a process for preparing compounds according to any one of Formulas (I)-(XII), the process comprising reacting a semi-protected hydrazine with a chlorothioformate to form a protected alkylthio carbonyl hydrazine (an unsubstituted S-thiocarbazate), and alkylating the protected alkylthio carbonyl hydrazine (the unsubstituted S-thiocarbazate) via Mitsunobu reaction, or direct alkylation with NaH or an alkyl halide to form compounds of Formulas (I)-(XII) (substituted S-thiocarbazates). The semi-protected hydrazine may be selected, e.g., from the group consisting of phthalimidyl-hydrazine, tert-butoxycarbonyl-hydrazine, 9-fluorenylmethoxycarbonyl-hydrazine, carboxybenzyl-hydrazine, 2-(3,5-dimethoxyphenyl)propan-2-yloxycarbonyl-hydrazine, 2,2,4,6,7-pentamethyl-dihydrobenzofuran-5-sulfonyl-hydrazine, trityl or triphenylmethyl (Trt)-hydrazine, t-butyl ester-hydrazine, t-butyl ether-hydrazine, StBu-hydrazine, allyloxycarbonyl-hydrazine, methoxytrimethylbenzene sulfonyl-hydrazine, 4,4-dimethyloxybenzhydryl (Mbh)-hydrazine, 2,2,5,7,8-pentamethyl-chroman-6-sulfonyl chloride-hydrazine, 2,4,6-trimethoxybenzyl-hydrazine, allyl ester-hydrazine, and acetamidomethyl-hydrazine. The chlorothioformate may be, e.g., an alkylchlorothioformate (e.g., ethylchlorothioformate). In some embodiments, the process further comprises a step of isolating the compound of Formula (I)-(XII).

The invention further provides a process for selectively alkylating the nitrogen atom closest to the acylthiol moiety of an unsubstituted alkylthio carbonyl hydrazine (ATCH) (an unsubstituted S-alkylthiocarbazate) of Formulas (I) to (XII), the process comprising reacting the unsubstituted alkylthio carbonyl hydrazine (ATCH) (unsubstituted S-alkylthiocarbazates) of Formulas (I) to (XII) with an alcohol to form a protected mono-substituted thiocarbazate. The reaction may, e.g., be a Mitsunobu reaction. The protected mono-substituted S-thiocarbazates may then be activated with a halonium reagent(s) (e.g., TCCA or a mixture of TCCA and TBACl) and coupled with an amine to form a semicarbazide, an azapeptide or an aza-peptide conjugate. In certain embodiments, TCCA can be substituted with N-chlorosuccinamide (NCS), Dichloroisocyanuric acid (DCCA), sodium dichlorocyanuric acid, any N-chloroamide, calcium hypochlorite, or any N-chloroamide.

The NH moiety in amides or carbamates may react with halonium reagents, and, in certain embodiments, addition of TBACl is used to scavenge the excess of the halonium ions and help to tune the reactivity to be selectively and specifically toward the acylthiol part without interference with the NH amide or NH carbamates. See *Synlett*, (2), 223-226; 2005, *Heterocycles,* 76(2), 1511-1524; 2008, Synthesis, (11), 1171-4; 1994.

The use of TBACl is particularly useful when Boc, Cbz and Fmoc protecting groups, guanidine, aminoguanidine moieties, or other similar moieties, are present.

The invention further provides processes that are suitable, e.g., for the synthesis of substituted chiral urease and the chiral beta-amino peptides from the corresponding thiocarbamates and thioesters respectively, without epimerization. The process comprises activation of a compound of Formulas (I)-(XII) with TCCA or TCCA+TBACl and coupling the activated acylthiol with an amine. The acylthiol could be, e.g., a compound according to any one of Formulas (I) to (XII), and amine could be, e.g., an amino ester, an ester of an amino acid, an amino ester of an aza-amino acid, a peptide, or an aza-peptide.

A process for preparing a substituted semicarbazide may comprise the steps of activating a compound according to any one of Formulas (I) to (XII) with TCCA and TBCl to form a compound according to any one of Formulas (XIII) to (XV), and coupling the compound according to any one of Formulas (XIII) to (XV) with an amine. The amine could be selected from the group consisting of amino esters, esters of amino acids, amino esters of aza-amino acids, peptides, and aza-peptides. The reaction may be performed, e.g., in chloroform, dichloromethane, or acetone. In some embodiments, from about 0.5 to about 2 equivalents of TCCA and TBCl are used. In some embodiments, from about 1 to about 3 equivalents of the amine are used. In some embodiments, from about 1.1 to about 1.8 equivalents of TCCA and TBCl, and from about 1.0 to about 1.5 equivalents of the amine are used. The coupling may, e.g., be for a time period of from 15 minutes to 12 hours. In certain embodiments, the coupling may be completed in about 30 minutes, about 40 minutes, about 50 minutes, about 60 minutes, about 70 minutes, about 80 minutes, about 90 minutes, about 100 minutes, about 110 minutes, or about 120 minutes. In certain embodiments, acetonitrile is used as a solvent both during the activating and coupling steps. In certain embodiments, demethylformamide is used as a solvent during the coupling step.

In an additional aspect, the invention is directed to a process for synthesizing azapeptides comprising activating a thioester with TCCA and TBCl to form a reactive acyl chloride, and coupling the reactive acyl chloride with an amine, wherein the thioester is a compound according to any one of Formulas (I)-(XII), the reactive amine chloride is a compound according to any one of Formulas (XIII)-(XV), and), and the amine is selected from the group consisting of amino esters, esters of amino acids, amino esters of aza-amino acids, peptides, and aza-peptides. In some of these embodiments the amine is a peptide or an aza-peptide.

The invention is also directed to a process for a systematic insertion of an aza-amino acid or an aza-amino acid segment(s) at a desired position(s) along the peptide sequence comprising activating a thioester with TCCA and TBCl to form in situ a reactive acyl chloride, and coupling the reactive chloride with an amine, wherein the thioester is a compound according to any one of Formulas (I)-(XII), and the reactive amine chloride is a compound according to any one of Formulas (XIII)-(XV). The amine could be selected, e.g., from the group consisting of amino esters, esters of amino acids, amino esters of aza-amino acids, peptides, and aza-peptides.

The invention is further directed to synthesis of a compound of Formula (XVI):

(XVI)

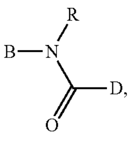

wherein

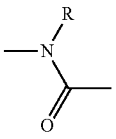

is at the N-terminus and/or the C-terminus and/or at or adjacent to a cleavage and/or a hydrolysis site of the compound of Formula (XVI);

B is selected from the group consisting of hydrogen, —$NH_2$, —$CONH_2$, —$COOR_{19}$, —COOH, —COH, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-merazatide;

D is selected from the group consisting of —$OR_{20}$, —OH, —$NH_2$, —$NNH_2$, —$NHCOCH_3$, —$NHCH_3$, —$N(CH_3)_2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-merazatide;

$R_{19}$ and $R_{20}$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a flurometh yl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine;

the process comprising activating a compound according to any one of Formulas (I)-(XII) to form a reactive chloride, and coupling the reactive chloride with an amine. The reactive chloride may, e.g., be a compound according to any one of Formulas XIII-XV, and the amine may, e.g., be an amino ester, an ester of an amino acid, an amino ester of an aza-amino acid, a peptide, or an aza-peptide. In certain embodiments, the process is conducted during solid phase synthesis of an azapeptide. In some of these embodiments, R of compound of Formula (XVI) is selected from the group consisting of side chain radicals of aspartic acid, phenylalanine, alanine, histidine, glutamic acid, tryptophan, valine, leucine, lysine, methionine, tyrosine, R-isoleucine, S-isoleucine, and RS-isoleucine, arginine, glycine, asparagine, serine, threonine, cysteine and glutamine. The side chain radical may be unsubstituted or substituted with one or more of the following groups: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a flurometh yl, etc.) or a protecting group (e.g., Phth, Boc, Fmoc, Ddz, etc.). In some embodiments, B is selected from the group consisting of hydrogen, —$NH_2$, —$NNH_2$, —$CONH_2$, —$COOR_{19}$, —$COC_1$-$C_4$ alkyl, —$COC_1$-$C_4$ haloalkyl, —OH, an amino acid, an aza amino acid, a 2 to 60-mer peptide, a 2 to 60-mer aza peptide, a 2 to 60-merazatide; D is selected from the group consisting of —$OR_{20}$, —$NH_2$, —$NNH_2$, —$NHCOCH_3$, —$NHCH_3$, —$N(CH_3)_2$, —$CONH_2$, —COOH, —COH, —$COC_1$-$C_4$ alkyl, —$COC_1$-$C_4$ haloalkyl, an amino acid, an aza amino acid, a 2 to 60-mer peptide, a 2 to 60-mer aza peptide, a 2 to 60-merazatide; and $R_{19}$ and $R_{20}$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a flurometh yl, etc.) or a protecting group (e.g., Phth, Boc, Fmoc, Ddz, etc.); and R is selected from the group consisting of side chain radicals of aspartic acid, phenylalanine, alanine, histidine, glutamic acid, tryptophan, valine, leucine, lysine, serine, threonine, methionine, tyrosine, isoleucine (including, R-isoleucine, S-isoleucine and RS-isoleucine), arginine, glycine, asparagine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz). Compounds of Formula (XVI) may be used in drug discovery, diagnosis, prevention, inhibition, and treatment of diseases. In some embodiment, the process further comprises deprotecting the compound of Formula (XVI) with, e.g., hydrazine, piperadine, TFA, acetic acid, thioanisole, EDT, anisole, etc.

The invention is further directed to synthesis of a compound of Formula (XVI):

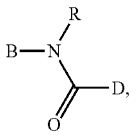

(XVI)

wherein

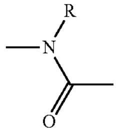

is adjacent to the N-terminus and/or the C-terminus of the compound of Formula (XVI);

B is selected from the group consisting of hydrogen, $—NH_2$, $—CONH_2$, $—COOR_{19}$, —COOH, —COH, $—COC_1$-$C_4$ alkyl, $—COC_1$-$C_4$ haloalkyl, —OH, an amino acid, an aza amino acid, a 2 to 60-mer peptide, a 2 to 60-mer aza peptide, a 2 to 60-merazatide;

D is selected from the group consisting of $—OR_{20}$, —OH, $—NH_2$, $—NNH_2$, $—NHCOCH_3$, $—NHCH_3$, $—N(CH_3)_2$, $—CONH_2$, —COOH, —COH, $—COC_1$-$C_4$ alkyl, $—COC_1$-$C_4$ haloalkyl, an amino acid, an aza amino acid, a 2 to 60-mer peptide, a 2 to 60-mer aza peptide, a 2 to 60-merazatide;

$R_{19}$ and $R_{20}$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine;

the process comprising activating a compound according to any one of Formulas (I)-(XII) to form a reactive chloride, and coupling the reactive chloride with an amine. The reactive chloride may, e.g., be a compound according to any one of Formulas XIII-XV, and the amine may, e.g., be an amino ester, an ester of an amino acid, an amino ester of an aza-amino acid, a peptide, or an aza-peptide. In certain embodiments, the process is conducted during solid phase synthesis of an azapeptide. In some of these embodiments, R of compound of Formula (XVI) is selected from the group consisting of side chain radicals of aspartic acid, phenylalanine, alanine, histidine, glutamic acid, tryptophan, valine, leucine, lysine, methionine, tyrosine, R-isoleucine, S-isoleucine, and RS-isoleucine, arginine, glycine, asparagine, serine, threonine, cysteine and glutamine. The side chain radical may be unsubstituted or substituted with one or more of the following groups: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In some embodiments, B is selected from the group consisting of hydrogen, $—NH_2$, $—NNH_2$, $—CONH_2$, $—COOR_{19}$, $—COC_1$-$C_4$ alkyl, $—COC_1$-$C_4$ haloalkyl, —OH, an amino acid, an aza amino acid, a 2 to 60-mer peptide, a 2 to 60-mer aza peptide, a 2 to 60-merazatide; D is selected from the group consisting of $—OR_{20}$, $—NH_2$, $—NNH_2$, $—NHCOCH_3$, $—NHCH_3$, $—N(CH_3)_2$, $—CONH_2$, —COOH, —COH, $—COC_1$-$C_4$ alkyl, $—COC_1$-$C_4$ haloalkyl, an amino acid, an aza amino acid, a 2 to 60-mer peptide, a 2 to 60-mer aza peptide, a 2 to 60-merazatide; and $R_{19}$ and $R_{20}$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.); and R is selected from the group consisting of side chain radicals of aspartic acid, phenylalanine, alanine, histidine, glutamic acid, tryptophan, valine, leucine, lysine, serine, threonine, methionine, tyrosine, isoleucine (including, R-isoleucine, S-isoleucine and RS-isoleucine), arginine, glycine, asparagine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz). Compounds of Formula (XVI) may be used in drug discovery, diagnosis, prevention, inhibition, and treatment of diseases. In some embodiment, the process further comprises deprotecting the compound of Formula (XVI) with, e.g., hydrazine, piperadine, TFA, acetic acid, thioanisole, EDT, anisole, etc.

The invention is further directed in part to a process of preparing a compound of Formula (XVI) comprising cleaving a peptide at its N-terminus and/or C-terminus, and coupling the cleaved peptide with a compound according to any one of Formulas (I)-(IX) to form the compound of Formula (XVI).

The invention is also directed in part to a process of preparing a compound of Formula (XVI) comprising cleaving a peptide at its cleavage site to form two smaller peptides, replacing the last amino acid of at least one of the smaller peptides with a compound according to any one of Formulas (I)-(XII) to form an azapeptide, and conjugating the azapeptide with the remaining smaller peptide to provide a compound of Formula (XVI).

The invention is also directed in part to a process of preparing a compound of Formula (XVI) comprising hydrolizing a peptide at its cleavage site, and reacting the cleaved peptide with a compound according to any one of Formulas (I)-(XII) to provide a compound of Formula (XVI).

The invention is further directed in part to a method of azapeptide synthesis comprising reacting a compound according to any one of Formulas (I)-(XII) with an aza-amino acid, an amino acid, a peptide, an azapeptide, or an additional compound according to any one of Formulas (I)-(XII) to form an azapeptide. The azapeptide may be, e.g., a compound of Formula (XVI).

The invention is further directed in part to a solid phase synthesis of an azapeptide, the solid phase synthesis comprising coupling a compound according to any one of Formulas (I)-(XII) to a support, and coupling an additional protected compound according to any one of Formulas (I)-(XII), an additional protected amino acid, or an additional protected aza-amino acid to the deprotected compound of according to any one of Formulas (I)-(XII). In certain embodiments, the compound according to any one of Formulas (I)-(XII) may be deprotected prior to said coupling.

The invention is further directed in part to a solid phase synthesis of an azapeptide, the solid phase synthesis comprising coupling a compound according to any one of Formulas (I)-(XII) to a support, deprotecting the compound according to any one of Formulas (I)-(XII), and coupling the deprotected compound of according to any one of Formulas (I)-(XII) to a protected compound according to any one of Formulas (I)-(XII), a protected amino acid, or an a protected aza-amino acid.

The invention is further directed in part to a solution phase synthesis of the compounds of Formula (XVI), the solution phase synthesis comprising deprotecting a compound of any one of Formulas (I)-(XII), and coupling the deprotected compound of any one of Formulas (I)-(XII) with an additional compound any one of Formulas (I)-(XII), or a protected amino acid, or a protected aza-amino acid to form a protected azapeptide. The synthesis may further comprise a step of deprotecting the protected azapeptide to provide a compound of Formula (XVI). The coupling may, e.g., be for a time period of from about 15 minutes to about 12 hours. In certain embodiments, the coupling may be completed in about 30 minutes, about 40 minutes, about 50 minutes, about 60 minutes, about 70 minutes, about 80 minutes, about 90 minutes, about 100 minutes, about 110 minutes, or about 120 minutes.

The synthons and processes of the invention allow, e.g., preparation of unsubstituted and substituted thiocarbazates, semicarbazides, azapeptides and aza-peptide conjugates, e.g., in yields of at least about 50% (by weight) (e.g., from about 55% to about 99%, from about 60% to about 95%, or from about 65% to about 95%). Thus, the yield may, e.g., be about 55%, about 60%, about 65%, about 75%, about 80%, about 85%, about 90%, about 95%, about 97%, or about 99%. In certain embodiments, the yield is greater than 85%

Definitions

The term “about” in the present specification means a value within 15% (±15%) of the value recited immediately after the term “about,” including the value equal to the upper limit (i.e., +15%) and the value equal to the lower limit (i.e., −15%) of this range. For example, the phrase “about 100” encompasses any numeric value that is between 85 and 115, including 85 and 115.

An “azatide” means a peptide in which all α-carbons are replaced by nitrogen trivalent atoms.

An “α-nitrogen” means a nitrogen atom bonded to a carbonyl group in an azapeptide or an azatide. The carbon atom next to the α-nitrogen is called the β-carbon.

An “aza-amino acid” is defined as an amino acid where the chiral α-carbon atom is replaced by a nitrogen atom.

An “azapeptide analogue” means a compound which differs from a peptide that it is an analogue of in that one or more α-carbon atoms of the peptide have been replaced by a nitrogen atom with or without additional structural modification(s) to the side chain(s) of the amino acid residues of the peptide. The one or more α-carbon atoms of the peptide may, e.g., be at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide). Despite having a backbone different from the peptide, the azapeptide analogue preserves, extends and/or improves functional activity of the peptide. The azapeptide analogue is more resistant to degradation than the peptide and/or has an improved therapeutic activity than the peptide and/or has an improved selectivity for a biological receptor than the peptide and/or improved affinity to a biological receptor and/or reversed activity at a biological receptor (agonistic activity instead of antagonist activity or antagonistic activity instead of agonistic activity).

An “amine” in the process of the invention may, e.g., be an amino ester, an ester of an amino acid, an amino ester of an aza-amino acid, a peptide, or an aza-peptide, an amino acid, an aza-amino acid, provided that, if the amino ester, the ester of an amino acid, the amino ester of the aza-amino acid, the peptide, the aza-peptide, the amino acid, or the aza-amino acid contains a group selected from amino, amide, guanidino N, carboxyl, sulfhydryl, carboxyl, hydroxyl, indole, imidazole phenol, the group is protected with a protecting group selected from tert-butoxycarbonyl (Boc), 9-fluorenylmethoxycarbonyl (Fmoc), or 2-(3,5-dimethoxyphenyl)propan-2-yloxycarbonyl (Ddz), phthalimide (Phth), carboxybenzyl (Cbz), 2,2,4,6,7-pentamethyl-dihydrobenzofuran-5-sulfonyl (Pbf), trityl or triphenylmethyl (Trt), t-butyl ester (OtBu), t-butyl ether (tBu), allyloxycarbonyl (Aloc), methoxytrimethylbenzene sulfonyl (Mtr), 4,4-dimethyloxybenzhydryl (Mbh), 2,2,5,7,8-pentamethyl-chroman-6-sulfonyl chloride (Pmc), 2,4,6-trimethoxybenzyl (Tmob), allyl ester (OAl), acetamidomethyl (Acm), and the like. The amino ester may, e.g., be t-butyl, p-methoxy benzyl ester, glycine ethyl ester, etc.

The term “heteroaryl” includes all aryl compounds with atoms other than C and H.

The term “protected” as it is used herein means that one or more group(s) (e.g., —OH) in an amino acid, an aza-amino acid, a peptide, an azapeptide, or a compound is protected with a protecting group (e.g., Phth, Boc, Ddz, etc.). Unless otherwise indicated, the term “protecting group” or “protective group,” when used to refer to part of a molecule subjected to a chemical reaction, means a chemical moiety that is not reactive under the conditions of that chemical reaction, and which may be removed to provide a moiety that is reactive under those conditions. Protecting groups include, for example, nitrogen protecting groups and hydroxy-protecting groups. Examples of protective group include, e.g., benzyl, diphenylmethyl, trityl, Cbz, Boc, Fmoc, methoxycarbonyl, ethoxycarbonyl, Phth, Ddz, as well as other protective groups known to those skilled in the art.

The "amino acid side chain radical(s)" in the compounds of Formulas (I)-(XVI) may be a side chain radical of natural amino acid or a side chain radical of unnatural amino acid.

The unnatural amino acids include, e.g., aza-imidazole derivatives and Phth-protected carbamoyl aza-benzotriazole derivatives of β-amino acids (e.g., L-β-homotyrosine, β-alanine, L-β-homoasparagine, L-β-homoalanine, L-β-homophenylalanine, L-β-homoproline, L-β-holysine, L-β-homorarginine, L-β-proline, etc.), aliphatic amino acids (e.g., 6-aminohexanoic acid, 2-amino-3-methoxybutanoic acid, 1-aminocyclopentane-1-carboxylic acid, 2-(aminooxy)acetic acid, 6-aminohaxanoic acid, 2-[2-(amino)-ethoxy]-ethoxy}acetic acid), β-cyclohexyl-L-alanine, 6-aminohexanoic acid, L-α,β-diaminopropionic acid, L-propargylglycinel, L-α,β-diaminopropionic acid, α-aminoisobutyric acid, β-(2-pyridyl)-L-alanine, β-(3-pyridyl)-L-alanine, β-cyclopropyl-L-alanine, β-t-butyl-L-alanine, (2,4-dinitrophenyl))-L-α,β-diaminopropionic acid, (allyloxycarbonyl)-L-α,β-diaminopropionic acid, D-α,β-diaminopropionic acid, L-α,β-diaminopropionic acid, (N-γ-1-(4,4-dimethyl-2,6-dioxocyclohex-1-ylidene)ethyl)-L-α,γ-diaminobutyric acid, (N-γ-4-methyltrityl)-L-α,γ-diaminobutyric acid, L-α,γ-diaminobutyric acid, 4-fluoro-L-phenylglycine, 5,5,5-trifluoro-DL-leucine, epsilon-aminohexanoic-OH, L-α-t-butylglycine, L-2-amino-3-(dimethylamino)propionic acid, L-2-aminocaproic acid, L-allylglycine, lysine azide, (Nδ-4-methyltrityl)-L-ornithine, Arg(Me)(Pbf)-OH, dimethyl-L-arginine (symmetrical and unsymmetrical), L-2-amino-3-guanidinopropionic acid, L-citrulline, ε-acetyl-L-lysine, Lys(ivDde)-OH, Lys(Me)2-OH·HCl, Lys($Me_3$)-OHchloride, α-methyl-DL-glutamic acid, γ-carboxy-L-glutamic acid γ,γ-di-t-butyl ester, (N-γ-ethyl)-L-glutamine, 2,6-diaminopimelic acid, Glu(OAll)-OH, L-cysteic acid, α-methyl-DL-methionine, DL-buthionine, L-cysteic acid, L-selenomethionine, S-[2-(4-pyridyl) ethyl]-L-cysteine, S-[2-(4-pyridyl)ethyl]-L-cysteine, S-diphenylmethyl-L-cysteine, S-trityl-L-homocysteine, S-trityl-L-enicillamine, (Se-p-methoxybenzyl)-L-selenocysteine, β-hydroxyphenylalanine, 2-cyano-L-phenylalanine, L-thyroxine, O-methyl-L-tyrosine, β-methyl-DL-phenylalanine, 2-cyano-L-phenylalanine, L-thyroxine, O-methyl-L-tyrosine, β-methyl-DL-phenylalanine, 2-cyano-L-phenylalanine, 3,4-dichloro-L-phenylalanine, 3,4-difluoro-L-phenylalanine, 3,4-dihydroxy-L-phenylalanine, 3,4-dihydroxy-phenylalanine, 3-amino-L-tyrosine, 3-chloro-L-tyrosine, 3-fluoro-DL-tyrosine, 3-nitro-L-tyrosine, 4-amino-L-phenylalanine, 4-aminomethyl-L-phenylalanine, 4-(phosphonomethyl)-phenylalanine, 4-benzoyl-D-phenylalanine, 4-bis(2-chloroethyl)amino-L-phenylalanine, 4-cyano-L-phenylalanine, 4-fluoro-L-phenylalanine, 4-iodo-L-phenylalanine, DL-m-tyrosine, 2,6-dimethyl-tyrosine, L-homophenylalanine, O-methyl-L-tyrosine, Phe(4-guanidino) —OH, O-benzyl-L-phosphotyrosine, (2S,3R)-3-phenylpyrrolidine-2-carboxylic acid, (2S,4S)-4-phenyl-pyrrolidine-2-carboxylic acid, (2S,3aS,7aS)-Octahydro-1H-indole-2-carboxylic acid, (2S,3R)-3-phenylpyrrolidine-2-carboxylic acid, (2S,4R)-(−)-4-t-butoxypyrrolidine-2-carboxylic acid, trans-4-Fluoro-L-proline, (3S,4S)-4-amino-3-hydroxy-6-methylheptanoic acid, 4-amino-3-hydroxybutanoic acid, L-α-methylserine, (2S,3S)-2-amino-3-methoxybutanoic acid, Thr(β-D-GlcNAc(Ac)3)-OH, O-benzyl-L-phosphoserine, O-benzyl-D-phosphothreonine, O-benzyl-L-phosphothreonine, 4-methyl-DL-tryptophan, 6-fluoro-DL-tryptophan, 6-methyl-DL-tryptophan, DL-7-azatryptophan, (R)-7-Azatryptophan, 5-benzyloxy-DL-tryptophan, 5-bromo-DL-tryptophan, 5-chloro-DL-tryptophan, 5-fluoro-DL-tryptophan, 5-hydroxy-L-tryptophan, 5-methoxy-L-tryptophan, 6-chloro-L-tryptophan, 6-methyl-DL-tryptophan, 7-methyl-DL-tryptophan, DL-7-azatryptophan, 5-azido-pentanoic acid, 2-Amino-N-(3-azidopropyl)-3-mercaptopropionamide, 2-Amino-N-(3-azidopropyl)-3-mercaptopropionamide, Azidohomoalanine, L-propargylglycine·DCHA, azidolysine, p-azidophenylalanine, Azidohomoalanine, D-propargylglycine, L-propargylglycine, azidolysine, Tris[(1-benzyl-1H-1,2,3-triazol-4-yl)methyl] amine, 2-(7'-octenyl) alanine, 2-(4'-pentenyl) alanine, 2-(4'-pentenyl)glycine, 2-(7'-octenyl) alanine, [5-((2-Aminoethyl)amino)naphthalene-1-sulfonic acid], L-glutamic acid-γ-[2-(1-sulfonyl-5-naphthyl)-aminoethylamide], N-ε-(5-carboxyfluorescein)-L-lysine, N-ε-(5/6-carboxyfluorescein)-L-lysine, N-ε-(4,4-dimethylazobenzene-4'carbonyl)-L-lysine, Nε-2,4-dinitrophenyl-L-lysine, N-ε-[(7-methoxycoumarin-4-yl)-acetyl-L-lysine, glycosylated amino acids (e.g., Ser(β-D-GlcNAc(Ac)3)-OH, Thr(β-D-GlcNAc(Ac)3)-OH), 3-azabicyclo[3.1.0]hexane-2-carboxylic acid, 4-amino-(1-carboxymethyl) piperidine, 4-phenylpiperidine-4-carboxylic acid, Nα-methyl-N-im-trityl-L-histidine, Nα-methyl-O-benzyl-L-serine dicyclohexylammonium salt, Nalpha-methyl-Nomega-(4-methoxy-2,3,6-trimethylbenzenesulfonyl)-L-arginine, Nalpha-methyl-L-leucine, Nalpha-methyl-L-norvaline, Nalpha-methyl-L-phenylalanine, Nalpha-methyl-N-im-trityl-L-histidine, Nalpha-methyl-O-t-butyl-L-serine, Nalpha-methylglycine, 21-amino-4,7,10,13,16,19-hexaoxaheneicosanoic acid, {2-[2-(amino)-ethoxy]-ethoxy}acetic acid, 6-Amino-4-oxahexanoic acid, 5-Amino-3-Oxapentamoic Acid, NH-(PEG)10-CH2CH2COOH, NH-(PEG)12-CH2CH2COOH, 9-Amino-4; 7-Dioxanonanoic acid, 9-Amino-4; 7-Dioxanonanoic acid, 12-amino-4,7,10-trioxadodecanoic acid, 15-amino-4,7,10,13-tetraoxapentadecacanoic acid, 18-amino-4,7,10,13,16-pentaoxaoctadecanoic acid, 21-amino-4,7,10,13,16,19-hexaoxaheneicosanoic acid, NH-(PEG)8-CH2CH2COOH, 11-amino-3,6,9-trioxaundecanoic acid, N-(Fmoc-8-amino-3,6-dioxa-octyl)succinamic acid, —N-ε-acetyl-L-lysine, L-citrulline, Arg(Me)(Pbf)-OH, Nω,ω-dimethyl-L-arginine (asymmetrical and symmetrical), Lys(Me)$_2$-OH chloride, N-ε,ε-t-methyl-L-lysine, Lys(Me3)-OH chloride, O-benzyl-L-phosphoserine, O-benzyl-D-phosphothreonine, O-benzyl-L-phosphothreonine, O-benzyl-L-phosphotyrosine.

A "side chain radical" of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine have the following structures:

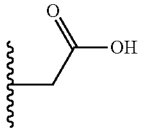

Aspartic Acid

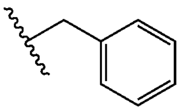

Phenylalanine

Alanine

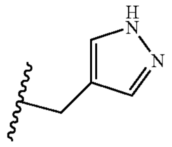

Histidine

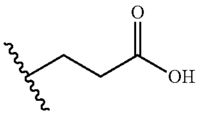

Glutamic Acid

-continued

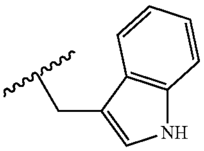

Tryptophan

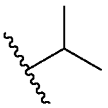

Valine

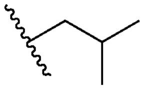

Leucine

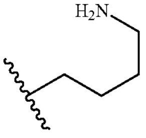

Lysine

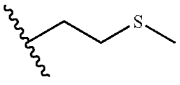

Methionine

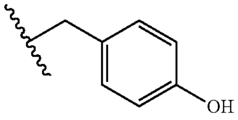

Tyrosine

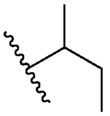

Isoleucine

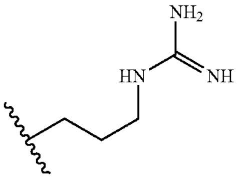

Arginine

Glycine

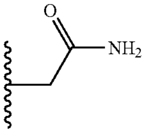

Asparagine

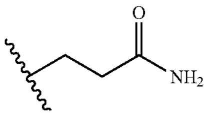

Glutamine

A "side chain radical of proline" is a secondary amine, in that the alpha-amino group is attached directly to the main chain, making the α carbon a direct substituent of the side chain:

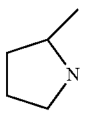

Amino acids which can be used in the present invention include L and D-amino acids.

Unless otherwise indicated, the terms "prevent," "preventing" and "prevention" contemplate an action that occurs before a patient begins to suffer from the symptoms of specified disease or disorder, which inhibits or reduces the severity of the disease or disorder or of one or more of its symptoms. The terms encompass prophylaxis.

The compounds of the invention can be used in the form of pharmaceutically acceptable salts derived from inorganic or organic acids. For clarity, the term "pharmaceutically acceptable salt[s]" as used herein generally refers to salts prepared from pharmaceutically acceptable acids or bases including inorganic acids and bases and organic acids and bases. Suitable pharmaceutically acceptable base addition salts include, e.g., metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific acids include, e.g., hydrochloric, hydrobromic, phosphoric, sulfuric, and methanesulfonic acids. Examples of specific salts include, e.g., hydrochloride and mesylate salts. Others are well-known in the art. See, e.g., Remington's Pharmaceutical Sciences, 18th ed. (Mack Publishing, Easton Pa.: 1990) and Remington: The Science and Practice of Pharmacy, 19th ed. (Mack Publishing, Easton Pa.: 1995). The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

Certain compounds of the present invention may be isotopically labelled, e.g., with various isotopes of carbon, fluorine, or iodine, as applicable when the compound in question contains at least one such atom. In preferred embodiments, methods of diagnosis of the present invention comprise administration of such an isotopically labelled compound.

Certain compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Certain compounds of the present invention may exist as cis or trans isomers, wherein substituents on a ring may attach in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

The term "solid-phase synthesis" means a method in which molecules (e.g., amino acids, aza-amino acids, etc.) are covalently bound on a solid support material and synthesised step-by-step in a single reaction vessel utilising selective protecting group chemistry. In this method, building blocks are typically protected at all reactive functional groups. The order of functional group reactions can be controlled by the order of deprotection. For example, in an aza-peptide synthesis, an amino-protected amino acid or an amino-protected aza-amino acid is bound to a solid phase material (e.g., low cross-linked polystyrene beads), forming a covalent bond between the carbonyl group and the resin, e.g., an amido or an ester bond. Then the amino group is deprotected and reacted with the carbonyl group of the next amino-protected amino acid or amino-protected aza-amino acid. This cycle is repeated to form the desired peptide or aza-peptide chain. After all reactions are complete, the synthesised peptide or aza-peptide is cleaved from the bead.

The terms "solution phase synthesis" and "liquid phase synthesis" means a method in which molecules (e.g., amino acids, aza-amino acids, etc.) are synthesized in a solution without being covalently bound on a solid support material.

The term "synthon" means a synthetic building block.

The term "room temperature" means 20° C.

The term "ambient temperature" means 18-28° C.

The terms "parent peptide" and "corresponding peptide" mean a native peptide (i.e., natural or convention peptide) that differs from an azapeptide in that one or more of the amino residue(s) of the native peptide is (are) replaced by a semicarbazide or a substituted semicarbazide (i.e., one or more α-carbon(s) of the native peptide are replaced by nitrogen trivalent atom(s)) in the azapeptide. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

The term "phthalimidyl" means:

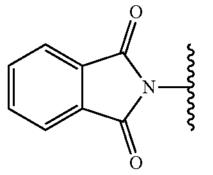 [SMILES: *N1C(=O)c2ccccc2C1=O]

The term "phthaloyl" means:

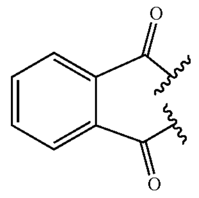 [SMILES: *C(=O)c1ccccc1C(*)=O]

The abbreviation "N-Phth" means "N-phthalimidyl."

The abbreviation "Boc" means "tert-butoxycarbonyl."

The abbreviation "Fmoc" means "9-fluorenylmethoxycarbonyl."

The abbreviation "Ddz" means "2-(3,5-dimethoxyphenyl) propan-2-yloxycarbonyl."

The abbreviation "HOBt" means "1-OH-Benzotriazole."

The abbreviation "SPPS" means "Solid Phase Peptide Synthesis."

The abbreviation "TCCA" means "trichloroisocyanuric acid."

The abbreviation "TBACl" means "tetrabutyl ammonium chloride."

The abbreviation "Phth" means "phthaloyl."

The abbreviation "Cbz" means "carboxybenzyl."

The abbreviation "Pbf" means "2,2,4,6,7-pentamethyl-dihydrobenzofuran-5-sulfonyl."

The abbreviation "Trt" means "trityl or triphenylmethyl."

The abbreviation "OtBu" means "O-t-butyl."

The abbreviation "tBu" means "t-butyl."

The abbreviation "Aloc" means "allyloxycarbonyl."

The abbreviation "Mtr" means "methoxytrimethylbenzene sulfonyl."

The abbreviation "Mbh" means "4,4-dimethyloxybenzhydryl."

The abbreviation "Pmc" means "2,2,5,7,8-pentamethyl-chroman-6-sulfonyl chloride."

The abbreviation "Tmob" means 2,4,6-trimethoxybenzyl.

The abbreviation "OAl" means "allyl ester."

The abbreviation "Acm" means "acetamidomethyl."

The abbreviation "DEAD" means "Diethyl Azodicarboxylate."

The abbreviation "TIPS" means TriIsoPropylSilane.

"Activation" of thiocarbazates or thiocarbamate as used herein means converting the thiocarbonyl moiety into active acyl donor. For example, when TCCA/TBACl are used, the anticipated active acyl donor is chloroformate moiter (acyl chloride).

"Coupling" means the event of adding a good nucleophile to the active acyl donor. For example, it includes formation of an amide, urea, or semicarbazide from the corresponding acyl chloride.

In peptide chemistry, "deprotection" refers to a process of removing the protecting groups (e.g., phthaloyl, Boc, Cbz, Fmoc, etc) by a chemical agent. For example, Boc protecting group could be removed under acidic conditions (e.g., 4M HCl, or neat trifluoroacetic acid TFA); Fmoc protecting group could be removed under basic conditions when pH is higher than 12 (20% pipyridine/DMF or DCM); and Phthaloyl group can be cleaved, e.g., under basic conditions or by the use of hydrazine.

DETAILED DESCRIPTION

Figure 1:
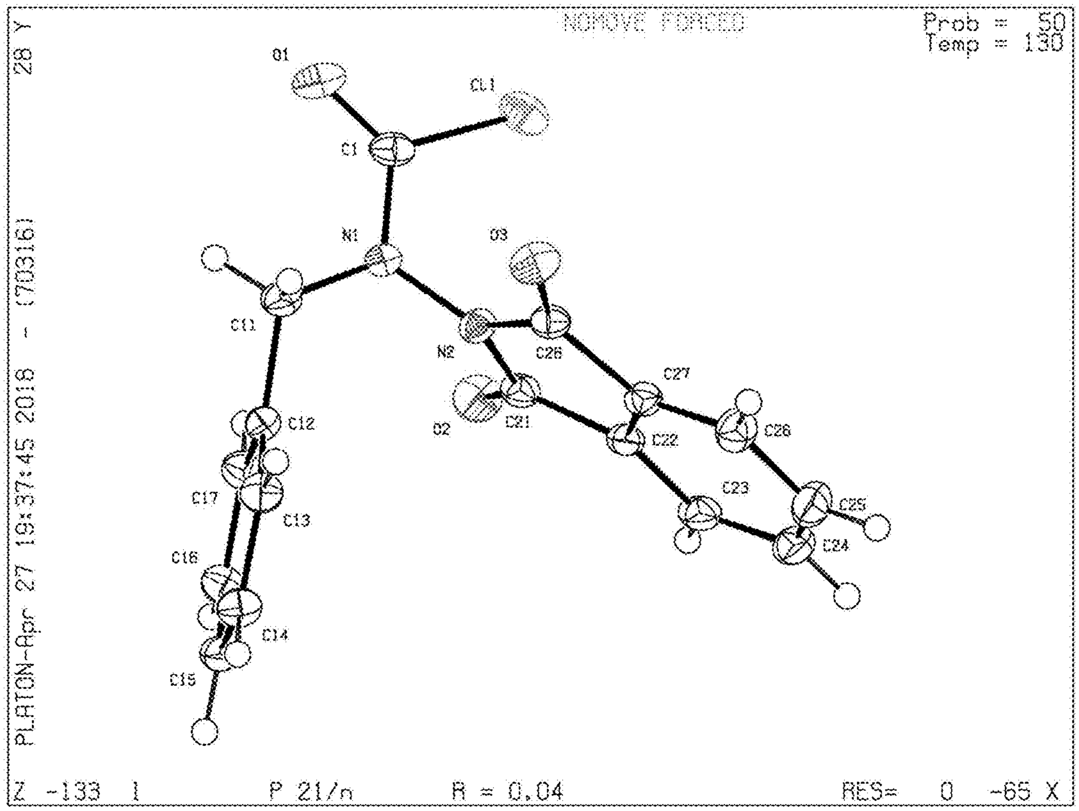
FIG. 1 depicts X-ray analysis of hydrazine carbonyl chloride chloroformate 35.
Figure 2:
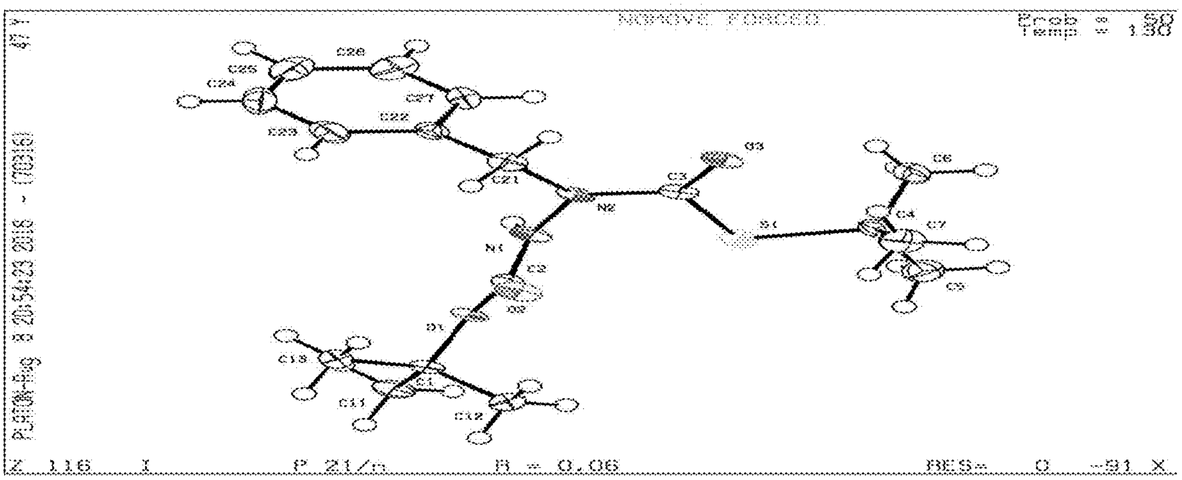
FIG. 2 depicts X-ray analysis of substituted ACTH 33 and 34.
Figure 2:
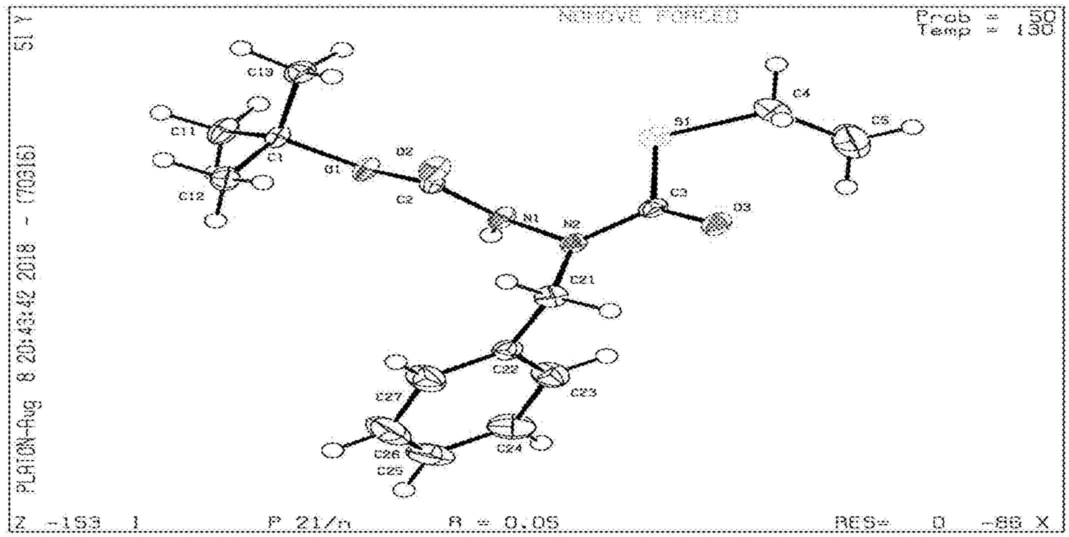
Figure 2:
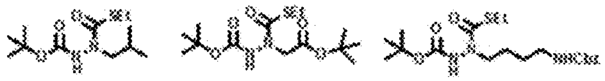
Figure 3:
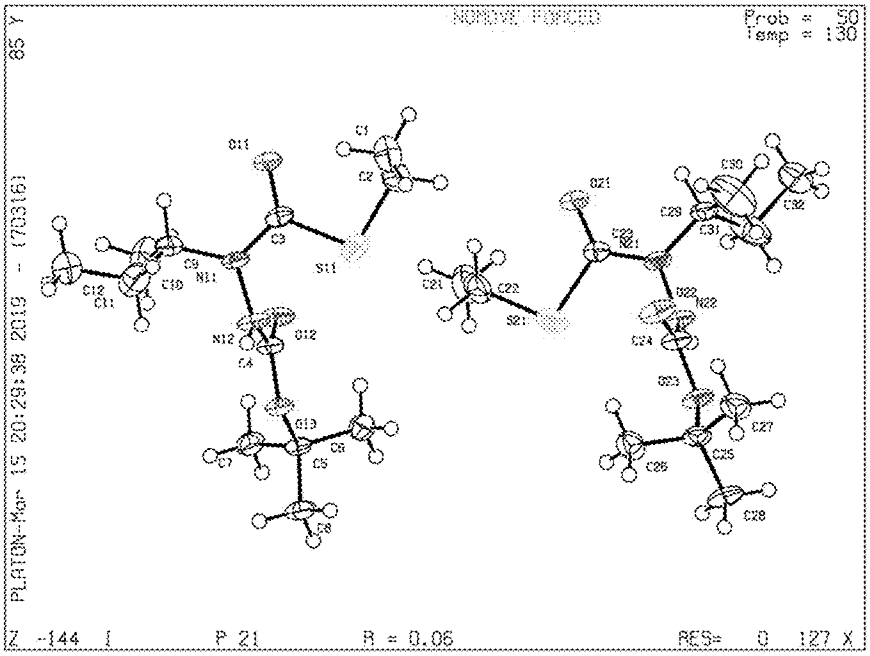
FIG. 3 depicts X-ray analysis of A7123.
Figure 3:
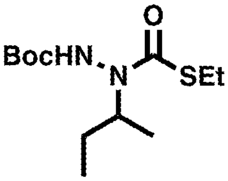
Figure 4:
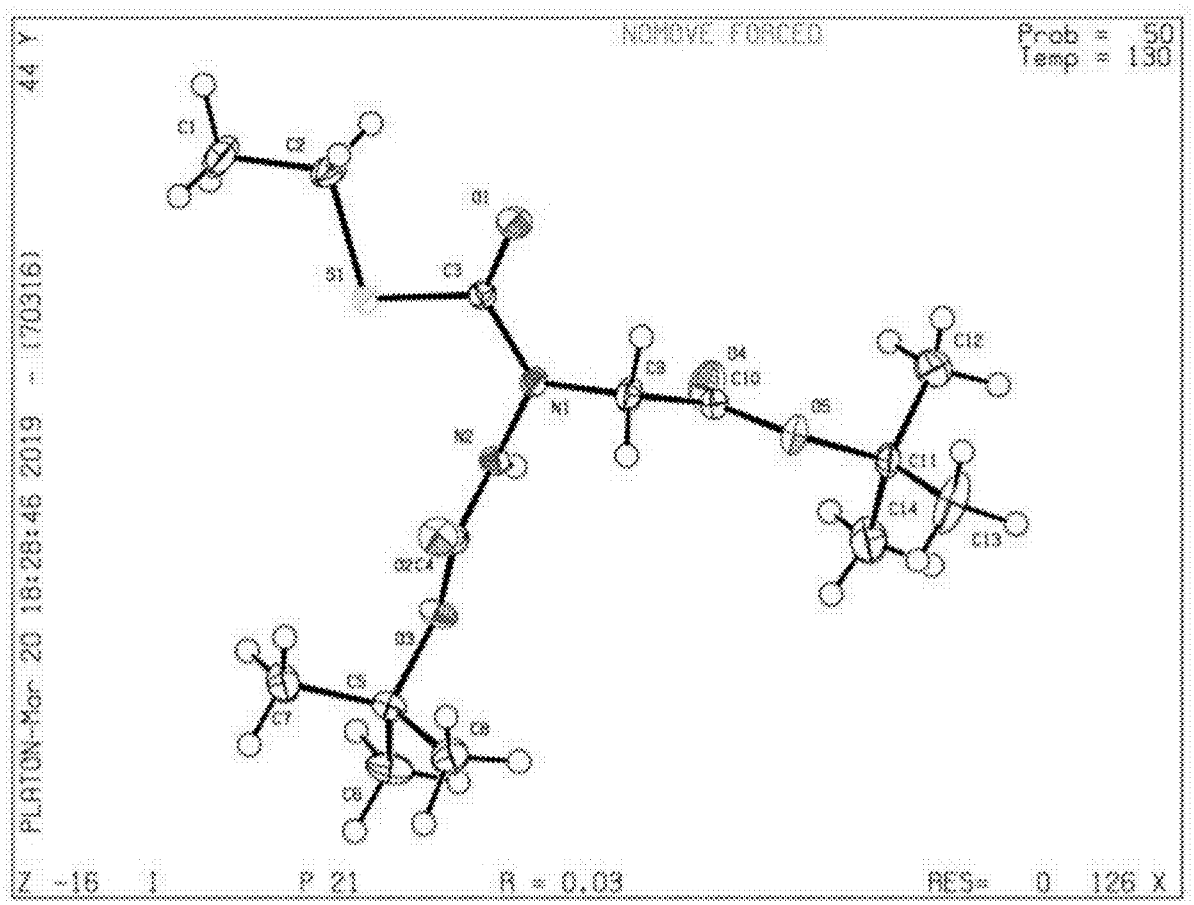
FIG. 4 depicts X-ray analysis of A790.
Figure 4:
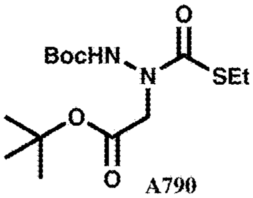
Figure 5:
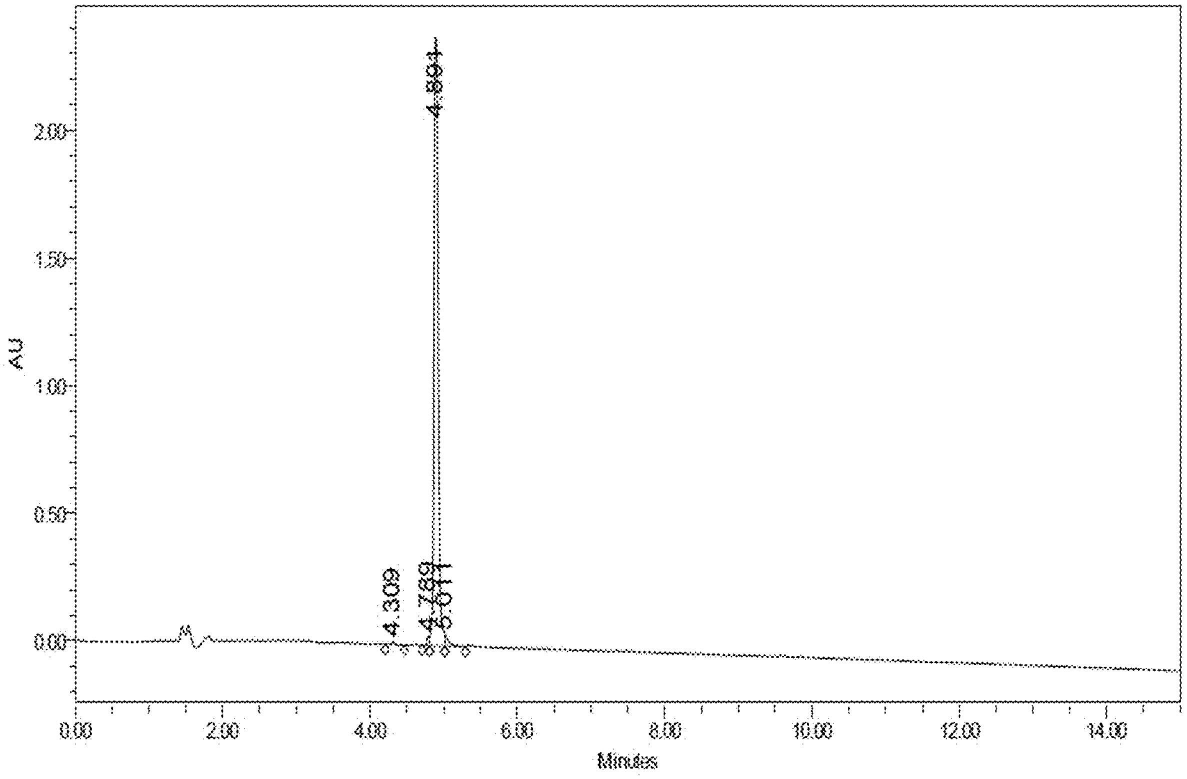
FIG. 5 depicts HPLC analysis for 2-azabradykinin made by SPPS.
Figure 6:
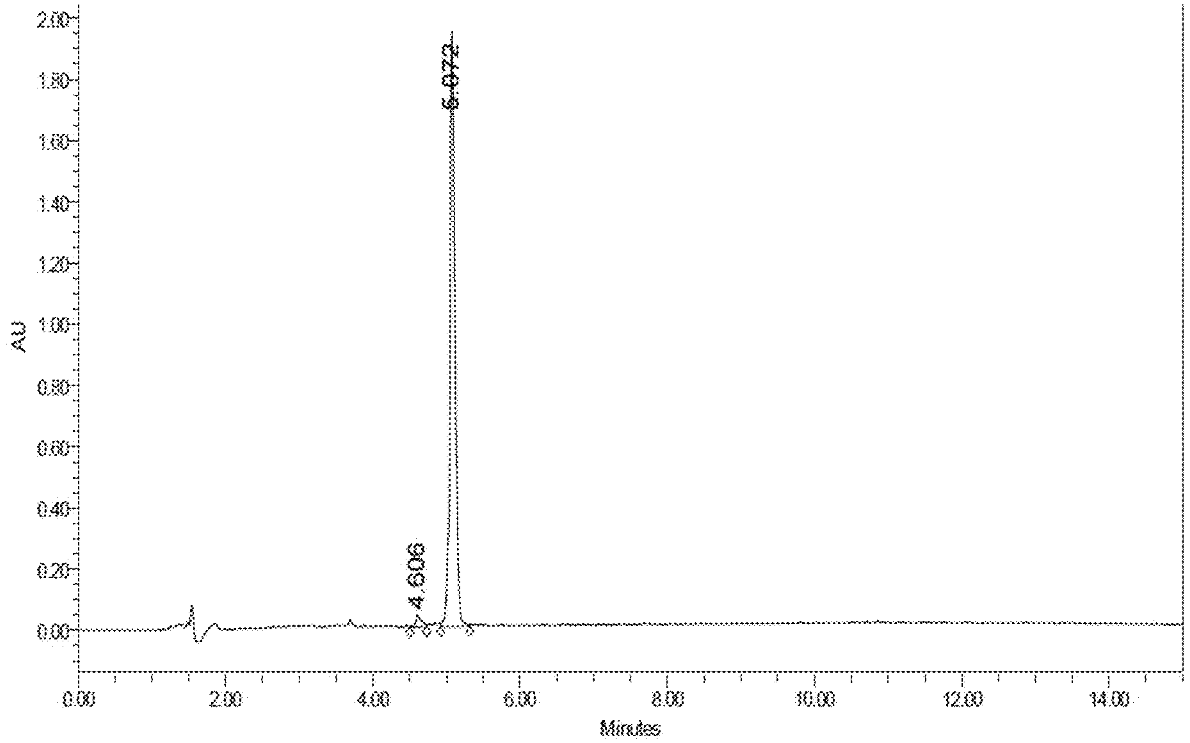
FIG. 6 depicts HPLC analysis for 8-azabradykinin made by SPPS.
Figure 7:
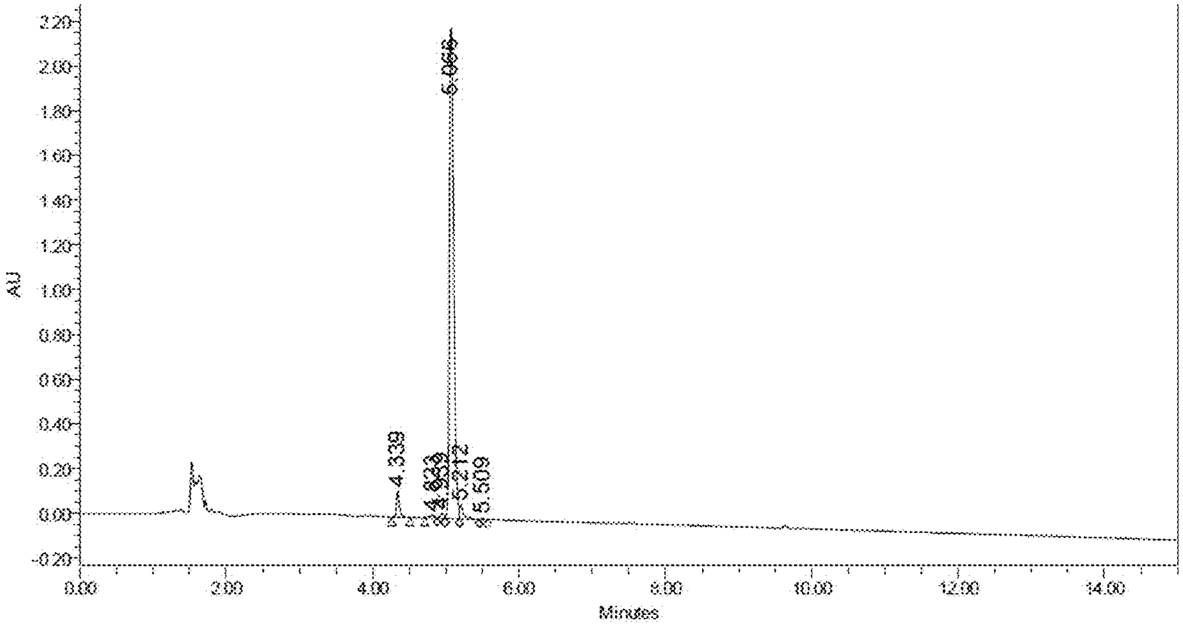
FIG. 7 depicts HPLC analysis for 7-azabradykinin made by SPPS.
Figure 8:
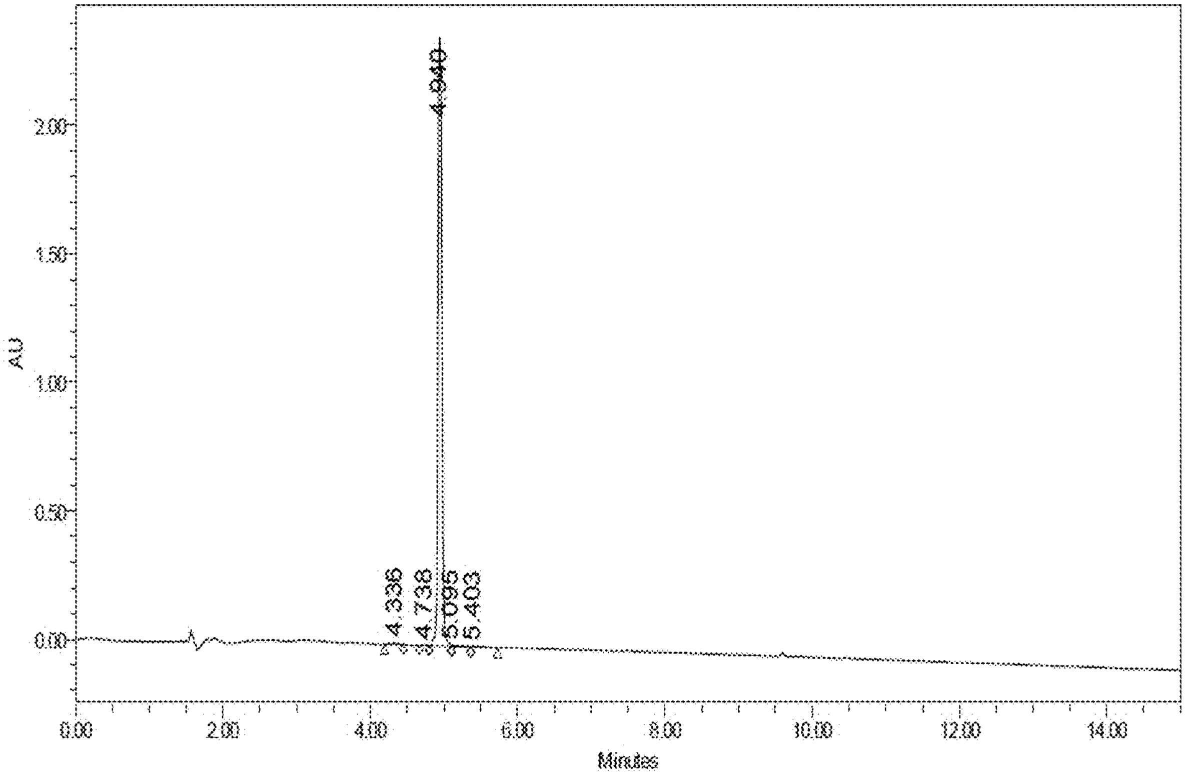
FIG. 8 depicts HPLC analysis for 2,8-azabradykinin made by SPPS.

The relatively small bond dissociation energies for the α-C—H bonds in amino acids and peptides compared to that in secondary and tertiary structures make the bond vulnerable to reactive free radicals and oxidants. As a result, some of these peptides are relatively unstable and show very short half-life times.

The exchange of a one or more specific amino acid moiety(ies) in the peptide sequence with an aza-amino acid produces azapeptides. This alteration in the peptide backbone introduces conformational changes because of the adjustable chirality on the alpha nitrogen. In addition, it has been suggested that the lone pair on the nitrogen atom plays a role through resonance to favor the 3-turn geometry. Resonance in the semicarbazide moiety also contributes to the reduced electrophilicity of the carbonyl system compare to that in typical amide.

Azapeptides exhibit, e.g., an extra stability to hydrolysis by proteases, as compared to the corresponding peptides.

Aza-Amino Acid Surrogates

Compounds of Formula (I) to (XII) are stable at 37° C. in an aqueous medium with a pH of about 7 (e.g., distilled water) for at least 30 minutes, 60 minutes, 90 minutes, 1 hour, 2 hours, 3 hours, 4 hours or 5 hours.

In certain embodiments, compounds of Formulas (I)-(XII) are protected S-alkylthiocarbazates and could be used instead of amino acids and aza-amino acids in the syntheses of ureases, carbazides, semicarbazides, beta-peptides, aza-peptides and other peptidomimetics and aza-peptide conjugates.

Various alkyl and the aromatic chains could be installed efficiently on the unsubstituted S-alkylthiocarbazates with yields ranging between, e.g., about 50% and about 99%, about 55% and about 97%, about 60% and about 95%, about 65% and about 95%, or about 70% to about 95%.

For example, protected unsubstituted S-alkylthiocarbazates may be prepared, e.g., by a reaction of a semi-protected hydrazine with a chlorothioformate to form an unsubstituted alkylthio carbonyl hydrazine (unsubstituted S-alkylthiocarbazate). The reaction may be conducted at a temperature, e.g., of from about 20° C. to about 35° C. in, e.g., 4-dimethyl amino pyridine (DMAP), or a tertiary amine (e.g., DIPEA, Et3N, NMM, any Lutidine, apyridine, or collidine) for a time period, e.g., of from about 5 minutes to about 10 hours, from about 10 minutes to about 9 hours, from about 20 minutes to about 8 hours, from about 30 minutes to about 6 hours, from about 45 minutes to about 5 hours, from about 1 hour to about 4 hours, or from about 1 hour to about 3 hours.

In certain embodiments, Mitsunobu reaction is used to prepare protected unsubstituted S-alkylthiocarbazates. Mitsunobu reaction may be carried out in ether solvents (e.g., tetrahydrofuran (THF)) where the substrate (thiocarbazate) is dissolved and treated with phosphine compounds like $Ph_3P$, Dialkyl Azodicarboxylate (e.g., DEAD), in addition to appropriate alcohol.

In some embodiments, the protected unsubstituted ATCH (an unsubstituted thiocarbazate) may be alkylated with an alcohol using the Mitsunobu reaction to form a compound of Formula (I) to (XII). The reaction may be conducted at temperature of from about −5° C. to about 15° C. or from about 0° C. to about 10° C. in, e.g., THF, Dioxane, $Et_2O$, DCM, toluene, xylene, chlorobenzene, etc., for a time period of from about 5 minutes to about 8 hours, from about 10 minutes to about 6 hours, from about 20 minutes to about 4 hours, from about 30 minutes to about 3 hours. In some of these embodiments, 40% of Diethyl Azodicarboxylate (DEAD) solution in toluene, or Diisopropyl Azodicarboxylate, (DIAD), a diazopyridine, a diazoarene, or a Dialkyl Azo dicarboxylate may be added to the reaction mixture drop-wise for a time period, e.g., of from about 1 min to about 12 hours, about 1 min to about 11 hours, about 1 min to about 10 hours, about 1 min to about 9 hours, about 1 min to about 8 hours, about 1 min to about 7 hours, about 1 min to about 6 hours, about 1 min to about 5 hours, about 1 min to about 4 hours, about 1 min to about 3 hours, about 1 min to about 2 hours, or about 1 min to about 1 hour. In some of these embodiments, a molar ratio of the protected unsubstituted ATCH and the alcohol is from 0.5:1 to 1:1.5, and the molar ratio of the protected unsubstituted ATCH and DEAD solution is from about 0.5:1.5 to about 1:3, and DEAD is added for a time period from about 1 min to about 1 hour. In some embodiments, from about 1 to about 3 mmol of $PPh_3$ or another tri alkyl or tri aryl phosphine (e.g., tricyclohexyl phosphine, tri butyl phosphine, and triphenyl phosphine) per mole of the protected unsubstituted ATCH (unsubstituted thiosemicarbazides) is used.

Scheme 1 show examples of preparation of unsubstituted protected ATCHs from semi-protected hydrazines 1, 2, 3, or 4:

Scheme 1: (R is H, an alkyl (e.g., a $C_1$-$C_{10}$ alkyl or aryl or heteroaryl)

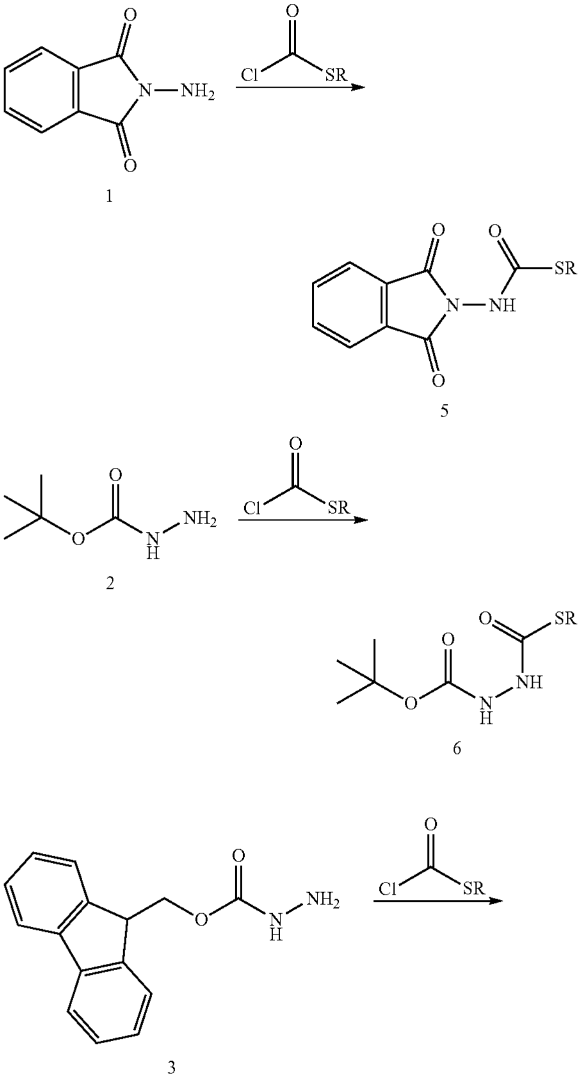

1

5

2

6

3

-continued

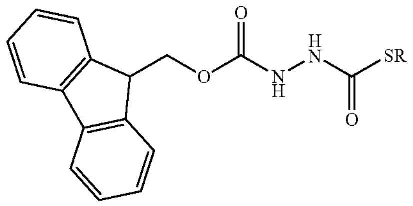

7

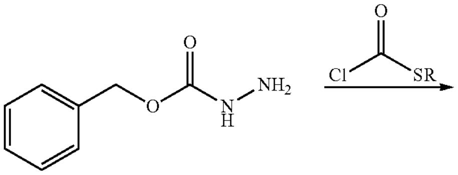

4

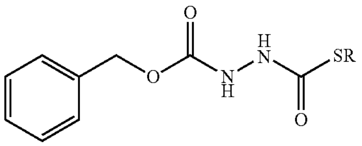

8

Protected unsubstituted ATCHs may have one available nitrogen for alkylation as in 5, or two nitrogen atoms as in 4 (Scheme 1).

Scheme 2 depicts examples of formation of substituted ACTHs by alkylation:

eq. 1

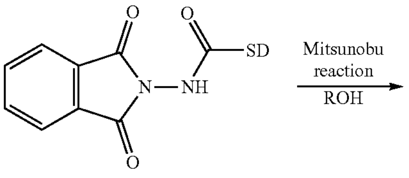

5

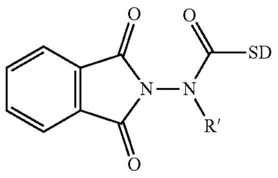

9 eq. 2

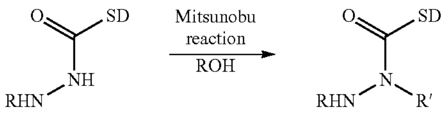

6 R = Boc
7 R = Fmoc
8 R = Cbz

10 R = Boc
11 R = Fmoc
12 R = Cbz

-continued eq. 3

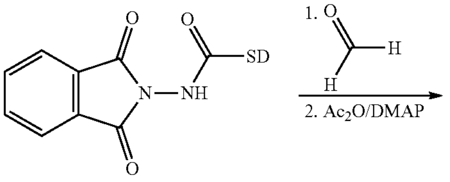

5

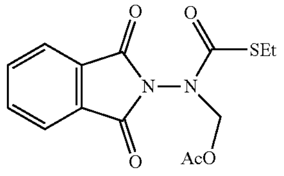

13 eq. 4

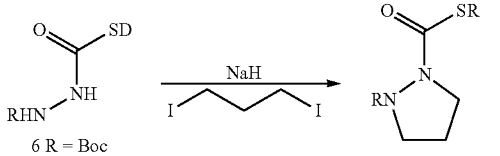

6 R = Boc

14 R = Boc

Scheme 2 (B is an alkyl (e.g., a $C_1$-$C_{10}$ alkyl), aryl, or heteroaryl), A is selected from the group consisting of H, substituted or unsubstituted branched and unbranched alkyls, substituted or unsubstituted aryls, substituted or unsubstituted heteroaryls, peptides, azapeptides, phthalimidyl (Phth), tert-butoxycarbonyl (Boc), 9-fluorenylmethoxycarbonyl (Fmoc), carboxybenzyl (Cbz), 2-(3,5-dimethoxyphenyl)propan-2-yloxycarbonyl (Ddz), 2,2,4,6,7-pentamethyl-dihydrobenzofuran-5-sulfonyl (Pbf), trityl or triphenylmethyl (Trt), t-butyl ester (OtBu), t-butyl ether (tBu), allyloxycarbonyl (Aloc), methoxytrimethylbenzene sulfonyl (Mtr), 4,4-dimethyloxybenzhydryl (Mbh), 2,2,5,7,8-pentamethyl-chroman-6-sulfonyl chloride (Pmc), 2,4,6-trimethoxybenzyl (Tmob), allyl ester (OAl), and acetamidomethyl (Acm), and R' is a protected or unprotected side chain of an amino acid or an ester thereof.

Alkylation may be, e.g., by the Mitsunobu reaction. Due to the different reactivities of the two nitrogen atoms in 6, 7, or 8, the reaction will grant an orthogonal functionalization of the nitrogen closer to the sulfur moiety, which is expected to be more nucleophilic than the other nitrogen under the Mitsunobu reaction due to the extra stability of the produced conjugate base because of the sulfur atom effect (eq. 1 & eq. 2 Scheme 2).

In scaffolds with a phthalimido-protecting group (e.g., 5), the Mitsunobu alkylation is secured because only one NH is available for alkylation. The reaction could be performed, e.g., at 0° C. in THE as a solvent, where the alkylthio carbonyl hydrazine is mixed with stoichiometric or excess of alkyl or aryl phosphine like $PPh_3$, $PCy_3$, $PBu_3$ and appropriate alcohol with a careful drop-wise treatment of Dialkyl azodicarboxylate, e.g. Diethyl azodicarboxylate (DEAD) Reagent. The products may then be isolated by standard flash chromatography and characterized by mass and NMR Spectroscopies to afford the desired ACTH (substituted thiocarbazate) with moderate to excellent yields. The yields for most of alcohols can be improved easily and efficiently during the R&D phase. Mintsunobu reaction conditions are mild and tolerated most of the alcohols needed to construct the ACTHs.

ATCHs may also be alkylated upon reflux with aldehydes. An example is depicted in eq. 3 in scheme 2, where the reaction of scaffold 5 with paraformaldehyde in toluene under reflux conditions followed by standard acetylation produces the acetate 13 in a good yield.

Direct alkylation using NaH and alkyl halides may also be used to functionalize ACTHs, e.g., to produce cyclic derivatives like the Aza-proline analog 14 depicted in eq. 4 in scheme 2.

Examples of substituted ACTHs that were prepared by the inventors are depicted in Scheme 3 (along with some of the yields achieved):

Scheme 3 (R″ is an alkyl or a protected or unprotected side chain of an amino acid or an ester thereof)

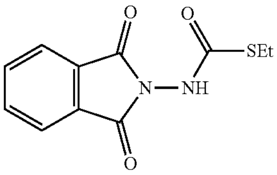

15

$Ph_3P$, alcohol
DEAD, THF
0° C. - rt

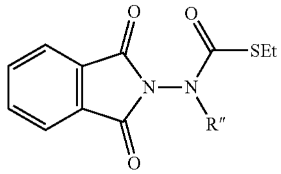

16

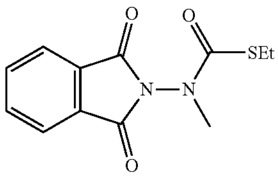

Aza-alanine
17 (99%)

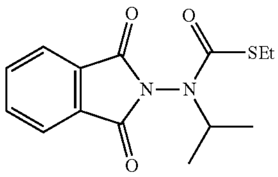

Aza-Valine
18 (55%)

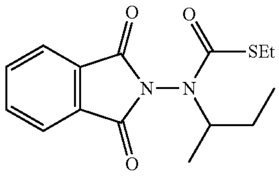

Aza-isoleucine
19 (78%)

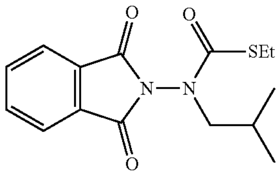

Aza-Leucine
20 (98%)

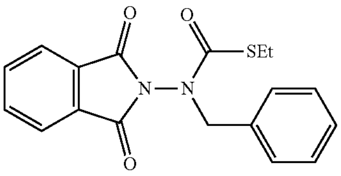

Aza-Phenylalanine
21 (87%)

-continued

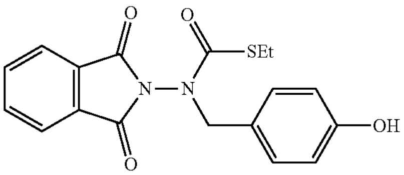

Aza-Tyrosine
22 (50%)

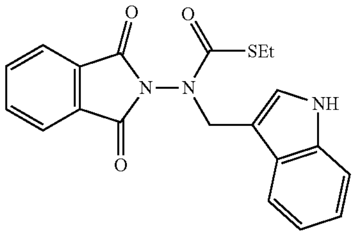

Aza-Tryptophane
23 (90%)

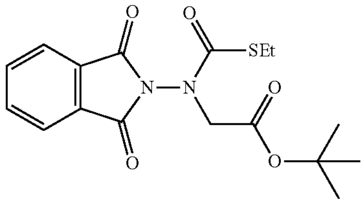

Aza-Aspartate
24 (93%)

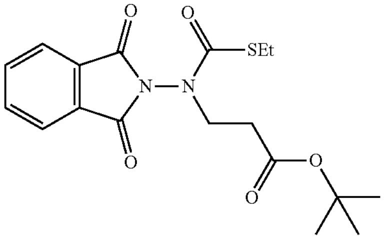

Aza-Glutamaic
25 (53%)

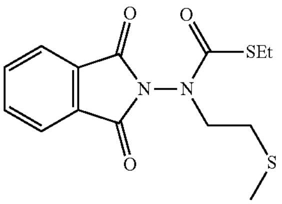

Aza-Methionine
26 (71%)

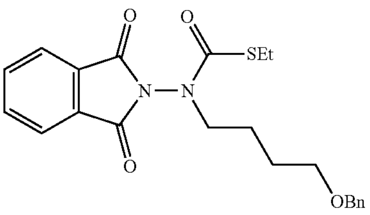

27 (85%)

-continued

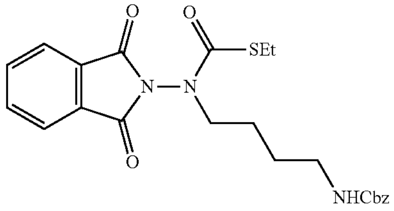

Aza-Lysine
28 (72%)

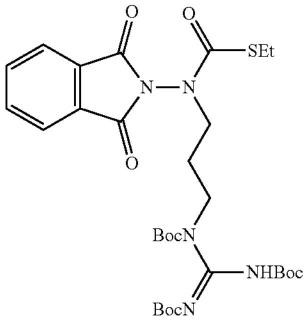

30
(34% over 2 steps)

The delicate indole moiety that is required to mimic the Tryptophane side chain could, e.g., be introduced with no other side products in, e.g., 9000 yield. Aza-aspartate surrogate 24 and Aza-Glutamate surrogate 25 can be produced, e.g., with 9300 and 5300 yields respectively as tert-butyl esters. The orthogonal choice of protecting groups is meant to expedite the elaboration of the synthetic options on all three sides of the protected functionalities.

The amine-containing side chains of the aza-amino acid surrogates can be built in a multistep fashion. For example, a simple and easily accessible starting materials like the 4-benzyl-1-butano can be used to synthesize surrogate 27. A commercially available benzyl (4-hydroxybutyl) carbamate can be used, e.g., in excess (e.g., 2 equivalents) to build the corresponding Aza-Lysine surrogate 29, e.g., in 70% yield. Aza-arginine surrogate 30 could be constructed over two steps with 35% using 1,3-propanediol as alkyl chain spacer. The Aza-Aspargine and the Aza-Glutamine surrogates can be accessed from the corresponding Aza-Aspartate surrogate 24 and the Aza-Glutamate surrogate 25, respectively. The Aza-Methionine surrogate 26 could be constructed, e.g., in 71% yield. Methionine surrogate 26 may be used as a building block to make the corresponding semicarbazides. Aza-serine surrogate 13 (Scheme 2) and the Aza-threonine surrogate may also be synthesized. An acetylated Aza-serine surrogate 13 can be produced in a good yield, e.g., by treatment of 15 with paraformaldehyde under reflux conditions in toluene followed by acetylation.

Protection groups other than phthalimidyl could also be used to prepare compounds of Formulas (I)-(XII). For example, carbamate-protected scaffolds like 31 and 32 could be used for selective alkylation as depicted in Scheme 4:

Scheme 4: Regioselective alkylation of the carbamate-protected thiocarbonyl hydrazines

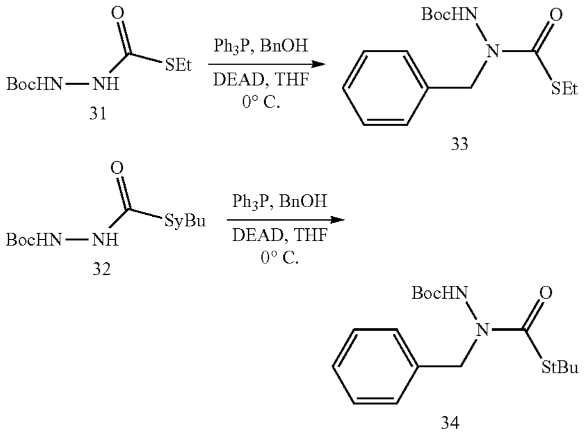

other examples for Boc protected alkyl thiocarbazates made by selective functionalization using the Mitsunobu reaction include, e.g.,

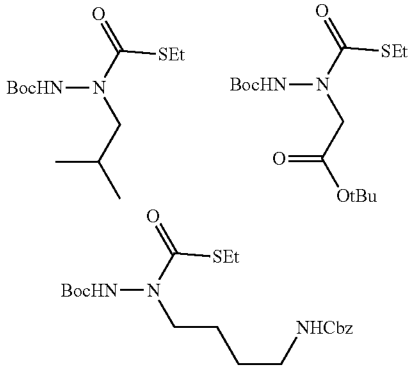

Carbamate-protected scaffolds like 31 and 32 could be built, e.g., from the commercially available t-butyl carbazate and the corresponding chlorothioformate, e.g., in 89% and 92% yields respectively. Both compounds 31 and 32 could be subjected separately to Mitsunobu reaction conditions and treated with stoichiometric amount of benzyl alcohol with slow addition of DEAD reagent. The alkylation favors the nitrogen atom closer to the alkyl thiocarbonyl moiety and will give selectively the Aza-phenylalanine surrogates 33 and 34, with, e.g., 70% and 85% yields respectively. Template 32 could be used to rule out the steric hindrance effect on the substitution. Compounds 33 and 34 could be isolated as crystalline materials to confirm the substitution pattern by X-ray analysis.

The substituted alkylthio carbonyl hydrazines (ATCHs), including compounds of Formulas (I) to (XII), could be used instead of aza-amino-acids in the synthesis of ureases, carbazides, semicarbazides, beta-peptides, azapeptides, and other peptidomimetics and aza-peptide conjugates.

Activation of Acylthiols

In literature, the abstraction of the alpha C—H in thioethers by the effect of N-chlorosuccinimide (NCS) is a well-documented reaction to activate thioethers and use them as reactive synthons. Thioesters and thiocarboxylic acids also have been reported to react with NCS to give sulfonyl chlorides in good yields under harsh acidic conditions. Thiocarbamates have been reported to provide chloroformates when exposed to chlorine gas or refluxed with sulfuryl chloride $SO_2Cl_2$. Scheme 5A depicts reactions of the literature:

(Scheme 5A)

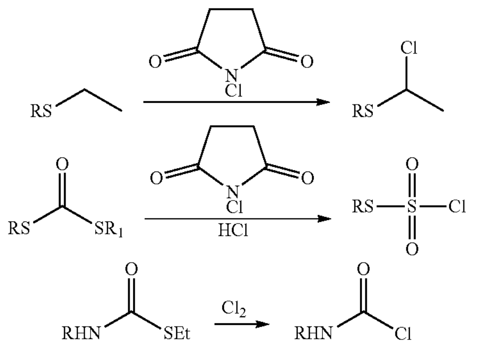

The invention provides an alternative way of activating acylthiols (e.g., compounds of Formulas (I)-(XII)) by using halonium reagents (e.g., TCCA or a mixture of TCCA and TBACl) to convert the acylthiols into acylium intermediates in situ. Halonium reagents are expected to abstract an α-hydrogen to the sulfur atom and increase the migration aptitude of the thiolate group to form an isocyanate intermediate in the case of urea or carbonyl hydrazine or an acylium intermediate in the case of thioester. Exemplary reactions of the invention are depicted in Scheme 5B:

Scheme 5B: (R and R′ could each independently be PG, analkyl, a protected or unprotected side radical of an amino acid or an ester thereof, PG is a protecting group (e.g., PhthM a carbamate protecting group, e.g., Boc, Fmoc, Cbz. etc.))

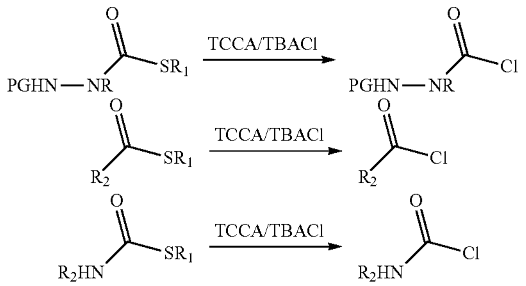

The activation of acylthiols by using halonium reagents avoids, e.g., a need for the unpractical and the harsh reaction conditions reported in the literature. The activated acylthiols can then be coupled with an amine. The amine may be, e.g., an amino ester, an ester of an amino acid, an amino ester of an aza-amino acid, a peptide, an aza-peptide, an amino acid, an aza-amino acid. If the amino ester, the ester of an amino acid, the amino ester of the aza-amino acid, the peptide, the aza-peptide, the amino acid, or the aza-amino acid contains a group selected from amino, amide, guanidino N, carboxyl, sulfhydryl, carboxyl, hydroxyl, indole, imidazole phenol, the group may be protected with a protecting group selected from tert-butoxycarbonyl (Boc), 9-fluorenylmethoxycarbonyl (Fmoc), or 2-(3,5-dimethoxyphenyl)propan-2-yloxycarbonyl (Ddz), phthalimide (Phth), carboxybenzyl (Cbz), 2,2,4,6,7-pentamethyl-dihydrobenzofuran-5-sulfonyl (Pbf), trityl or triphenylmethyl (Trt), t-butyl ester (OtBu), t-butyl ether (tBu), allyloxycarbonyl (Aloc), methoxytrimethylbenzene sulfonyl (Mtr), 4,4-dimethyloxybenzhydryl (Mbh), 2,2,5,7,8-pentamethyl-chroman-6-sulfonyl chloride (Pmc), 2,4,6-trimethoxybenzyl (Tmob), allyl ester (OAl), acetamidomethyl (Acm), and the like. In some embodiments, the amine is an amino ester (e.g., be t-butyl, p-methoxy benzyl ester, glycine ethyl ester, etc).

The common protecting groups appear to be stable under the conditions necessary to activate compounds of Formula (I)-(XII) by halonium reagents. The reaction can be conducted, e.g., in chloroform, dichloromethane, acetone, acetonitrile, etc.

Thioureas and thiocarbonyl hydrazines have less reactive carbonyl systems toward nucleophilic addition, as compared to the corresponding thioesters due to the resonance effect of the neighboring nitrogen. Consequently, varying the reaction conditions could afford wide range of functionalities.

Coupling of Activated Acylthiols

Once compounds of Formulas (I)-(XII) are activated they can be coupled to an amine to make unsubstituted and substituted semicarbazides, e.g., azapeptides and other peptidomimetics and aza-amino acid conjugates. The amine may be, e.g., an amino ester, an ester of an amino acid, an amino ester of an aza-amino acid, a peptide, an aza-peptide, an amino acid, an aza-amino acid. If the amino ester, the ester of an amino acid, the amino ester of the aza-amino acid, the peptide, the aza-peptide, the amino acid, or the aza-amino acid contains a group selected from amino, amide, guanidino N, carboxyl, sulfhydryl, carboxyl, hydroxyl, indole, imidazole phenol, the group may be protected with a protecting group selected from tert-butoxycarbonyl (Boc), 9-fluorenylmethoxycarbonyl (Fmoc), or 2-(3,5-dimethoxyphenyl)propan-2-yloxycarbonyl (Ddz), phthalimide (Phth), carboxybenzyl (Cbz), 2,2,4,6,7-pentamethyl-dihydrobenzofuran-5-sulfonyl (Pbf), trityl or triphenylmethyl (Trt), t-butyl ester (OtBu), t-butyl ether (tBu), allyloxycarbonyl (Aloc), methoxytrimethylbenzene sulfonyl (Mtr), 4,4-dimethyloxybenzhydryl (Mbh), 2,2,5,7,8-pentamethyl-chroman-6-sulfonyl chloride (Pmc), 2,4,6-trimethoxybenzyl (Tmob), allyl ester (OAl), acetamidomethyl (Acm), and the like. In some embodiments, the amine is an amino ester (e.g., be t-butyl, p-methoxy benzyl ester, glycine ethyl ester, etc).

In certain embodiments, A of compounds of Formulas (I)-(XII) is phthalimidyl, and these compounds are activated by TCCA to convert them into acylium intermediates in situ by an exemplary reaction depicted in Scheme 6, and the resulting acylium intermediate is reacted with an amine (e.g., glycine ethyl ester), e.g., in DIPEA to form a substituted or unsubstituted semicarbazide:

Scheme 6

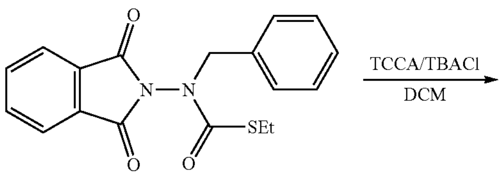

21

-continued

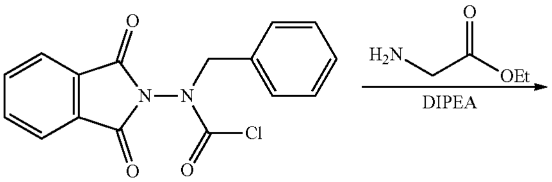

35

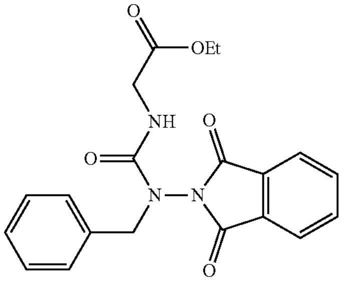

36

In certain embodiments, the activated acylthiol is coupled with an amino ester. The careful and orthogonal choice of amino acid ester is important. Acid labile esters (e.g., like t-butyl, p-methoxy benzyl esters, etc.) are compatible with the phthalimide group. However, careful handling of the cleaving of the phthalimido group under controlled temperature is also feasible. The use of amino esters as coupling partners reduces unwanted side products formed as a result of reactions of free carboxylic acids with, e.g., TCCA, a mixture of TCCA and TBACl, etc.

In certain embodiments, A of compounds of Formulas (I)-(XII) is Boc, and these compounds are activated by halonium reagents to convert them into acylium intermediates in situ by a reaction depicted in Scheme 8, and the resulting acylium intermediate is then reacted with an amine (e.g., an aminoacid ester) to form an unsubstituted or substituted semicarbazide:

Scheme 8: TCCA coupling protocol for Boc protected scaffolds

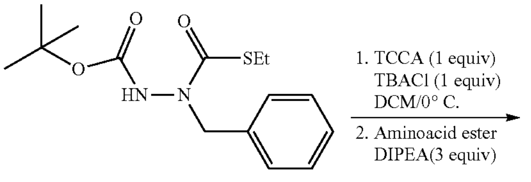

33

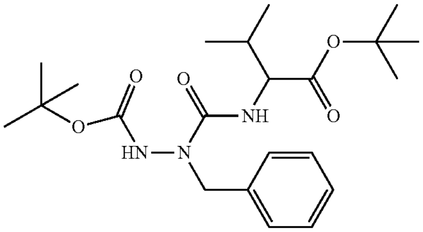

51 (89%)

-continued

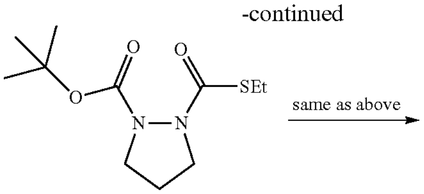

14

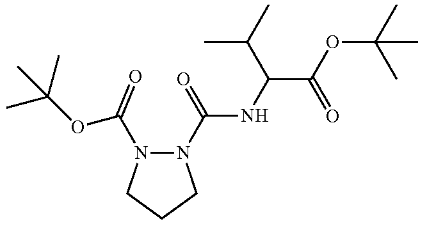

52 (68%)

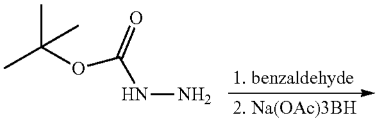

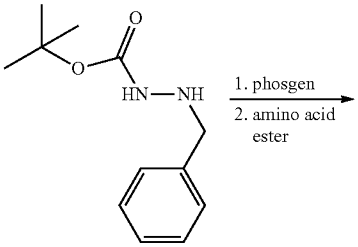

51

The unsubstituted and substituted semicarbazides can be used, e.g., as diazide surrogates, to make azapeptides and other peptidomimetics and aza-amino acid conjugates, e.g., in solid phase peptide synthesis (SPPS) or a solution peptide synthesis.

Synthesis of Ureases, Carbazides, Semicarbazides, Beta-Peptides, Azapeptides and Other Peptidomimetics and Aza-Amino Acid Conjugates Compounds of Formulas (I) to (XII) can be coupled in a linear, stepwise, chain-lengthening fashion to each other, amino acids, aza-amino acids, peptides, azapeptides, and azatides by solution phase, solid phase and mixed solution/solid phase synthetic methodologies to construct semicarbazides, beta-peptides, azapeptides and other peptidomimetics and aza-amino acid conjugates. For example, when the synthons are used in the synthesis of an azapeptide, the azapeptide is preferably produced in a yields ranging between about 55% and 99% (by weight) (e.g., from about 60% to about 95% or from about 65% to about 95%). The yield may, e.g., be about 55%, about 60%, about 65%, about 75%, about 80%, about 85%, about 90%, about 95%, about 97%, or about 99%. In certain embodiments, the average yield after both activating and coupling is greater than 85% for most of the amino acid residues combinations.

Compounds of Formula (I) to (XII) can also be used, e.g., as sub-monomers to elongate and/or cap peptides and azapeptides.

For example, in certain embodiments, compounds of Formula (I) to (XII) may be activated by a halonium reagent(s) (e.g., TCCA or a mixture of TCCA and TBACl), and the activated compound may be coupled, e.g., a protected or unprotected aza-amino acid; a protected or unprotected a peptide; a protected or unprotected azapeptide; a protected or unprotected azatide; or a protected or unprotected compound of Formula (I) to (XII); or a protected or unprotected hydrazine, by either solution or solid phase synthetic methodologies, e.g., to form an aza-peptide. The amino acid, the aza-amino acid, the peptide, the azapeptide, compound of Formula (I) to (XII) may each be unsubstituted or substituted with one or more of the following: a halogen (Cl, F, or Br), a $C_1$-$C_6$ alkyl (e.g., methyl), hydroxyl, methoxyl, ethoxyl, propoxyl, a $C_1$-$C_6$ haloalkyl (e.g., a chloromethyl, a fluromethyl, etc.).

The methods of the invention may be used to synthesize, e.g., azapeptides from 2 to 200 mers in length, e.g., di-azatides, tri-azatides, tetra-azapeptides, penta-azapeptides, etc.

In certain embodiments, the method of preparing an azapeptide or an azatide comprises hydrolysing a peptide into fragments and reacting one or more fragments with a compound of Formula (I) to (XII).

In certain embodiments, the method of preparing an azapeptide or an azatide comprises cleaving a peptide into fragments and reacting one or more fragments with a compound of Formula (I) to (XII).

In certain embodiments, the method of preparing an azapeptide or an azatide comprises cleaving an end of a peptide, and reacting the cleaved peptide with a compound of Formula (I) to (XII).

In certain embodiments, the method of preparing an azapeptide or an azatide comprises reacting a compound of Formula (I) to (XII) with a truncated peptide.

In certain embodiments, a method of azapeptide or azatide synthesis comprise reacting (i) a compound of formula (I) to (XII) with (ii) a peptide to form the azapeptide or azatide, wherein the azapeptide or azatide is a compound of formula (XVI).

In certain embodiments, a compound of formula (I) to (XII) is a substituted semicarbazide. The substituted semicarbazide may be prepared, e.g., by activating a compound of formula (I) to (XII) with a halonium reagent(s) (e.g., TCCA or a mixture of TCCA and TBACl). The activated compound is then reacted with an amine, e.g., in the presence of diisopropylethylamine (DIPEA, Et3N, Me3N, NMO, Lutidines, pyridines, DMAP, collidines, or any tertiary amine). In some of these embodiments, the compound of formula (I) to (XII), TCCA and TBACl are used in a molar ratio of about 1:1:1. The molar ratio of the compound of formula (I) to (XII) to the amine may, e.g., be from about 0.5:1 to 1:1.5. In some embodiments, DCM is added to the reaction mixture. The reaction may be conducted for a time period of from about 5 minutes to about 5 hours at a temperature of from about −5° C. to about 30° C. In some embodiments, the reaction mixture is cooled before addition of the amine. In some embodiments, the reaction mixture may be treated with saturated solution of sodium thiosulfate.

In certain embodiments, a compound of formula (I) to (XII) is a substituted semicarbazide. The substituted semicarbazide may be prepared, e.g., by exposing a compound of formula (I) to (XII) with TCCA or a mixture of TCCA and TBACl to activate the compound, and then reacting the activated compound with an amine, e.g., in the presence of diisopropylethylamine (DIPEA, Et3N, Me3N, NMO, Lutidines, pyridines, DMAP, collidines, or a tertiary amine). In some of these embodiments, the compound of formula (I) to (XII), TCCA and TBACl are used in a molar ratio of about 1:1:1. The molar ratio of the compound of formula (I) to (XII) to the amine may, e.g., be from about 0.5:1 to 1:1.5. In some embodiments, DCM is added to the reaction mixture. The reaction may be conducted for a time period of from about 5 minutes to about 5 hours at a temperature of from about −5° C. to about 30° C. In some embodiments, the reaction mixture is cooled before addition of the amine. In some embodiments, the reaction mixture may be treated with saturated solution of sodium thiosulfate.

Synthesis of Compounds of Formula (XVI)

In certain embodiments, compounds of Formulas (I) to (XV) are used to synthesize compounds of Formula (XVI). Compound of Formula (XVI) may be used in drug discovery, diagnosis, prevention, inhibition, and treatment of diseases. For example, compound of Formula (XVI) may be used to inhibit one or more symptom(s) of the diseases. Compound of Formula (XVI) may be used to completely alleviate one or more symptom(s) of the diseases. In certain embodiments, compounds of Formula (XVI) are azapeptide analogues of therapeutic and diagnostic peptides and are more resistant to hydrolysis and/or enzymatic degradation than the therapeutic and diagnostic peptides.

Compound of Formula (XVI) may comprise from 2 to 200 carbonyl group(s). For example, compound of Formula (XVI) may comprise 2, 3, 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 36, 37, 38, 39, 40, 41, 43, 44, 56, or 166 carbonyl groups. In certain embodiments, compound of Formula (XVI) comprises from 2 to 60 carbonyl groups, from 2 to 50 carbonyl groups, from 2 to 40 carbonyl groups, from 2 to 30 carbonyl groups, from 2 to 25 carbonyl groups, from 2 to 20 carbonyl groups, from 2 to 15 carbonyl groups, from 2 to 12 carbonyl groups, from 2 to 10 carbonyl groups, from 2 to 9 carbonyl groups, from 3 to 40 carbonyl groups, from 3 to 30 carbonyl groups, from 3 to 25 carbonyl groups, from 3 to 20 carbonyl groups, from 3 to 15 carbonyl groups, from 3 to 12 carbonyl groups, from 3 to 10 carbonyl groups, or from 3 to 9 carbonyl groups.

In certain embodiments, compound of Formula (XVI) comprises from 2 to 200 carbonyl groups and at least one α-nitrogen covalently bound to at least one of said carbonyl groups, and have a greater bioavailability (e.g., oral, transdermal, and/or intranasal) than a compounds that lacks the at least one α-nitrogen. In certain embodiments, the α-nitrogen is not at the N-termini and not at the C-termini of the compounds of Formula (XVI), rather it is at a cleavage or hydrolysis site(s) of the peptide.

In certain embodiments, compounds of Formula (XVI) comprises a backbone comprising from 2 to 200 carbonyl groups and α-nitrogen covalently bound to at least one of said carbonyl groups, and is therapeutically effective for the treatment of a disorder in a subject. Compounds of Formula (XVI) may, e.g., inhibit or completely alleviate one or more symptom(s) of the disorder in the subject.

In certain embodiments, the compound of Formula (XVI) comprises from 2 to 60 carbonyl groups.

In certain embodiments, the compound of Formula (XVI) is linear.

In certain embodiments, the compound of Formula (XVI) is cyclic.

In certain embodiments, the compound of Formula (XVI) is pegylated.

In certain embodiments, the compound of Formula (XVI) is conjugated to an immunoglobulin.

In certain embodiments, the compound of Formula (XVI) comprises α-nitrogen at the N-terminus of its backbone.

In certain embodiments, the compound of Formula (XVI) comprises α-nitrogen at the C-terminus of its backbone.

In certain embodiments, the compound of Formula (XVI) comprises two carbonyl groups and two α-nitrogens.

In certain embodiments, the compound of Formula (XVI) comprises three carbonyl groups and one α-nitrogen.

In certain embodiments, the compound of Formula (XVI) comprises three carbonyl groups and two α-nitrogens.

In certain embodiments, the compound of Formula (XVI) comprises three carbonyl groups and three α-nitrogens.

In certain embodiments, the compound of Formula (XVI) comprises four carbonyl groups and one α-nitrogen.

In certain embodiments, the compound of Formula (XVI) comprises four carbonyl groups and two α-nitrogens.

In certain embodiments, the compound of Formula (XVI) comprises four carbonyl groups and three α-nitrogens.

In certain embodiments, the compound of Formula (XVI) comprises four carbonyl groups and four α-nitrogens.

In certain embodiments, compounds of Formula (I) to (XII) are used to prepare aza-analogues of A-6, A-623 (AMG-623), A-71378, A-75998, Abarelix (PPI-149), ABT-510, AC-100, AC-162352 (PYY 3-36), AC-253, AC-2592, AC-625, ACV-1, ADH-1, AEZS-108 (AN-152) (ZEN-008), AF-37702, Afamelanotide (EP-1647) (CUV-1647) (Melanotan I), AG2/102, AG-284, AI-502, AKL-0707 (LAB GHRH), Albiglutide (GSK-716155), Albuvirtide, ALG-889, Alloferon, Allotrap 2702 (B-2702), ALTY-0601, ALX-40-4C, Ambamustine (PTT-119), Anaritide, Antagonist G (PTL-68001), AOD-9604, APL-180, ATN-161, Atosiban (ORF-22164), Atriopeptin, Aviptadil (PSD-510), Avorelin (EP-23904), AZD-2315, Azetirelin (YM-14673), AZX-100, B27PD, BA-058, Barusiban (FE-200400), BAY-73-7977, BDM-E, BGC-728, BIM-23190, BIM-44002, BIO-1211, Bivalirudin (BG-8865), BMS-686117, Bremelanotide (PT-141), BRX-0585, Buserelin, Calcitonin (Human), Calcitonin (Salmon), Carbetocin, Carfilzomib (PR-171), Cargutocin (Y-5350), Carperitide (SUN-4936), Casokefamide, CB-182804, CB-183315, CBP-501, CBT-101, CCK (25-33), CD-NP, Cemadotin (LU-103793), Cetrorelix (NS-75), CG-77X56, CGRP (LAB-CGRP), Chlorotoxin (TM-601), Cilengitide (EMD-121974) (EMD-85189), CJC-1008 (DAC: Dynorphin A), CJC-1131 (DAC:GLP-1), CJC-1134 (PC-DAC) (Exendin-4), CJC-1295 (DAC:GRF), Cnsnqic-Cyclic (802-2), Compstatin (POT-4), Conantokin G, Contulakin G (CGX-1007), Corticorelin (NEU-3002), CP-95253, C-peptide (SPM-933), CR-665, CR-845, CTCE-0214, CTCE-9908, CTS-21166 (ASP-1702) (ATG-Z1) (OM-00-3) (OM-99-2), CVX-045, CVX-060, CVX-096 (PF-4856883), CZEN-002, D-4F (APP-018), Danegaptide (ZP-1609) (WAY-261134) (GAP-134), Davalintide (AC-2307), Davunetide (AL-108) (AL-208), Degarelix (FE 200486), Delmitide (RDP-58), Deltibant (CP-0127), Deslorelin, Desmopressin, Detirelix (RS-68439), DG-3173 (PTR-3173), Didemnin B (NSC-325319), Dirucotide (MBP-8298) Disitertide (NAFB-001) (P-144), DMP-728 (DU-728), dnaJP1 (AT-001), Dopastatin (BIM-23A760), DPK-060, DRF-7295, DSC-127, Dynorphin A, E-2078, EA-230, Ebiratide (Hoe-427), Edotreotide (SMT-487), Edratide (TV-4710), Efegatran (LY-294468), Elcatonin, Eledoisin (ELD-950), Elisidepsin (PM-02734), EMD-73495, Enfuvirtide (T-20), EP-100, EP-51216 (EP-51389), Eptifibatide (C68-22), ET-642 (RLT-peptide), ETRX 101, Examorelin (EP-23905) (MF-6003), Exenatide (AC-2993) (LY-2148568), Exsulin (INGAP Peptide), F-991, FAR-404, FE 202158, Felypressin, FGLL, Frakefamide (LEF-576) (SPD-759) (BCH-3963), FX-06, Ganirelix (Org-37462) (RS-26306), Glaspimod (SKF-107647), Glatiramer (COP-1), Glucagon, Glucosamyl muramyl tripeptide, Glutoxim (NOV-002), Glypromate, GMDP, Golotimod (SCV-07), Goralatide (BIM-32001), Goserelin (ICI-118630), GPG-NH2, GTP-200, GTP-300, H-142, Hemoparatide (PTH(1-37)), Hexapeptide copper II (PC-1358), Histrelin, hLF(1-11), HP-228, I-040302 (KUR-112), Icatibant (JE-049) (HOE-140), lcrocaptide (ITF-1697), IMX-942, lpamorelin (NNC-26-0161), IPP-201101, Iseganan (IB-367), ISF402, Iturelix (ORF-23541), JTP-2942, KAI-1455, KAI-1678, KM-9803, KP-101 (GHRP-1), L-346670, L-364343, Labradimil (RMP-7), Lagatide (BN-52080), Lanreotide (ITM-014), Larazotide (AT-1001) (SPD-550), Leconotide (AM-336), Leuprolide (SOT-375), Linaclotide (MD-1100) (MM-41775), Liraglutide (NN-2211), Lixisenatide (AVE-0010) (ZP-10), LSI-518P, Lucinactant, Lusupultide (BY-2001), LY-2189265, LY-2510924, LY-548806, LYN-001, Lypressin, MER-104, Met-enkephalin (INNO-105), Metkephamide (LY-127623), Mifamurtide (CGP-19835) (MLV-19835), Montirelin (CG-3703), MPL-TLB100, MS peptide, MT-ll (PT-14), Murabutide (VA-101) (CY-220), Muramyl tripeptide, Nafarelin (RS-94991), NBI-6024, Nemifitide (INN-00835), Neogen, Nepadutant (MEN-11420), Nesiritide, Nifalatide (BW942C), NNZ-2566, NP-213, NFC-567, NPY (24-36) (PTL-041120), NT-13, Obinepitide (TM-30338), Octreotide (SMS-201-995), Oglufanide (IM-862), OGP 10-14L, Omiganan (CPI-226), OP-145, ORG-2766 Org-42982 (AG-4263), Ornithine vasopressin, Oxytocin, Ozarelix (D-63153) (SPI-153), p-1025, P-113 (PAC-113), Pasireotide (SOM-230), peg-TPOmp (RWJ-800088), Pentigetide (TA-521), Pep-F (5K), Peptide renin inhibitor, Peptide T (AIDS000530), Peptide YY 3-36, Pexiganan (MSI-78), PF-4603629, PI-0824, PI-2301, PL-3994, PLD-116, PMX-53, POL-6326, Posatirelin, PPI-1019, Pralmorelin, Pramlintide, Protirelin, PTH (7-34), PTHrP-(1-36), PTL-0901, PXL-01, R-1516, R-15-K, R-7089, RA peptide, Ramorelix (Hoe-013), RC-3095, Re-188-P-2045 (P2045), rGRF, Romiplostim (AMG-531), Romurtide (DJ-7041), ROSE-010 (GTP-010) (LY-307161), Rotigaptide (ZP-123) (GAP-486), Rusalatide (TP-508), SAN-134, Saralasin (P-113), Secretin (human) (PGN-52) (R-52), Secretin (human) (RG-1068), Semaglutide (NN-9535), SGS-111 Sifuvirtide, SKF-101926, SKF-105494, SKF-110679 (U-75799E), Soblidotin (YHI-501) (TZT-1027), Somatostatin, Somatostatin (D-Trp, D-Cys analog), SP-304 (Guanilib), SPC-3, SPI-1620, SST analog, SUN-11031, SUN-E7001 (CS-872), SYN-1002, Tabilautide (RP-56142), TAK-448, TAK-683, Taltirelin (TA-0910), Tasidotin (ILX-651) (BSF-223651), Taspoglutide (BIM-51077), TCMP-80, Teduglutide (ALX-0600), Teriparatide (LY-333334), Terlakiren (CP-80794), Terlipressin, Tesamorelin (TH-9507), Teverelix (EP-24332), TH-0318, TH-9506, Thymalfasin, Thymodepressin, Thymonoctan (FCE-25388), Thymopentin (TP-5), Thymosin beta-4, Tifuvirtide (R-724) (T-1249), Tigapotide (PCK-3145), Tiplimotide (NBI-5788), TKS-1225 (Oxyntomodulin), TLN-232 (CAP-232)(TT-232), TM-30339, TP-9201, TRI-1144, Tridecactide (AP-214), Triletide (Z-420) (ZAMI-420), Triptorelin (WY-42462), TT-223 (E1-INT), TT-235, TX14(A), Tyroserleutide (CMS-024), Tyroservatide (CMS-024-02), Ularitide (CDD-95-126) (ESP-305), Unacylated ghrelin (AZP-01) (TH-0332), Urocortin 11, Vapreotide (RC-160), Vasopressin, VIR-576, Xen-2174, XG-102, XOMA-629, Ziconotide (SNX-111), ZP-120, or ZP-1846.

In certain embodiments, compounds of Formula (I) to (XII) are used to prepare aza-analogues of AC-2592, AC-625, Anaritide, APL-180, Atriopeptin, BGC-728, Carperitide (SUN-4936), CD-NP, CG-77X56, D-4F (APP-018), Danegaptide (ZP-1609) (WAY-261134) (GAP-134), DMP-728 (DU-728), Efegatran (LY-294468), EMD-73495, Eptifibatide ($C_{68}$-22), ET-642 (RLT-peptide), FE 202158, FX-06, Icatibant (JE-049) (HOE-140), lcrocaptide (ITF- 1697), KAI-1455, KM-9803, L-346670, L-364343, LSI-518P, Nesiritide, Peptide renin inhibitor, PL-3994, Rotigaptide (ZP-123) (GAP-486), Saralasin (P-113), SKF-105494, Terlakiren (CP-80794), Tridecactide (AP-214), Ularitide (CDD-95-126) (ESP-305), Urocortin ll, Ziconotide (SNX-111), or ZP-120; and have utility in the treatment of cardiovascular diseases (e.g., alleviate one or more symptom(s) of the cardiovascular disease).

In certain embodiments, compounds of compounds of Formula (I) to (XII) are used to prepare aza-analogues of Azetirelin (YM-14673), Conantokin G, Corticorelin (NEU-3002), CTS-21166 (ASP-1702) (ATG-Z1) (OM-00-3) (OM-99-2), Davunetide (AL-108) (AL-208), Deltibant (CP-0127), Ebiratide (Hoe-427), FGLL, Glypromate, JTP-2942, Montirelin (CG-3703), Nemifitide (INN-00835), NNZ-2566, NT-13, ORG-2766, Peptide T (AIDS000530), Posatirelin, PPI-1019, Protirelin, Secretin (human) (RG-1068), SGS-111, Taltirelin (TA-0910), XG-102, or Ziconotide (SNX-111), and have utility in the treatment of CNS disorders (e.g., alleviate one or more symptom(s) of the CNS disorder).

In certain embodiments, compounds of Formula (I) to (XII) are used to prepare aza-analogues of A-6, Abarelix (PPI-149), ABT-510, ADH-1, AEZS-108 (AN-152) (ZEN-008), Ambamustine (PTT-119), Antagonist G (PTL-68001), ATN-161, Avorelin (EP-23904), Buserelin, Carfilzomib (PR-171), CBP-501, Cemadotin (LU-103793), Chlorotoxin (TM-601), Cilengitide (EMD-121974) (EMD-85189), CTCE-9908, CVX-045, CVX-060, Degarelix (FE 200486), Didemnin B (NSC-325319), DRF-7295, Edotreotide (SMT-487), Elisidepsin (PM-02734), EP-100, Glutoxim (NOV-002), Goralatide (BIM-32001), Goserelin (ICI-118630), Histrelin, Labradimil (RMP-7), Leuprolide (SOT-375), LY-2510924, Met-enkephalin (INNO-105), Mifamurtide (CGP-19835) (MLV-19835), Muramyl tripeptide, Ozarelix (D-63153) (SPI-153), POL-6326, Ramorelix (Hoe-013), RC-3095, Re-188-P-2045 (P2045), Romurtide (DJ-7041), Soblidotin (YHI-501) (TZT-1027), SPI-1620, Tabilautide (RP-56142), TAK-448, TAK-683, Tasidotin (ILX-651) (BSF-223651), Teverelix (EP-24332), Tigapotide (PCK-3145), TLN-232 (CAP-232)(TT-232), Triptorelin (WY-42462), Tyroserleutide (CMS-024), Tyroservatide (CMS-024-02), ZP-1848, in ZT0131; and have utility in the treatment of oncological conditions (e.g., alleviate one or more symptom(s) of the an oncological condition).

In certain embodiments, compounds of Formula (I) to (XII) are used to prepare aza-analogues of A-623 (AMG-623), AG-284, AI-502, Allotrap 2702 (B-2702), AZD-2315, Cnsnqic-Cyclic (802-2), Delmitide (RDP-58), Dirucotide (MBP-8298) Disitertide (NAFB-001) (P-144), dnaJP1 (AT-001), Edratide (TV-4710), F-991, FAR-404, Glaspimod (SKF-107647), Glatiramer (COP-1), GMDP, IPP-201101, Icatibant (JE 049)(HOE-140), MS peptide, Org-42982 (AG-4263), Pentigetide (TA-521), PI-0824, PI-2301, PLD-116, PMX-53, PTL-0901, RA peptide, TCMP-80, Thymodepressin, Thymopentin (TP-5), Tiplimotide (NBI-5788), or ZP-1848; and have utility in the treatment of allergy and immunology disorders.

In certain embodiments, compounds of Formula (I) to (XII) are used to prepare aza-analogues of A-71378, AC-162352 (PYY 3-36), AC-253, AG2/102, AKL-0707 (LAB GHRH), Albiglutide (GSK-716155), AOD-9604, BAY-73-7977, BIM-44002, BMS-686117, BRX-0585, CJC-1131 (DAC:GLP-1), CJC-1134 (PC-DAC) (Exendin-4), CJC-1295 (DAC:GRF), CP-95253, CVX-096 (PF-4856883), Davalintide (AC-2307), Exenatide (AC-2993) (LY-2148568), Exsulin (INGAP Peptide), Glucagon, ISF402, Liraglutide (NN-2211), Lixisenatide (AVE-0010) (ZP-10), LY-2189265, LY-548806, nafarelin (RS 94991), NBI-6024, Obinepitide (TM-30338), Peptide YY 3-36, PF-4603629, Pramlintide, R-7089, Semaglutide (NN-9535), SST analog, SUN-E7001 (CS-872), Taspoglutide (BIM-51077), Tesamorelin (TH-9507), TH-0318, TKS-1225 (Oxyntomodulin), TM-30339, TT-223 (E1-INT), Unacylated ghrelin (AZP-01) (TH-0332), or ZT0131, and have utility in the treatment of metabolic disorders (e.g., alleviate one or more symptom(s) of a metabolic disorder).

In certain embodiments, compounds of Formula (I) to (XII) are used to prepare aza-analogues of A-75998, Buserelin, Cetrorelix (NS-75), Detirelix (RS-68439), Ganirelix (Org-37462) (RS-26306), Iturelix, Nafarelin (RS-94991), or triproletin (WY-42462); and have utility in the treatment of fertility.

In certain embodiments, compounds of Formula (I) to (XII) are used to prepare aza-analogues of AC-100 and p-1025, and have utility in the treatment of dental disorders.

In certain embodiments, compounds of Formula (I) to (XII) are used to prepare aza-analogues of ACV-1, Conantokin G, CJC-1008 (DAC: Dynorphin A), Contulakin G (CGX-1007), CR-665, CR-845, Dynorphin A, E-2078, Felypressin, Frakefamide (LEF-576) (SPD-759) (BCH-3963), HP-228, Icatibant (JE-049) (HOE-140), KAI-1678, Leconotide (AM-336), Metkephamide (LY-127623), MPL-TLB100, NT-13, SYN-1002, TX14(A), Xen-2174, and Ziconotide (SNX-111); and have utility in the treatment of pain.

In certain embodiments, compounds of Formula (I) to (XII) are used to prepare aza-analogues of Afamelanotide (EP-1647) (CUV-1647) (Melanotan I), AZX-100, DPK-060, DSC-127, Hemoparatide (PTH(1-37)), Hexapeptide copper II (PC-1358), Pexiganan (MSI-78), PTH (7-34), PXL-01, SKF-110679 (U-75799E), or Thymosin beta-4; and have utility in the treatment of dermatologic conditions (e.g., alleviate one or more symptom(s) of a dermatological condition).

In certain embodiments, compounds of Formula (I) to (XII) are used to prepare aza-analogues of AF-37702, Bivalirudin (BG-8865), carfilomib, (PR-171), CTCE-0214, ETRX 101, H-142, OGP 10-14L, Ornithine vasopressin, peg-TPOmp (RWJ-800088), R-1516, Romiplostim (AMG-531), and TP-9201; and have utility in the treatment of hematology disorders (e.g., alleviate one or more symptom(s) of a hematological disorder).

In certain embodiments, compounds of Formula (I) to (XII) are used to prepare aza-analogues of Albuvirtide, ALG-889, Alloferon, ALX-40-4C, CB-182804, CB-183315, CZEN-002, Enfuvirtide (T-20), Glucosamyl muramyl tripeptide, Golotimod (SCV-07), GPG-NH2, hLF(1-11), IMX-942, Iseganan (IB-367), Murabutide (VA-101) (CY-220), Neogen, NP-213, Oglufanide (IM-862), Omiganan (CPI-226), OP-145, p-1025, P-113 (PAC-113), Pep-F (5K), R-15-K, Sifuvirtide, SPC-3, Thymalfasin, Thymonoctan (FCE-25388), Tifuvirtide (R-724) (T-1249), TRI-1144, VIR-576, or XOMA-629; and have utility as an antimicrobial or antiviral agent.

In certain embodiments, compounds of Formula (I) to (XII) are used to prepare aza-analogues of ALTY-0601, B27PD, BDM-E, BIM-23190, CBT-101, Compstatin (POT-4), Eledoisin (ELD-950), and LYN-001, and have utility in the treatment of ophthalmologic disorders (e.g., alleviate one or more symptom(s) of an ophthalmologic disorder).

In certain embodiments, compounds of Formula (I) to (XII) are used to prepare aza-analogues of Atosiban (ORF-22164), Barusiban (FE-200400), Carbetocin, Cargutocin (Y-5350), Deslorelin, Oxytocin, or TT-235, and have utility in the treatment of OB-GYN disorders.

In certain embodiments, compounds of Formula (I) to (XII) are used to prepare aza-analogues of Aviptadil (PSD-510), Bremelanotide (PT-141), C-peptide (SPM-933), Desmopressin, EA-230, Lypressin, MER-104, MT-ll (PT-14), SKF-101926, or Vasopressin, and have utility in the treatment of urologic conditions (e.g., alleviate one or more symptom(s) of a urologic condition).

In certain embodiments, compounds of Formula (I) to (XII) are used to prepare aza-analogues of AC-100, BA-058, Calcitonin (Human), Calcitonin (Salmon), Elcatonin, I-040302 (KUR-112), PTHrP-(1-36), Rusalatide (TP-508), SAN-134, Teriparatide (LY-333334), or ZT031; and have utility in the treatment of bones and connective tissue disorders.

In certain embodiments, compounds of Formula (I) to (XII) are used to prepare aza-analogues of BIO-1211, CGRP (LAB-CGRP), Glucosamyl muramyl tripeptide, GMDP, Icrocaptide (ITF-1697), Lucinactant, Lusupultide (BY-2001), NPC-567, NPY (24-36) (PTL-041120), or Secretin (human) (PGN-52) (R-52); and have utility in the treatment of respiratory conditions (e.g., alleviate one or more symptom(s) of a respiratory condition).

In certain embodiments, compounds of Formula (I) to (XII) are used to prepare aza-analogues of Casokefamide, CCK (25-33), Lagatide (BN-52080), Larazotide (AT-1001) (SPD-550), Linaclotide (MD-1100) (MM-41775), Nepadutant (MEN-11420), Nifalatide (BW942C), ROSE-010 (GTP-010) (LY-307161), Somatostatin, Somatostatin (D-Trp, D-Cys analog), SP-304 (Guanilib), Teduglutide (ALX-0600), Terlipressin, Triletide (Z-420) (ZAMI-420), Vapreotide (RC-160), ZP-1846, or ZP-1846; and have utility in the treatment of gastroenterologic disorders (e.g., alleviate one or more symptom(s) of a gastroenterologic disorder).

In certain embodiments, compounds of Formula (I) to (XII) are used to prepare aza-analogues of CJC-1295 (DAC: GRF), DG-3173 (PTR-3173), Dopastatin (BIM-23A760), EP-51216 (EP-51389), Examorelin (EP-23905) (MF-6003), GTP-200 (GTP-300), lpamorelin (NNC-26-0161), Iturelix (ORF-23541), KP-101 (GHRP-1), Lanreotide (ITM-014), Octreotide (SMS-201-995), Pasireotide (SOM-230), Pralmorelin, rGRF, SUN-11031, TH-9506, ZT0131, or vapreotide (RC-160); and have utility in the treatment of endocrinology disorders (e.g., alleviate one or more symptom(s) of an endocrinologic disorder).

Example 1

Activation of the Alkylthio Hydrazine Scaffolds

Template 21 was reacted with one equivalent of TCCA in dichloromethane (DCM) as a solvent, the reaction took place at room temperature and was monitored by TLC, we barely observed a change in $R_f$-values compare to the starting material on TLC (Scheme 6). Yet, the mass spectrometry analysis indicated the disappearance of the starting material.

Next, 2.0 equivalents of protected amino acid like glycine ethyl ester accompanied with four equivalents of diisopropylethylamine (DIPEA) was added. The corresponding substituted semicarbize 36 was observed as the only product on TLC. Later, the product was isolated with 94% yield (Scheme 6).

The same experiment was repeated without TCCA as a control experiment. Only the starting material was recovered, without any evidence of substitution at the thiocarbonyl moiety. When the control experiment was repeated with heat at 60° C., the amine attack favors the carbonyl moiety at the phthalimido-protecting group.

Next, the compatibility of the reaction conditions with different solvent systems was tested. The reaction performed well in chloroform, dichloromethane, acetone, and acetonitrile. We noticed that the reaction proceeded faster in acetonitrile and showed vigorous behavior in dimethylformamide (DMF), but gave an unclean profile on TLC. To understand the reaction mechanism, we opted to isolate the intermediate after the TCCA addition.

The reaction was repeated with two equivalents of TCCA to secure complete conversion of the starting material especially both intermediate, and the starting material showed the same $R_f$ values under different mobile phases. After evaporating the volatile solvent, the intermediate was purified using standard chromatography without the need to do any work-up. After purification, we collected needle-shaped crystals; the X-ray analysis proved the formation of hydrazine carbonyl chloride (chloroformate) intermediate. Surprisingly, this intermediate was stable under standard purification protocol (Scheme 6)

The scope of this reaction was then studies. First, a template having phthalimido protecting group was decorated with different side chains. The results are summarized in (Scheme 7):

Scheme 7: synthesis of novel substituted semicarbazides from the ATCHs (R and R' is each independently a side chain of an amino acid or an ester thereof)

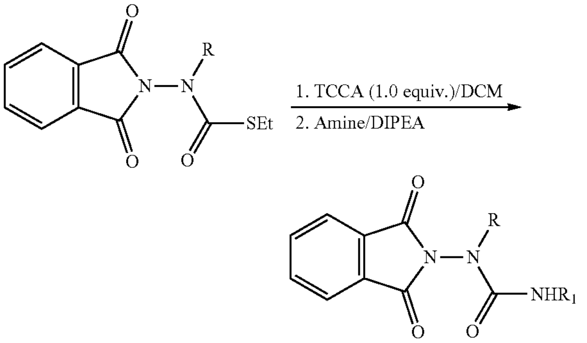

36

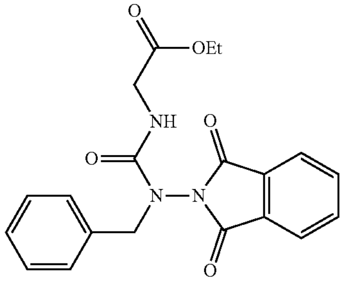

37

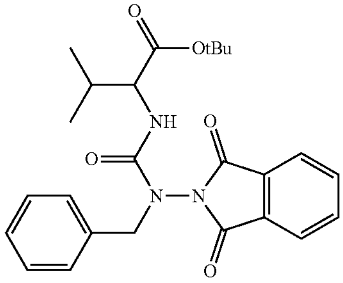

-continued
38
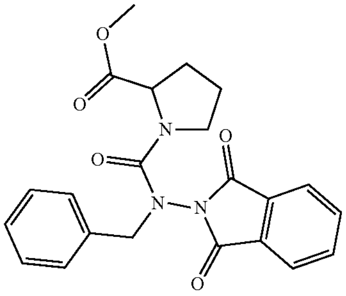
39
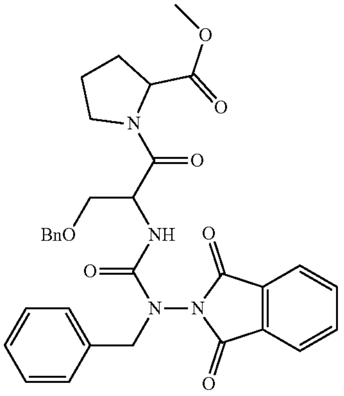
40
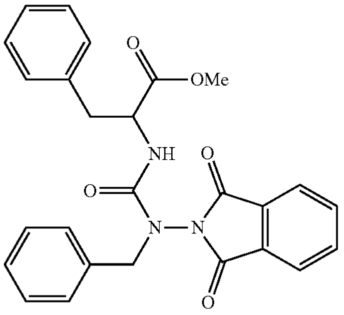
41
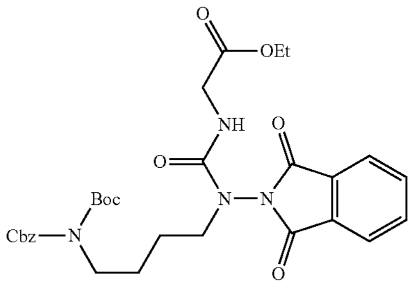
42
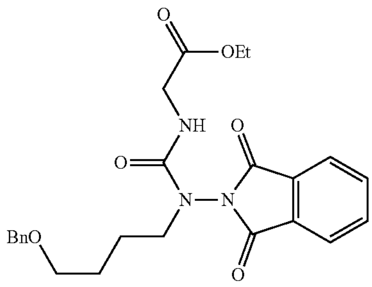
-continued
43
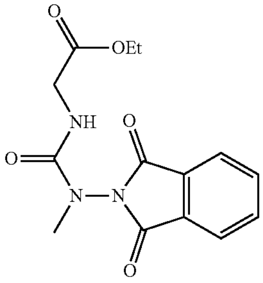
44
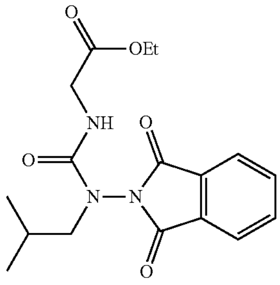
45
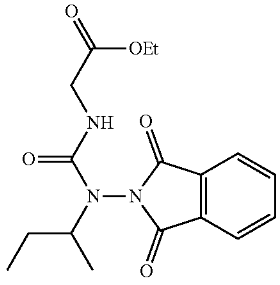
46
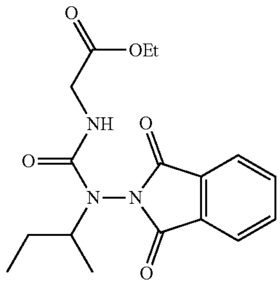
47
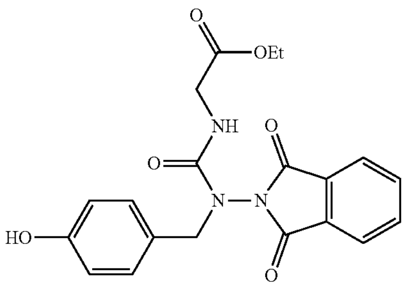

-continued

48

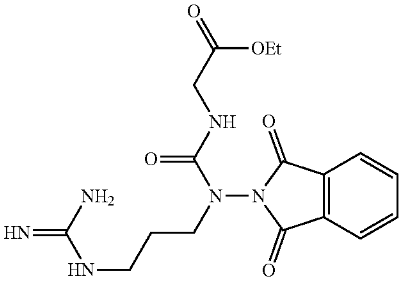

49

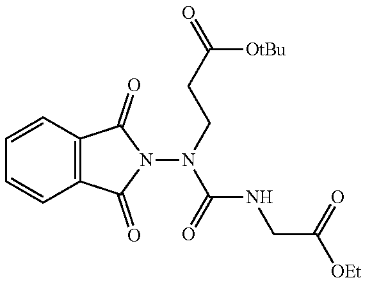

50

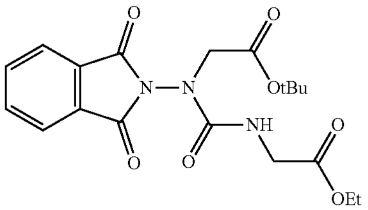

51

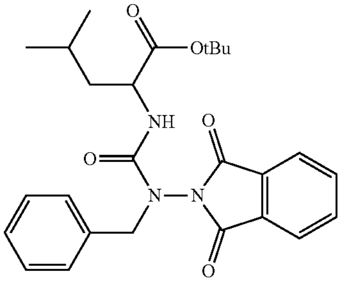

52

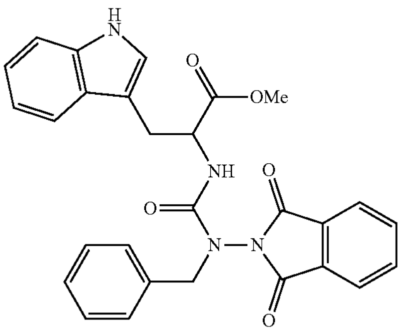

-continued

53

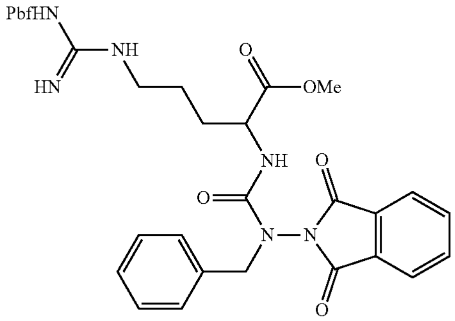

54

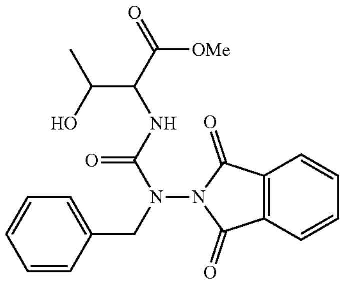

55

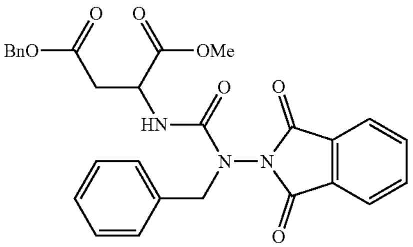

56

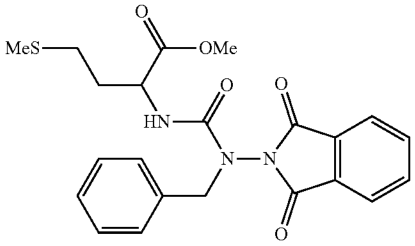

57

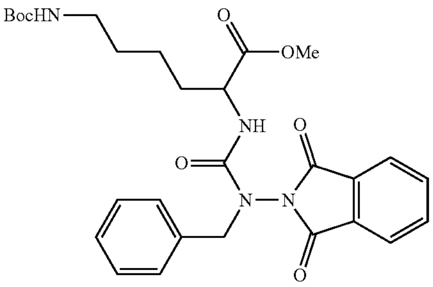

After optimizations, the reaction proceeded with one equivalent of TCCA and 1.5 equivalent of amine for coupling. The reaction tolerated most of the alkyl and aromatic side chains with no evidence of formation of chlorinated side products or any other side products.

One of the possible side products in this reaction is the formation of HCl gas or in solution, as a result, the treatment of ATCHs with TCCA in the first step is expected to be slightly acidic, to test the durability of acid reactive compounds with this protocol we chose acid labile moieties like the t-butyl esters 24 and 25. The corresponding semicarbazides 49 and 50 were isolated in good yields with no hydrolyzed esters as side products.

The side chains with amino group moieties might be reactive to the TCCA reagent. However, when the reaction performed on 29 and 30, the corresponding semicarbazides 41 and 48 respectively were collected in low to moderate yields. This might be because of the sensitivity of the Boc group and because of the reactivity of the NH carbamates to the chloronium species.

This protocol is proved to be also useful to prepare tripeptide segments. Compound 39 is a good example, which was made from ATCH 21 and protected serine-proline dipeptide.

To extend the scope of this reaction to cover more labile and delicate scaffolds like the Boc protected moieties, we determined to optimize the reaction condition by tuning the TCCA reactivity. Inventors found that the addition of one equivalent of tetrabutylammonium chloride reagent is capable of increasing the reaction rate; as a result, running the reaction at a lower temperature is conceivable. Inventors explored the new reaction conditions on the previous examples, and confirmed enhanced performance and higher yields for most of these depicted examples in scheme 7.

Encouraged with these findings, inventors tested the new class of Boc protected thiocarbazates 14 and 33. This reaction preceded smoothly with good to high yields (Scheme 8). Scaffolds 14 and 33 were treated separately with one equivalent of TCCA and one equivalent TBACl at 0° C., then was treated with valine t-butyl ester to give the corresponding semicarbazides with 68% and 89% yields respectively.

According to the literature, 51 can be made over four steps through reductive-amination and coupling using phosgene as the acylating agent. To validate our approach, we repeated the synthesis of scaffold 51 according to the literature. The samples prepared according to the literature and according to the invention were identical based on TLC, mass spec, and NMR.

Example 2

Functionalization of Thiocarbamates to Make Chiral Substituted Urease, Semicarbazides and Carbazides and Potential Targets to Build Variety of Peptidomimetics Having in hands a robust method to generate these reactive intermediates from acyl thiols using TCCA, like compounds mentioned in Example 1, the scope of the protocol was explored. Scheme 9 summarizes the results of the reactions that were performed:

Scheme 9

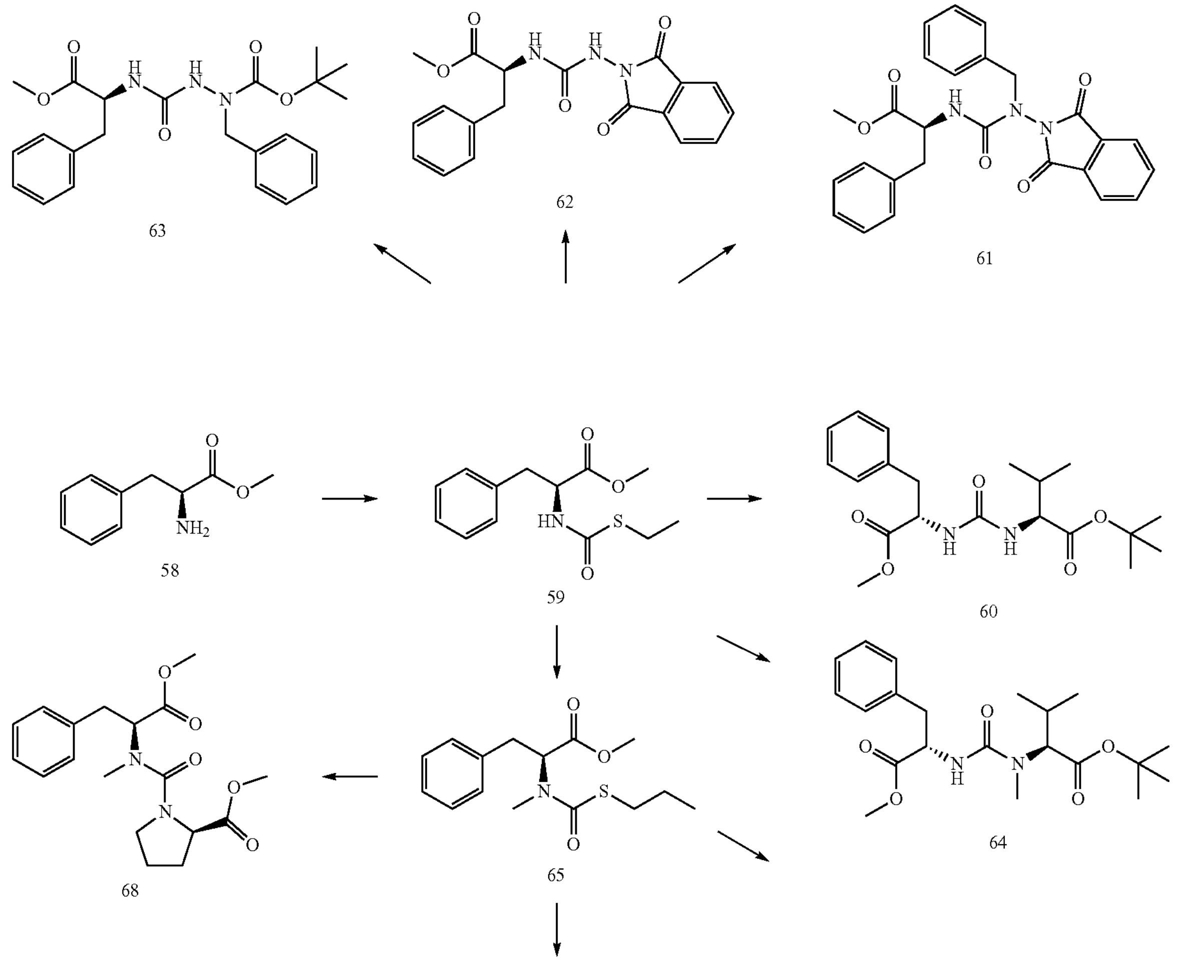

63
62
61
58
59
60
68
65
64

-continued

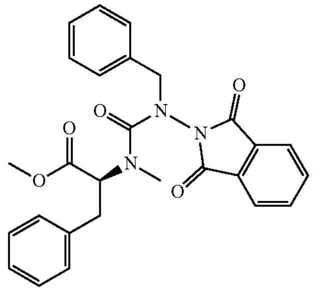

67

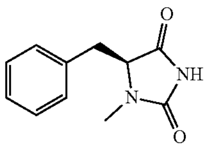

66

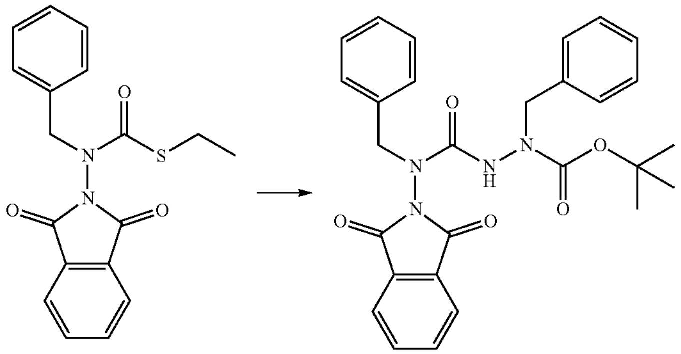

69

70

At the beginning, thiocarbamate 59 was build from the L-phenylalanine methyl ester 58 and the S-ethyl thiochloroformate in 90% yield, upon treatment 59 with TCCA/TBCl. The generation of the corresponding isocyanate, which can be isolated by simple filtration over a pad of silica to get rid of the other side products, was envisioned. The resulting isocyanate was treated in situ with L-valinate amino acid t-butyl ester. The resulted urea was then isolated in 67% without any epimerization. This experiment proved the efficacy of this technology to produce chiral substituted urease and to link peptides from the N-terminus.

Knowing that the hydrazines are inferior nucleophiles compared to typical amines, the coupling protocol was modified, e.g., by changing the base or the solvent. The isocyanate produced for thiocarbamate 59 was isolated by simple filtration over a pad of silica, after the complete evaporation of the organic volatiles; the crude isocyanate was dissolved in DMF and then treated with the appropriate hydrazine derivative in the presence of catalytic amount of DMAP. Semicarbazides 61, 62, and 63 were collected in 39%, 70%, and 89% yields, respectively.

It is important to note that the reaction rates for the formation of these semicarbazides are much slower than those of the reverse coupling order (see examples in Scheme 7) and that is because of the nature of the nucleophiles used. The reactions in scheme 9 are expected to be substrate dependents especially the formation of tetra-substituted derivatives like compounds 64-68. Reversing the addition order by installing the acylthiol on the hydrazine part followed by addition of more reactive amine may be one solution. However, this protocol may be further developed to achieve a global solution for the formation of the essential carbazides (e.g., 70), which may be uses as synthons for the creation of azatides peptidomimetics.

Example 3

Synthesis of Beta Peptides, and Other Bio Conjugates from Thioesters

The use of TCCA to generate, e.g., the reactive acyl chloride intermediates, which facilitate the formation of the peptide bond without the need for expensive peptide coupling reagents, was tested.

To test this idea, inventors prepared α-amino acid thioesters and tested the formation of the peptide bond under the protocol in Example 1. The reaction rate of activation of thioesters using TCCA was found to be much faster than that for activation of thiocarbamates and the semithiocarbazates. That is because of the neighboring nitrogen to the carbonyl system. The reaction proceeded smoothly even at subzero temperatures and without the need to add the TBACL. Careful NMR analysis confirmed the formation of acyl chloride as a reactive intermediate to form the peptide bond, and this finding was further confirmed by the formation of the acyl chloride using different pathway by reacting the amino acid with $SOCl_2$ as a control experiment. Regardless of the high yields of the formation of the dipeptide, the reaction suffers a complete epimerization of the alpha CH next to the thioester moiety.

Inventors repeated the experiment with beta amino acid thioesters to study the epimerization process and how to manage it in the light of understanding the bond dissociation energies for the alpha CH in amino acids and the captodative effect in stabilizing free radicals. The early results showed that the TCCA protocol does not induce epimerization in beta amino acids nor distant chiral centers other than the alpha CH. The results are summarized in Scheme 10:

Scheme 10: exploring the activation of thioesters using TCCA and the potential use in bioconjugation.
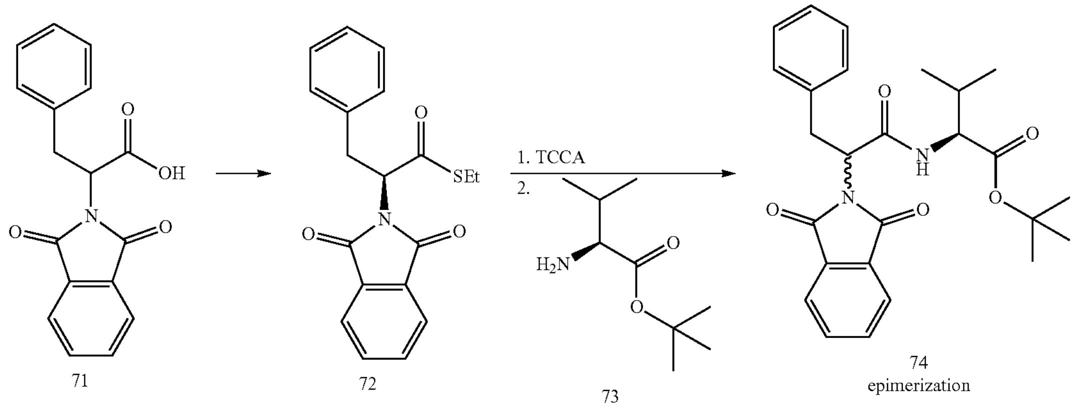
71 72 73
74
epimerization
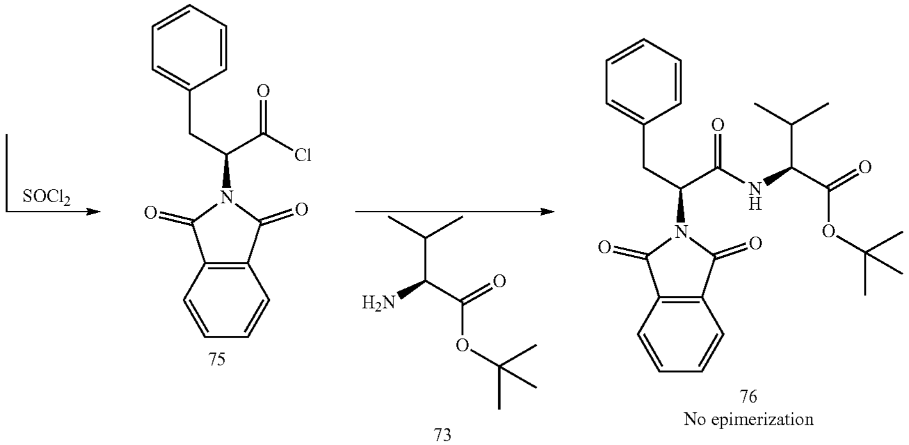
75 73
76
No epimerization
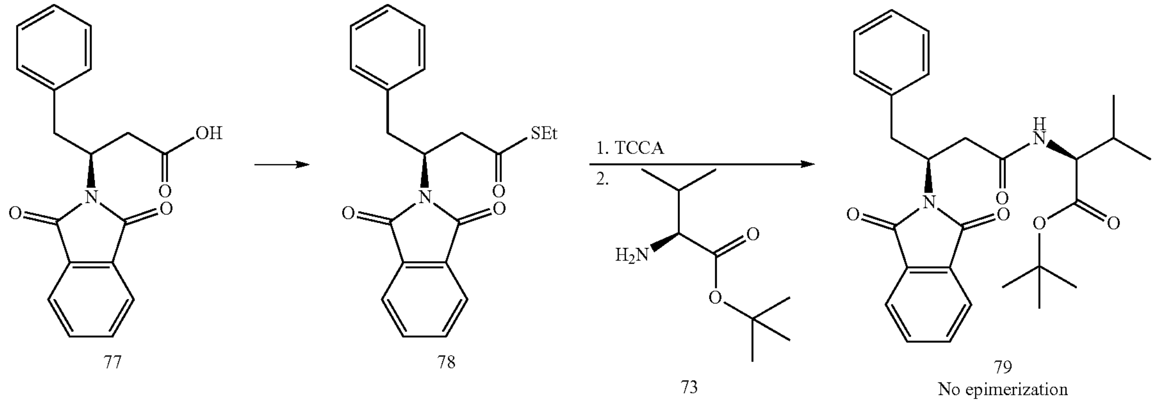
77 78 73
79
No epimerization -continued

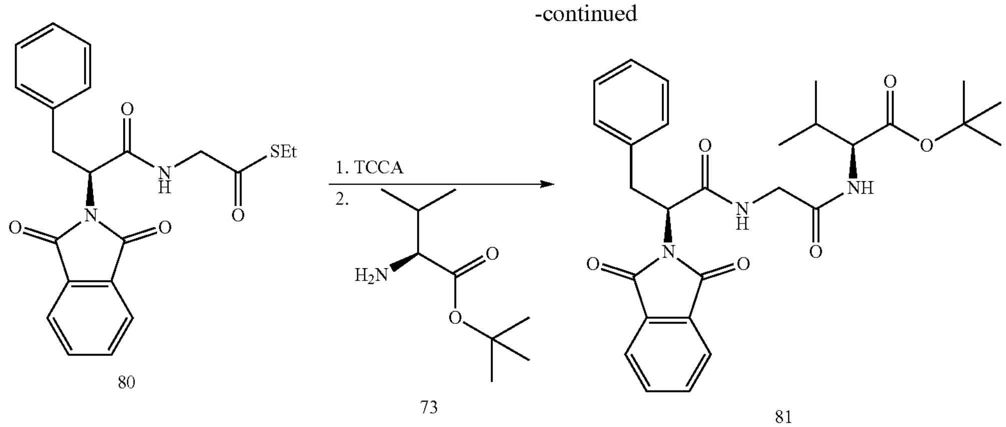

80

73

81

These results are encouraging and show promise in exploring this protocol and technology in designing bioconjugates that can be easily coupled to target proteins. The protocols could be used, e.g., in conjugating peptides, lipids, steroids or other active molecules that can be linked covalently to proteins.

Example 4

Unless otherwise mentioned, all starting materials were used directly from the supplier without further purifications; all reactions were carried out in oven-dried glassware using syringe and septa techniques, NMR spectra were collected on 500 or 600 MHz machines. Chemical shifts were recorded relative to the deuterated solvent peak or the internal standard tetramethylsilane (TMS) peak at (δ 0.00) and are reported in parts per million (ppm). Assignments for selected nuclei were determined from 1H COSY and HSQC experiments. Low-resolution mass spectrometry measurements were collected on LTQ mass spectrometer using Xcalibur software. X-ray analysis were acquired using Bruker X8 Kappa Apex II diffractometer using Mo Kα, radiation. The structure was solved using direct methods and standard difference map techniques, and was refined by full-matrix least-squares procedures on $F^2$ with SHELXTL (Version 2017/1). Thin-layer chromatography (TLC) was done on 0.25 mm thick-coated silica gel aluminum sheets. TLC plates were seen under UV light with short and long wavelengths, or were observed after iodine staining, or were visualized by heating the plates upon exposure to a solution of ammonium (VI) molybdate tetrahydrate and cerium (IV) sulfate tetrahydrate. In some cases $KMnO_4$ oxidation technique, and ninhydrine were also applied to observe the TLC plates. Flash column chromatography (FCC) was implemented using silica gel 60 (230-400 mesh) and employed a stepwise solvent polarity gradient, correlated with TLC mobility.

Procedure A: General Procedure to Prepare the Protected S-ethyl hydrazinecarbothioate

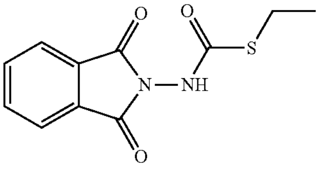 [SMILES: CCSC(=O)NN1C(=O)c2ccccc2C1=O]

To a solution of N-aminophthalimide (1000 mg, 6.1 mmol) in anhydrous dimethyl form amide (DMF) (10 mL) was added S-Ethyl chlorothioformate (600 uL, 6.1 mmol) and 4-dimethyl amino pyridine DMAP (150 mg, 0.61 mmol). The reaction mixture was stirred at room temperature for 2 hours, at which a copious white precipitate was observed. The reaction mixture was mixed with water (25 mL) and was extracted with EtOAc (25 mL×4). The combined organic layer was washed with brine (25 mL), dried over $Na_2SO_4$, filtered and evaporated under vacuum, and the residue was purified by FCC to give the protected S-ethyl hydrazine carbothioate

Procedure B: General Procedure to Synthesize the N-substituted S-Ethyl hydrazinecarbothioates

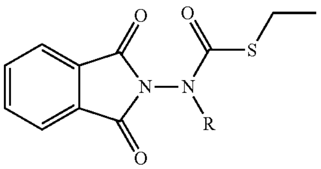

To a solution of S-ethyl (1,3-dioxoisoindolin-2-yl) carbamothioate from the previous step (1 mmol) in anhydrous THF (10 mL) was added $PPh_3$ (1.5 mmol) and alcohol (1.05 mmol). The stirred solution at 0° C. was treated with 40% DEAD solution in toluene drop-wise during 30 min (1.5 mmol). Then the reaction mixture was warmed up to r.t and stirred at this temperature for 2 h. the reaction was stopped by evaporating the excess volatiles in vacuum and the crude mixture was subjected to FCC to give the corresponding alkyl substituent.

a) S-ethyl benzyl(1,3-dioxoisoindolin-2-yl)carbamothioate

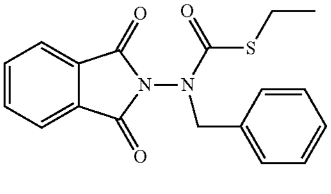 [SMILES: CCSC(=O)N(Cc1ccccc1)N1C(=O)c2ccccc2C1=O]

A solution of S-ethyl (1,3-dioxoisoindolin-2-yl) carbamothioate (83 mg, 0.332 mmol) in anhydrous THE (3.5 mL) was treated with benzyl alcohol (36 uL, 0.35 mmol), $PPh_3$ (130 mg, 0.5 mmol) and DEAD (215 uL, 0.5 mmol) according to above-mentioned procedure. After FCC purification the titled compound was isolated as white crystalline material with (98 mg, 87%).

$R_f$=(EtOAc/Hexane); $^1$HNMR (600 MHz, $CDCl_3$) δ 7.78-7.71 (m, 4H), 7.25-7.13 (m, 5H), 4.90 (s, 2H), 2.85 (m, 2H), 1.20 (m, 3H); $^{13}$C NMR (150 MHz, $CDCl_3$) δ 171.5, 164.9, 135.2, 134.0, 130.0, 128.7, 128.5, 124.3, 53.1, 25.2, 14.9.

b) S-ethyl sec-butyl(1,3-dioxoisoindolin-2-yl) carbamothioate

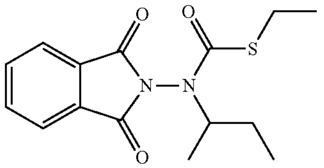 [SMILES: CCSC(=O)N(C(C)CC)N1C(=O)c2ccccc2C1=O]

A solution of S-ethyl (1,3-dioxoisoindolin-2-yl) carbamothioate (125 mg, 0.5 mmol) in anhydrous THE (2.0 mL) was treated with R-2-butanol (69 uL, 0.75 mmol), $PPh_3$ (197 mg, 0.75 mmol) and DEAD (330 uL, 0.75 mmol) according to above-mentioned procedure. After FCC purification the titled compound was isolated as white crystalline material with (120 mg, 78%). $R_f$=(EtOAc/Hexane); $^1$HNMR (500 MHz, Acetone $d_6$) δ 8.04 (m, 4H), 4.58 (q, J=6.8 Hz, 13.7 Hz, 1H), 2.83 (m, 2H), 1.77 (m, 1H), 1.47 (m, 1H), 1.24-1.18 (m, 6H), 1.02 (t, J=7.3 Hz, 3H); $^{13}$C NMR (125 MHz, Acetone $d_6$) δ 170.3, 166.4, 136.4, 130.7, 124.8, 58.3, 28.6, 25.0, 17.6, 15.4, 11.6.

c) tert-butyl N-(1,3-dioxoisoindolin-2-yl)-N-((ethylthio)carbonyl)glycinate (20180420-A659Y)

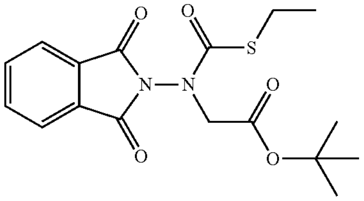 [SMILES: CCSC(=O)N(CC(=O)OC(C)(C)C)N1C(=O)c2ccccc2C1=O]

A solution of S-ethyl (1,3-dioxoisoindolin-2-yl) carbamothioate (125 mg, 0.5 mmol) in anhydrous THE (2.0 mL) was treated with tert-butyl 2-hydroxyacetate (99 mg, 0.75 mmol), $PPh_3$ (197 mg, 0.75 mmol) and DEAD (330 uL, 0.75 mmol) according to above-mentioned procedure. After FCC purification the titled compound was isolated as white crystalline material with (171 mg, 93%). $R_f$=(EtOAc/Hexane); $^1$HNMR (500 MHz, Acetone $d_6$) δ8.05 (m, 4H), 4.44 (s, 2H), 2.88 (m, 2H), 1.45 (s, 9H), 1.23 (m, 3H); $^{13}$C NMR (125 MHz, Acetone $d_6$) δ 171.6, 166.6, 164.8, 81, 61.7, 52.2, 28.1, 25.2, 15.3.

d) S-ethyl(4-(benzyloxy)butyl)(1,3-dioxoisoindolin-2-yl)carbamothioate (20180309-A643Y)

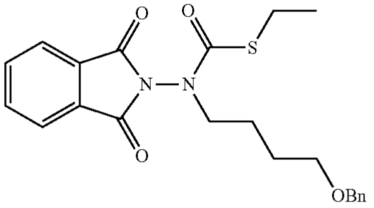 [SMILES: CCSC(=O)N(CCCCOCc1ccccc1)N1C(=O)c2ccccc2C1=O]

A solution of S-ethyl (1,3-dioxoisoindolin-2-yl) carbamothioate (50 mg, 0.2 mmol) in anhydrous THE (1.0 mL) was treated with 4-(benzyloxy) butan-1-ol (54 mg, 0.3 mmol), $PPh_3$ (78.6 mg, 0.3 mmol) and DEAD (132 uL, 0.3 mmol) according to above-mentioned procedure. After FCC purification the titled compound was isolated as white crystalline material with (70 mg, 85%). $R_f$=0.36 (20% EtOAc/Hexane); $^1$HNMR (600 MHz, Acetone $d_6$) δ7.87 (m, 4H), 7.17 (m, 5H), 4.33 (s, 2H), 3.70 (t, J=6.42 Hz, 2H), 3.36 (t, J=5.82 Hz, 2H), 2.69 (q, J=7.32 Hz, 2H), 1.58 (m, 4H), 1.06 (t, J=7.32 Hz, 3H); $^{13}$C NMR (150 MHz, Acetone $d_6$) δ171.1, 165.6, 140.1, 136.4, 130.7, 129.1, 128.3, 128.1, 127.9, 124.8, 73.2, 70.5, 50.3, 27.5, 25.5, 25.1, 15.4.

e) tert-butyl 3-((1,3-dioxoisoindolin-2-yl)((ethylthio)carbonyl)amino)propanoate (20180420-A654Y)

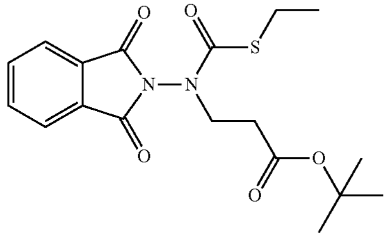 [SMILES: CCSC(=O)N(CCC(=O)OC(C)(C)C)N1C(=O)c2ccccc2C1=O]

A solution of S-ethyl (1,3-dioxoisoindolin-2-yl) carbamothioate (125 mg, 0.5 mmol) in anhydrous THE (2.0 mL) was treated with tert-butyl 3-hydroxypropanoate (110 uL, 0.75 mmol), $PPh_3$ (197 mg, 0.75 mmol) and DEAD (330 uL, 0.75 mmol) according to above-mentioned procedure. After FCC purification the titled compound was isolated as white crystalline material with (100 mg, 53%). $R_f$=(EtOAc/Hexane); $^1$HNMR (600 MHz, Acetone $d_6$) δ8.02 (m, 4H), 4.06 (t, J=6.7 Hz, 2H), 2.84 (m, 2H), 2.67 (t, J=6.7 Hz, 2H), 1.23 (s, 9H), 1.21 (t, J=7.3 Hz, 3H); $^{13}$C NMR (150 MHz, Acetone $d_6$) δ170.3, 164.5, 135.4, 129.8, 123.9, 80.2, 44.2, 33.7, 27.2, 24.2, 15.3.

f) S-ethyl (1,3-dioxoisoindolin-2-yl)(4-methoxybenzyl)carbamothioate (20180402-A644Y)

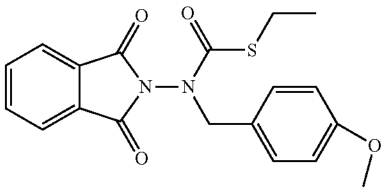 [SMILES: CCSC(=O)N(Cc1ccc(OC)cc1)N1C(=O)c2ccccc2C1=O]

A solution of S-ethyl (1,3-dioxoisoindolin-2-yl) carbamothioate (55 mg, 0.25 mmol) in anhydrous THF (1.0 mL) was treated with p-methoxy benzyl alcohol (45.5 mg, 0.33 mmol), $PPh_3$ (86.5 mg, 0.33 mmol) and DEAD (145 uL, 0.33 mmol) according to above-mentioned procedure. After FCC purification the titled compound was isolated as white crystalline material with (45 mg, 50%).

$R_f$=(EtOAc/Hexane); $^1$HNMR (600 MHz, Acetone $d_6$) δ7.82-7.78 (m, 4H), 7.15 (m, 2H), 6.68 (m, 2H), 4.75 (s, 2H), 3.60 (s, 3H), 2.72 (m, 2H), 1.07 (m, 3H); $^{13}$C NMR (150 MHz, Acetone $d_6$) δ171.7, 165.1, 160.6, 136.4, 135.1, 131.8, 130.4, 127.6, 124.8, 123.9, 114.5, 55.5, 53.3, 25.2, 15.4.

g) benzyl (tert-butoxycarbonyl)(4-((1,3-dioxoisoindolin-2-yl)((ethylthio)carbonyl)amino)butyl) carbamate (20180420-A651W)

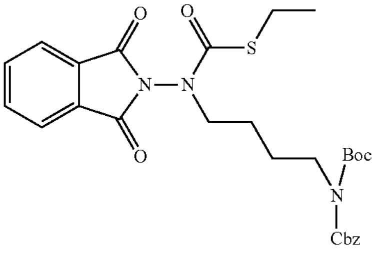 [SMILES: CCSC(=O)N(CCCCN(C(=O)OCc1ccccc1)C(=O)OC(C)(C)C)N1C(=O)c2ccccc2C1=O]

A solution of S-ethyl (1,3-dioxoisoindolin-2-yl) carbamothioate (55 mg, 0.22 mmol) in anhydrous THF (1.0 mL) was treated with benzyl (4-hydroxybutyl) carbamatel (98.12 mg, 0.44 mmol), $PPh_3$ (115 mg, 0.44 mmol) and DEAD (200 uL, 0.44 mmol) according to above-mentioned procedure. After FCC purification to afford a clear film, this material was dissolved in DMF and treated with Boc anhydride (100 uL) and DMAP (10 mg) and left stirring at rt for 1 hr. then, the reaction mixture was mixed with water and extracted with EtOAc (5 mL×3), the combined organic layer was washed with brine, dried over $Na_2SO_4$, filtered, and evaporated under vacuum, after standard FCC purification using 40% EtOAc/Hexane, the compound was isolated as clear wax with (88 mg, 72.1%). $R_f$=0.36 (20% EtOAc/Hexane); $^1$HNMR (600 MHz, Acetone $d_6$) δ8.02 (m, 4H), 7.46-7.32 (m, 5H), 5.19 (s, 2H), 3.83 (t, J=7.5 Hz, 2H), 3.68 (t, J=6.5 Hz, 2H), 2.84 (m, 2H), 1.72-165 (m, 4H), 1.44 (s, 9H), 1.21 (t, J=7.3 Hz, 3H); $^{13}$C NMR (150 MHz, Acetone $d_6$) δ171.1, 165.5, 154.7, 153.0, 137.2, 136.4, 135.2, 130.7, 129.4, 129.0, 124.9, 82.9, 68.7, 50.2, 46.6, 28.2, 26.9, 25.8, 25.2, 15.4.

h) S-ethyl (1,3-dioxoisoindolin-2-yl)(isobutyl) carbamothioate (A657)

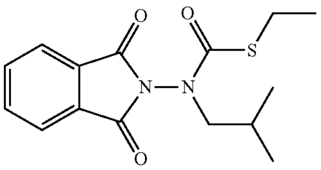 [SMILES: CCSC(=O)N(CC(C)C)N1C(=O)c2ccccc2C1=O]

A solution of S-ethyl (1,3-dioxoisoindolin-2-yl) carbamothioate (125 mg, 0.5 mmol) in anhydrous THF (2.0 mL) was treated with isobutanol (71 uL, 0.75 mmol), $PPh_3$ (197 mg, 0.75 mmol) and DEAD (330 uL, 0.75 mmol) according to above-mentioned procedure. After FCC purification the titled compound was isolated as white crystalline material with (150 mg, 98%). $R_f$=(EtOAc/Hexane); $^1$HNMR (600 MHz, Acetone $d_6$) δ.

i) The Boc Protected S-ethyl (1,3-dioxoisoindolin-2-yl)(3-(N,N',N"tri-boc-guanidinopropyl) carbamothioate (20180402-A660W)

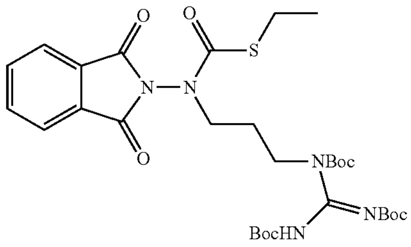

A solution of S-ethyl (1,3-dioxoisoindolin-2-yl) carbamothioate (125 mg, 0.5 mmol) in anhydrous THF (2.0 mL) was treated with propandiol (57 uL, 0.75 mmol), $PPh_3$ (197 mg, 0.75 mmol) and DEAD (330 uL, 0.75 mmol) according to above-mentioned procedure. The resulting alcohol was used in the next step after FCC purification. A solution of the alcohol from the previous step (70 mg, 0.227 mmol) in anhydrous THF (1.0 mL) was treated with N, N', N" tri-Boc-Guanidine (122 mg, 0.34 mmol), $PPh_3$ (89 mg, 0.34 mmol) and DEAD (150 uL, 0.34 mmol) according to above-mentioned. Upon purification using FCC protocol we collected (50 mg, 35%).

j) S-ethyl ((1H-indol-3-yl)methyl)(1,3-dioxoisoindolin-2-yl)carbamothioate (20181002-A648Y)

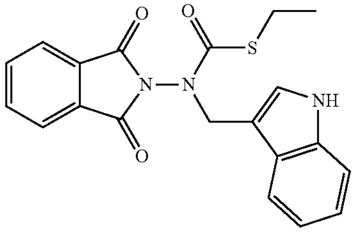 [SMILES: CCSC(=O)N(Cc1c[nH]c2ccccc12)N1C(=O)c2ccccc2C1=O]

A solution of S-ethyl (1,3-dioxoisoindolin-2-yl) carbamothioate (55 mg, 0.22 mmol) in anhydrous THE (1.0 mL) was treated with (1H-indol-3-yl) methanol (97 mg, 0.66 mmol), $PPh_3$ (173 mg, 0.66 mmol) and DEAD (290 uL, 0.66 mmol) according to above-mentioned procedure. After FCC purification the titled compound was isolated as yellow amorphous material with (75 mg, 90%). $R_f$=(EtOAc/Hexane); $^1$HNMR (600 MHz, Acetone $d_6$) δ 10.16 (bs, 1H), 7.93-7.85 (m, 4H), 7.62 (d, J=7.9 Hz, 1H), 7.33 (m, 2H), 7.07 (m, 1H), 6.99 (t, J=7.6 Hz, 1H), 5.17 (s, 2H), 2.90 (m, 2H), 1.24 (m, 3H); $^{13}$C NMR (150 MHz, Acetone $d_6$) δ 171, 164.1, 136.6, 135.3, 129.4, 126.1, 123.7, 121.5, 118.6, 111.3, 108.0, 44, 24, 15.

k) S-ethyl (1,3-dioxoisoindolin-2-yl)(2-(methylthio) ethyl)carbamothioate (20180309-A642Y)

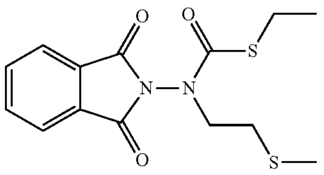 [SMILES: CCSC(=O)N(CCSC)N1C(=O)c2ccccc2C1=O]

A solution of S-ethyl (1,3-dioxoisoindolin-2-yl) carbamothioate (60 mg, 0.24 mmol) in anhydrous THE (1.0 mL) was treated with 2-(methylthio) ethan-1-ol (31 uL, 0.36 mmol), $PPh_3$ (94.3 mg, 0.36 mmol) and DEAD (160 uL, 0.36 mmol) according to above-mentioned procedure. After FCC purification the titled compound was isolated with (55 mg, 90%). $R_f$=(EtOAc/Hexane); $^1$HNMR (600 MHz, Acetone $d_6$) δ7.95 (bs, 4H), 3.92 (t, J=7.8 Hz, 2H), 2.81-2.71 (m, 4H), 2.00 (s, 3H), 1.47 (t, J=7.32 Hz, 3H); $^{13}$C NMR (150 MHz, Acetone $d_6$) δ 171.1, 165.5, 136.3, 130.8, 124.8, 49.9, 31.9, 25.1, 15.3, 15.2.

l) S-ethyl (1,3-dioxoisoindolin-2-yl)(isopropyl) carbamothioate (A648W)

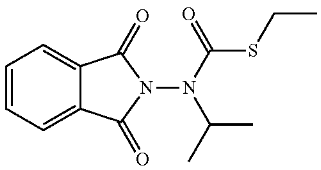 [SMILES: CCSC(=O)N(C(C)C)N1C(=O)c2ccccc2C1=O]

A solution of S-ethyl (1,3-dioxoisoindolin-2-yl) carbamothioate (55 mg, 0.22 mmol) in anhydrous THE (1.0 mL) was treated with 2-propanol (35 uL, 0.44 mmol), $PPh_3$ (115 mg, 0.44 mmol) and DEAD (200 uL, 0.44 mmol) according to above-mentioned procedure. After FCC purification the titled compound was isolated with (55 mg, 86%). $R_f$=(EtOAc/Hexane); $^1$HNMR (600 MHz, Acetone $d_6$) δ.

m) S-ethyl (1,3-dioxoisoindolin-2-yl)(methyl)carbamothioate (A652W)

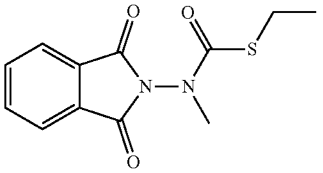 [SMILES: CCSC(=O)N(C)N1C(=O)c2ccccc2C1=O]

A solution of S-ethyl (1,3-dioxoisoindolin-2-yl) carbamothioate (125 mg, 0.5 mmol) in anhydrous THE (2.0 mL) was treated with methanol (24 uL, 0.75 mmol), $PPh_3$ (197 mg, 0.75 mmol) and DEAD (326 uL, 0.75 mmol) according to above-mentioned procedure. After FCC purification the titled compound was isolated with (140 mg, 99%). $R_f$= (EtOAc/Hexane); $^1$HNMR (600 MHz, Acetone $d_6$) δ.

Procedure C: Procedure to Prepare the Aza-Serine Amine-Acid Analogs (this Procedure can be Applied to the Reaction of the Hydrazones with Aldehydes in General)

((1,3-dioxoisoindolin-2-yl)((ethylthio) carbonyl) amino)methyl acetate (20180420-A645W-OAc)

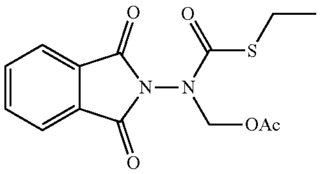 [SMILES: CCSC(=O)N(COC(C)=O)N1C(=O)c2ccccc2C1=O]

A solution of S-ethyl (1,3-dioxoisoindolin-2-yl) carbamothioate (55 mg, 0.22 mmol) in anhydrous Toluene (2.0 mL) was treated with paraformaldehyde (60 mg, 2.2 mmol), the reaction mixture was heated at 80° C. until the disappearance of the starting material. The isolated crude was dissolved in EtOAc and treated with $Ac_2O$ and DMAP. After FCC purification, the titled compound was isolated as clear crystals. $R_f$=(EtOAc/Hexane); $^1$HNMR (500 MHz, Acetone $d_6$) δ7.91 (m, 4H), 5.53 (s, 2H), 2.74 (q, J=14.4, 7.1 Hz, 2H), 1.91 (s, 3H), 1.09 (t, J=7.25, 3H); $^{13}$C NMR (125 MHz, Acetone $d_6$) δ171.7, 171.3, 164.9, 136.6, 130.4, 125.1, 69.7, 25.3, 20.6, 15.1.

Procedure D: General Procedure to Prepare the tert-butyl 2-((ethylthio) carbonyl)hydrazine-1-carboxylate

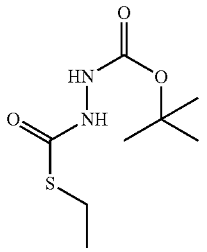

To a solution of tert-butyl carbazate (1320 mg, 10.0 mmol) in anhydrous diethyl ether (40 mL) was added S-Ethyl chlorothioformate (1050 uL, 10.0 mmol) and pyridine (890 uL, 11.2 mmol). The reaction mixture was stirred at r.t for 45 min, at which a copious white precipitate was observed. The reaction mixture was mixed with water (25 mL) and was extracted with EtOAc (25 mL×4). The combined organic layer was washed with brine (25 mL), dried over $Na_2SO_4$, filtered and evaporated under vacuum, and the residue was purified by FCC to give the protected S-ethyl hydrazine carbothioate tert-butyl 2-benzyl-2-((ethylthio)carbonyl)hydrazine-1-carboxylate

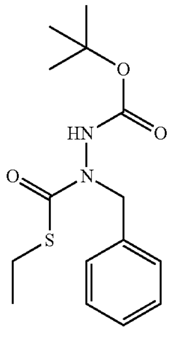

To a solution of the Boc-protected S-ethyl hydrazine carbothioate (200 mg, 0.9 mmol) in anhydrous THE (2.0 mL) was added $PPh_3$ (357 mg, 1.36 mmol) and benzyl alcohol (107 uL, 0.99 mmol) and DEAD (616 uL, 1.36 mmol) according to above-mentioned procedure. The residue was purified by FCC to give the titled compound as colorless crystals (214 mg, 69%). $R_f$=(EtOAc/Hexane); $^1$HNMR (600 MHz, Acetone $d_6$) δ8.60 (bs, 1H), 7.32 (m, 5H), 4.76 (ABq, J=12.2 Hz, Δδ=0.99 ppm, 2H), 2.83 (m, 2H), 1.25 (t, J=7.32 Hz, 3H); $^{13}$C NMR (150 MHz, Acetone $d_6$) δ20181002-A738).

Procedure E: Procedure to Prepare the Aza-Proline Analog (this Procedure is Applicable to the Synthesis of Alkyl Substituted Hydrazine Carbamates Using NAH and Alkyl Halides)

tert-butyl 2-((ethylthio)carbonyl)pyrazolidine-1-carboxylate

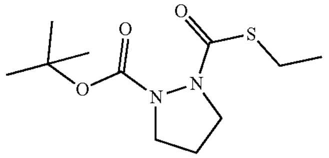 [SMILES: CCSC(=O)N1CCCN1C(=O)OC(C)(C)C]

To a solution of Boc-protected S-ethyl hydrazine carbothioate (210 mg, 0.95 mmol) in anhydrous DMF (5.0 mL) was added NaH (84.0 mg, 2.1 mmol). The reaction mixture was stirred at 0° C. for 15 min, at which diiodopropane (110 uL, 0.95 mmol) solution in DMF (1.0 mL) was added drop-wise. The reaction mixture was stirred at room temperature for 16 hours. Upon completion, the reaction was treated with water (25 mL) and was extracted with EtOAc (25 mL×4). The combined organic layer was washed with brine (25 mL), dried over $Na_2SO_4$, filtered and evaporated under vacuum, and the residue was purified by FCC to give the titled compound with (85 mg, 34%). $^1$HNMR (500 MHz, Acetone $d_6$) δ4.00 (m, 2H), 3.15 (m, 1H), 3.04 (m, 1H), 2.88 (m, 2H), 2.06 (m, 2H), 1.46 (s, 9H), 1.23 (t, J=7.32 Hz, 3H); $^{13}$C NMR (125 MHz, Acetone $d_6$) δ175.2, 156.9, 82.6, 46.8, 46.2, 28.3, 25.7, 24.4, 15.2. (20180830-A733), Procedure F: General Procedure to Prepare the Substituted Semicarbazides

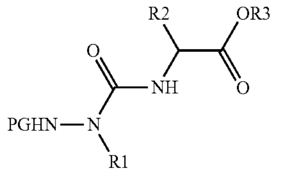

To a solution of the thiocarbamate (0.1 mmol) in DCM (2.0 mL) was added TBACl (0.1 mmol) and TCCA (0.1 mmol). The reaction mixture was stirred at r.t for 15 min then cooled down to 0° C. using ice bath. The ice-cold reaction mixture was added amine (0.15 mmol) and diisopropylethylamine (DIPEA) (0.4 mmol). The reaction was left stirring at room temperature for another 30 min or until the disappearance of the starting materials. Upon completion, the reaction mixture was treated with saturated solution of sodium thiosulfate and stirred for 15-30 min, and then the aqueous layer was extracted with organic solvent (×3 times). The combined organic layers was washed with brine, dried over $Na_2SO_4$, filtered, and evaporated under vacuum. The resulting residue was subjected to standard FCC using EtOAc/Hexane with gradient increase of polarity. The titled compounds were characterized by mass spectroscopy and NMR.

a) tert-butyl (benzyl(1,3-dioxoisoindolin-2-yl)carbamoyl)valinate

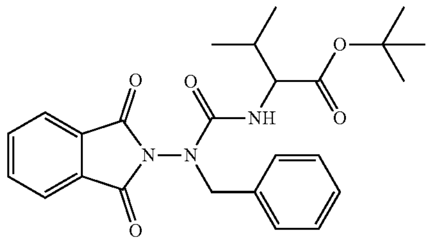 [SMILES: CC(C)C(NC(=O)N(Cc1ccccc1)N1C(=O)c2ccccc2C1=O)C(=O)OC(C)(C)C]

To a solution of the thiocarbamate (34 mg, 0.1 mmol) in DCM (1.0 mL) was added TBACl (28 mg, 0.1 mmol) and TCCA (23 mg, 0.1 mmol). The reaction mixture was stirred at room temperature for 15 min then cooled down to 0° C. using ice bath. The ice-cold reaction mixture was added amine (0.15 mmol) and diisopropylethylamine (DIPEA) (0.4 mmol). The reaction mixture was processed according to procedure F to give the titled compound with (43 mg, 95%). $^1$HNMR (500 MHz, Acetone $d_6$) δ7.85 (m, 4H), 7.27 (m, 2H), 7.23 (m, 3H), 6.42 (d, J=10.0 Hz, 1H), 4.93 (s, 2H), 4.19 (q, J=5.0, 10 Hz, 1H), 1.98 (m, 1H), 1.44 (s, 9H), 0.91

(d, J=5.0 Hz, 3H), 0.88 (d, J=5.0 Hz, 3H); $^{13}$C NMR (125 MHz, Acetone $d_6$) δ171.7, 166.1, 157.2, 137.2, 135.6, 131.3, 131.1, 129.9, 129.0, 128.5, 124.2, 81.5, 60.8, 53.5, 31.6, 28.2, 19.51, 18.6. (20181011-A758).

b) methyl (benzyl(1,3-dioxoisoindolin-2-yl)carbamoyl)prolinate (20180226-A635W) in Note Book is A638Y

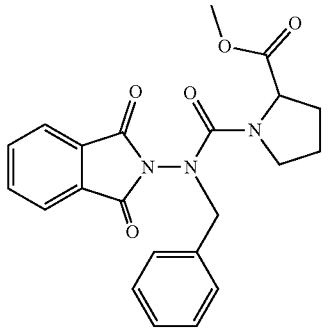 [SMILES: COC(=O)C1CCCN1C(=O)N(Cc1ccccc1)N1C(=O)c2ccccc2C1=O]

To a solution of the thiocarbamate (15 mg, 0.044 mmol) in DCM (1.0 mL) was added TBACl (12 mg, 0.095 mmol) and TCCA (10 mg, 0.095 mmol). The reaction mixture was stirred at r.t for 15 min then cooled down to 0° C. using ice bath. The ice-cold reaction mixture was added amine (9.0 mg, 0.066 mmol) and diisopropylethylamine (DIPEA) (32 uL, 0.176 mmol). The reaction mixture was processed according to procedure F to give the titled compound with (15 mg, 84%). $^{1}$HNMR (600 MHz, $CDCl_3$) δ7.68 (m, 4H), 7.29 (m, 2H), 7.14 (m, 3H), 4.75 (ABq, J=14.2 Hz, Δδ=0.18 ppm, 2H), 4.42 (q, J=7.9, 4.9 Hz, 1H), 3.55 (s, 3H), 3.30-3.21 (m, 2H), 2.07 (m, 1H), 1.85 (m, 1H), 1.75 (m, 2H); $^{13}$C NMR (150 MHz, $CDCl_3$) δ173.0, 165.4, 165.1, 158.4, 135.0, 134.9, 130.0, 129.4, 128.5, 128.2, 124.1, 124.0, 61.0, 54.5, 52.3, 48.4, 29.6, 25.1.

c) methyl O-benzyl-N-(benzyl(1,3-dioxoisoindolin-2-yl)carbamoyl)serylprolinate. (20180510-A666W)

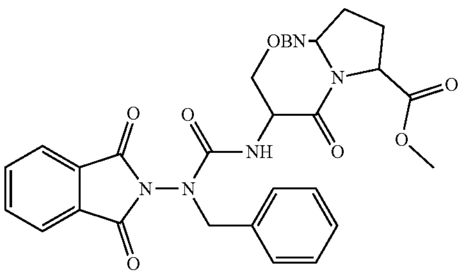

To a solution of the thiocarbamate (34 mg, 0.1 mmol) in DCM (1.0 mL) was added TBACl (28 mg, 0.1 mmol) and TCCA (23 mg, 0.1 mmol). The reaction mixture was stirred at room temperature for 15 min then cooled down to 0° C. using ice bath. The ice-cold reaction mixture was added amine (0.15 mmol) and diisopropylethylamine (DIPEA) (0.4 mmol). The reaction mixture was processed according to procedure F to give the titled compound with (mg, %). $^{1}$HNMR (600 MHz, Acetone $d_6$) δ7.74-7.69 (m, 4H), 7.28 7.05 (m, 10H), 6.60 (bd, J=8.04 Hz, 1H), 4.81-4.74 (m, 3H), 4.39 (ABq, J=12.06 Hz, Δδ=0.02 ppm, 2H), 4.20 (q, J=8.6, 4.6 Hz, 1H), 3.69 (m, 1H), 3.61 (m, 2H), 3.48 (m, 2H), 3.46 (s, 3H), 3.44 (m, 2H), 2.09 (m, 2H), 1.88 (m, 2H), 1.76 (m, 1H); $^{13}$C NMR (150 MHz, Acetone $d_6$) δ173.1, 169.6, 166.1, 166.0, 157.0, 139.7, 137.2, 135.7, 131.2, 130.1, 129.2, 129.1, 128.5, 128.4, 128.2, 124.3, 124.3, 73.8, 73.6, 75.5, 72.0, 70.9, 62.0, 59.9, 53.4, 53.3, 53.0, 52.7, 52.1, 47.7, 47.1, 44.0, 25.6.

d) ethyl (benzyl(1,3-dioxoisoindolin-2-yl)carbamoyl)glycinate (20180226-A639W)

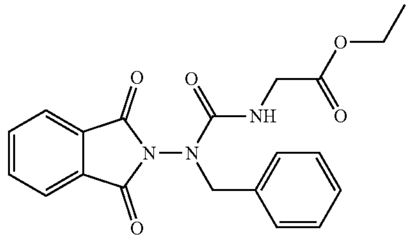 [SMILES: CCOC(=O)CNC(=O)N(Cc1ccccc1)N1C(=O)c2ccccc2C1=O]

The reaction mixture was processed according to procedure F on 0.025 mmol scale. This reaction gave the titled compound with (9.0 mg, 94%). $^{1}$HNMR (600 MHz, $CDCl_3$) δ 7.83 (m, 2H), 7.76 (m, 2H), 7.28 (m, 2H), 7.24 (m, 4H), 5.29 (t, J=4.68 Hz, 1H), 4.92 (s, 2H), 4.16 (q, J=7.14 Hz, 2H), 4.02 (d, J=4.92 Hz, 2H), 1.26 (t, J=7.14 Hz, 3H).

e) protected Aza-Lysine-Glycine-ethyl ester dipeptide (20180420-A651Y)

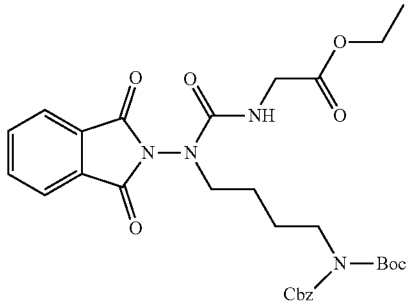 [SMILES: CCOC(=O)CNC(=O)N(CCCCN(C(=O)OCc1ccccc1)C(=O)OC(C)(C)C)N1C(=O)c2ccccc2C1=O]

The reaction mixture was processed according to procedure F on 0.025 mmol scale. This reaction gave the titled compound with (%). $^{1}$HNMR (600 MHz, $CDCl_3$) δ 7.79 (m, 4H), 7.31-7.19 (m, 5H), 6.86 (m, 1H), 5.03 (s, 2H), 3.94 (q, J=7.15 Hz, 2H), 3.67 (m, 2H), 3.61 (t, J=7.25 Hz, 2H), 3.51 (t, J=6.7 Hz, 2H), 1.92-145 (m, 4H), 1.28 (s, 9H), 1.07 (t, J=7.55 Hz, 3H); $^{13}$C NMR (125 MHz, Acetone $d_6$) δ 170.8, 166.4, 157.3, 154.7, 152.9, 137.1, 135.7, 131.5, 129.3, 129.0, 124.3, 82.8, 68.7, 61.2, 49.3, 46.7, 42.9, 28.9, 26.9, 26.1, 14.5.

f) tert-butyl N-(1,3-dioxoisoindolin-2-yl)-N-((2-ethoxy-2-oxoethyl)carbamoyl)glycinate (20180420-A660Y)

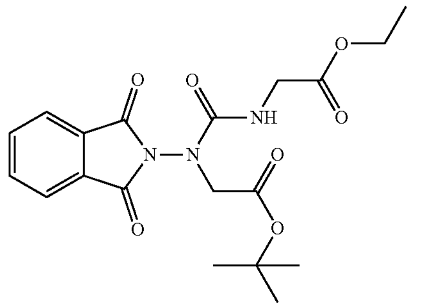 [SMILES: CCOC(=O)CNC(=O)N(CC(=O)OC(C)(C)C)N1C(=O)c2ccccc2C1=O]

The reaction mixture was processed according to procedure F on 0.025 mmol scale. This reaction gave the titled compound with (%). $^1$HNMR (600 MHz, $CDCl_3$) δ 7.85-7.74 (m, 4H), 5.68 (bs, 1H), 4.28 (s, 2H), 4.10 (q, J=7.14 Hz, 2H), 3.93 (d, J=4.9 Hz, 2H), 1.38 (s, 9H), 1.88 (t, J=7.2 Hz, 3H); $^{13}$C NMR (150 MHz, $CDCl_3$) δ 167.6, 165.0, 155.7, 135.2, 130.0, 124.4, 82.9, 61.8, 51.8, 43.0, 28.1, 14.3.

g) Ethyl ((4-(benzyloxy)butyl)(1,3-dioxoisoindolin-2-yl)carbamoyl)glycinate (20180309-A644W)

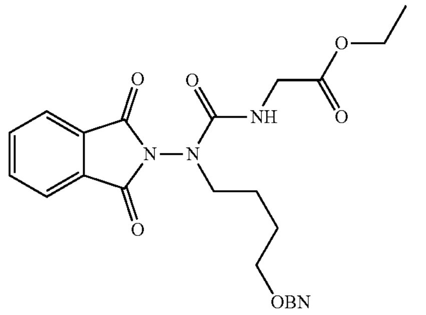

The reaction mixture was processed according to procedure F on 0.025 mmol scale. This reaction gave the titled compound with (%). $^1$HNMR (600 MHz, $CDCl_3$) δ 7.81 (m, 2H), 7.72 (m, 2H), 7.24 (m, 5H), 5.63 (bs, 1H), 4.41 (s, 2H), 4.11 (t, 2H), 3.71 (m, 4H), 3.51 (t, J=5.9 Hz, 2H), 1.75 (m, 2H), 1.62 (m, 2H), 1.18 (t, J=7.3 Hz, 3H); $^{13}$C NMR (150 MHz, $CDCl_3$) δ170.4, 165.9, 156.1, 138.3, 135.0, 130.1, 128.7, 128.0, 127.9, 124.2, 73.5, 61.5, 49.7, 42.7, 26.0, 14.3.

h) tert-butyl 2-benzyl-2-((1-(tert-butoxy)-3-methyl-1-oxobutan-2-yl)carbamoyl)hydrazine-1-carboxylate. (2018002-A750)

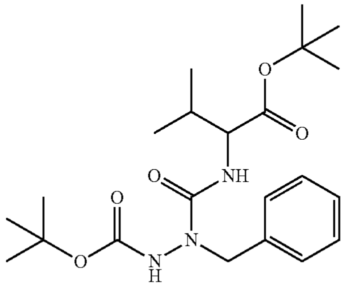 [SMILES: CC(C)C(NC(=O)N(Cc1ccccc1)NC(=O)OC(C)(C)C)C(=O)OC(C)(C)C]

This compound was prepared according to procedure F on 0.12 mmol scale. This reaction gave the titled compound with (45 mg, 89%). $^1$HNMR (600 MHz, Acetone $d_6$) δ 7.3× (m, 5H), 6.05 (m, 1H), 4.24 (m, 1H), 2.89 (m, 2H), 2.06 (m, 1H), 1.53 (m, 18H), 0.90 (d, 3H), 0.88 (d, 3H.

f) tert-butyl 2-((1-(tert-butoxy)-3-methyl-1-oxobutan-2-yl)carbamoyl)pyrazolidine-1-carboxylate. (20181002-A752)

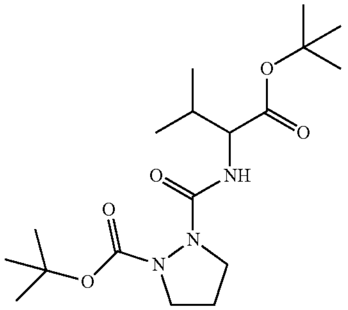

This compound was prepared according to procedure F on 0.058 mmol scale. This reaction gave the titled compound with (15 mg, 69%). $^1$HNMR (600 MHz, Acetone $d_6$) δ 6.0× (d, 1H), 4.0× (q, 1H), 3.7× (m, 2H), 3.0× (m, 2H), 2.0× (m, 1H), 2.06 (m, 1H), 1.93 (m, 2H), 1.28 (m, 18H), 0.9× (d, 3H), 0.7× (d, 3H);

j) methyl (benzyl(1,3-dioxoisoindolin-2-yl)carbamoyl)phenylalaninate (20181101-A763)

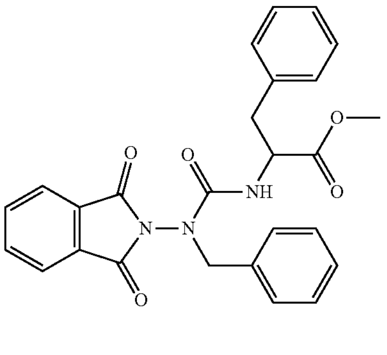 [SMILES: COC(=O)C(Cc1ccccc1)NC(=O)N(Cc1ccccc1)N1C(=O)c2ccccc2C1=O]

This compound was prepared according to procedure F on 0.095 mmol scale. This reaction gave the titled compound with (35 mg, 82%). $^1$HNMR (600 MHz, Acetone $d_6$) δ 7.73-7.769 (m, 4H), 7.23-7.04 (m, 10H), 6.66 (m, 1H), 4.72 (ABq, J=14.8 Hz, 2H), 4.44 (m, 1H), 3.48 (m, 3H), 2.87 (dd, J=13.7, 5.8 Hz, 1H), 2.2.75 (m, 1H); $^{13}$C NMR (150 MHz, Acetone $d_6$) δ 173.0, 166.0, 165.9, 157.0, 138.2, 137.1, 135.7, 131.2, 130.3, 130.0, 129.2, 129.0, 128.5, 127.5, 124.3, 124.2, 56.4, 53.3, 52.2, 38.3.

k) methyl (benzyl(1,3-dioxoisoindolin-2-yl)carbamoyl)tryptophanate (20181101-A767)

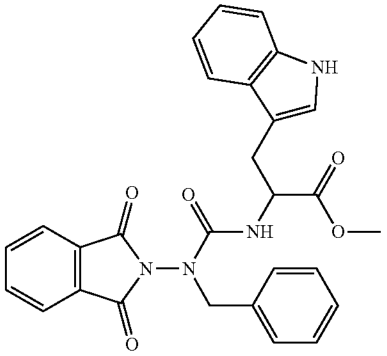 [SMILES: COC(=O)C(Cc1c[nH]c2ccccc12)NC(=O)N(Cc1ccccc1)N1C(=O)c2ccccc2C1=O]

This compound was prepared according to procedure F on 0.1 mmol scale. This reaction gave the titled compound with (48 mg, 87%). $^1$HNMR (500 MHz, Acetone $d_6$) δ 10.05 (bs, 1H), 7.88-7.81 (m, 4H), 7.51 (d, J=7.9 Hz, 1H), 7.34 (m, 3H), 7.21 (m, 3H), 7.11 (m, 1H), 7.04 (t, J=7.15 Hz, 1H), 6.96 (t, J=7.3, 1H), 6.74 (m, 1H), 4.86 (ABq, J=14.8 Hz, 2H), 4.65 (m, 1H), 3.60 (s, 3H), 3.19 (m, 1H), 3.05 (m, 1H); $^{13}$C NMR (125 MHz, Acetone $d_6$) δ 173.4, 166.0, 157.1, 137.5, 137.1, 135.7, 131.1, 130.0, 129.0, 128.5, 124.6, 124.3, 124.2, 122.2, 119.7, 119.0, 112.2, 110.8, 55.8, 53.3, 52.5, 28.2.

l) methyl N$^2$-(benzyl(1,3-dioxoisoindolin-2-yl)carbamoyl)-N-((2,2,4,6,7-pentamethyl-2,3-dihydrobenzofuran-5-yl)sulfonyl)argininate. (20181101-A768)

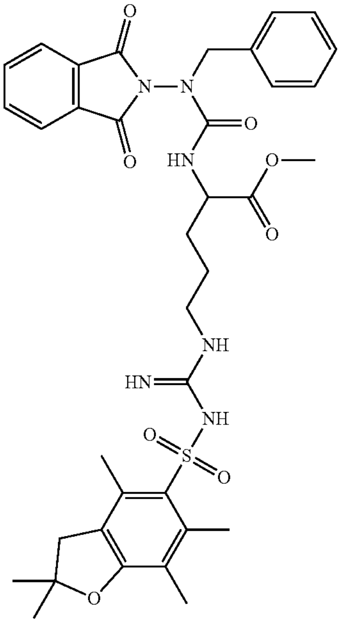 [SMILES: COC(=O)C(CCCNC(=N)NS(=O)(=O)c1c(C)c(C)c2c(c1C)CC(C)(C)O2)NC(=O)N(Cc1ccccc1)N1C(=O)c2ccccc2C1=O]

This compound was prepared according to procedure F on 0.1 mmol scale. This reaction gave the titled compound with (52 mg, 71%). $^1$HNMR (600 MHz, Acetone $d_6$) δ 7.85-7.81 (m, 4H), 7.37 (d, J=6.8 Hz, 2H), 7.24-7.19 (m, 3H), 6.95 (m, 1H), 6.47 (m, 2H), 4.88 (ABq, J=14.6 Hz, 2H), 4.36 (m, 1H), 3.62 (s, 3H), 3.17 (m, 2H), 2.99 (s, 6H), 2.82 (s, 3H), 2.56 (s, 3H), 2.49 (s, 3H) 1.76 (m, 1H), (1.58-1.1.48 (m, 3H), 1.44 (s, 6H); $^{13}$C NMR (150 MHz, Acetone $d_6$) δ 173.5, 166.1, 165.9, 159.0, 157.4, 138.8, 137.1, 135.7, 132.9, 131.3, 131.2, 129.0, 128.5, 125.4, 124.3, 124.2, 117.5, 87.0, 53.2, 52.3, 43.7, 19.5, 18.2, 12.6.

m) tert-butyl (benzyl(1,3-dioxoisoindolin-2-yl)carbamoyl)leucinate (20181120-A769)

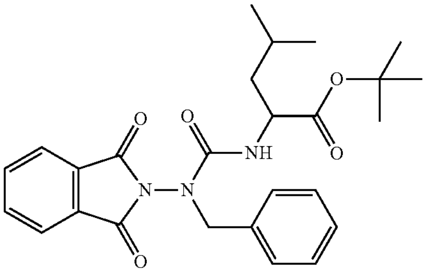 [SMILES: CC(C)CC(NC(=O)N(Cc1ccccc1)N1C(=O)c2ccccc2C1=O)C(=O)OC(C)(C)C]

This compound was prepared according to procedure F on 0.1 mmol scale. This reaction gave the titled compound with (42 mg, 90.3%). $^1$HNMR (600 MHz, Acetone $d_6$) δ 7.85-7.81 (m, 4H), 7.39-7.18 (m, 5H), 6.74 (d, J=8.16 Hz, 1H), 4.90 (s, 2H), 4.32 (m, 1H), 1.72 (m, 1H), 1.43 (m, 11H), 0.89 (d, J=6.54 Hz, 3H), 0.85 (d, J=6.66 Hz, 3H); $^{13}$C NMR (150 MHz, Acetone $d_6$) δ 172.9, 166.1, 166.0, 157.3, 137.3, 135.6, 131.3, 130.1, 129.0, 128.4, 124.2, 124.2, 81.2, 53.9, 53.1, 41.4, 28.2, 25.3, 23.4, 21.9.

n) methyl (benzyl(1,3-dioxoisoindolin-2-yl)carbamoyl)-L-threoninate (20181120-A774)

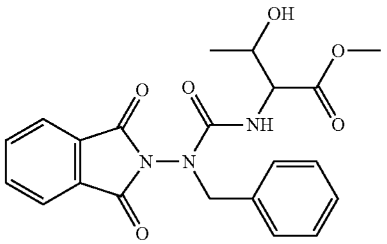 [SMILES: COC(=O)C(NC(=O)N(Cc1ccccc1)N1C(=O)c2ccccc2C1=O)C(C)O]

This compound was prepared according to procedure F on 0.05 mmol scale. This reaction gave the titled compound with (18 mg, 88%). $^1$HNMR (500 MHz, Acetone $d_6$) δ 7.90-7.84 (m, 4H), 7.43 (m, 2H), 7.27-7.21 (m, 3H), 6.37 (d, J=8.45 Hz, 1H), 4.93 (ABq, J=14.9 Hz, 2H), 4.41 (dd, J=3.25, 8.9 Hz, 1H), 4.19 (m, 1H), 3.79 (d, J=6.0 Hz, 1H), 3.64 (s, 3H), 1.50 (d, J=6.4 Hz, 3H); $^{13}$C NMR (125 MHz, Acetone $d_6$) δ 172.0, 166.1, 166.0, 157.6, 68.2, 60.4, 53.6, 52.3, 14.6.

o) 4-benzyl 1-methyl (benzyl(1,3-dioxoisoindolin-2-yl)carbamoyl)-L-aspartate (20181120-A777)

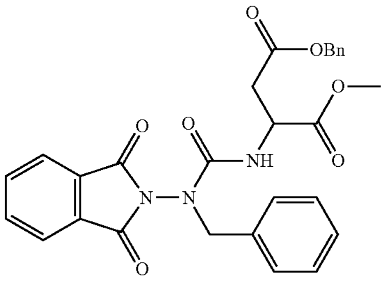 [SMILES: COC(=O)C(CC(=O)OCc1ccccc1)NC(=O)N(Cc1ccccc1)N1C(=O)c2ccccc2C1=O]

This compound was prepared according to procedure F on 0.05 mmol scale. This reaction gave the titled compound with (21 mg, 82%). $^1$HNMR (500 MHz, Acetone $d_6$) δ 7.8x-7.8x (m, 4H), 7.42-7.15 (m, 10H), 5.13 (q, J=xx Hz, 2H), 4.89 (q, J=xx Hz, 2H), 4.81 (m, 1H), 3.57 (s, 3H), 2.88 (m, 1H), 2.70 (dd, J=6.8, 16.25 Hz, 1H); $^{13}$C NMR (125 MHz, Acetone $d_6$) δ 171.5, 171.4, 165.8, 157.1, 137.1, 137.0, 135.7, 131.1, 130.0, 129.3, 129.0, 128.8, 128.7, 128.5, 124.3, 67.3, 53.2, 52.0, 51.5, 36.9.

p) methyl (benzyl(1,3-dioxoisoindolin-2-yl)carbamoyl)-L-methioninate (20181120-A770)

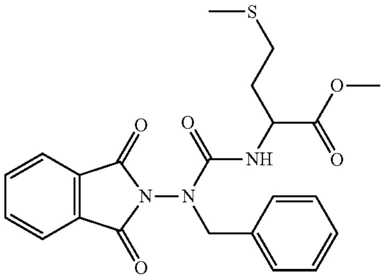 [SMILES: COC(=O)C(CCSC)NC(=O)N(Cc1ccccc1)N1C(=O)c2ccccc2C1=O]

This compound was prepared according to procedure F on 0.1 mmol scale. This reaction gave the titled compound with (42 mg, 95%). $^1$HNMR (600 MHz, Acetone $d_6$) δ 7.88-7.82 (m, 4H), 7.39-7.18 (m, 5H), 6.99 (d, J=8.4 Hz, 1H), 4.89 (q, J=14.7 Hz, 2H), 4.56 (m, 1H), 3.65 (s, 3H), 2.5745 (m, 2H), 2.02 (s, 3H), 2.00-1.97 (m, 1H), 1.82-1.78 (m, 1H); $^{13}$C NMR (150 MHz, Acetone $d_6$) δ 173.4, 166.0, 165.9, 157.3, 137.1, 135.7, 131.1, 130.1, 129.0, 128.5, 124.3, 124.2, 53.7, 53.1, 52.3, 32.1, 30.9, 15.3.

q) methyl $N^2$-(benzyl(1,3-dioxoisoindolin-2-yl)carbamoyl)-$N^6$-(tert-butoxycarbonyl)-L-lysinate (20181203-A785)

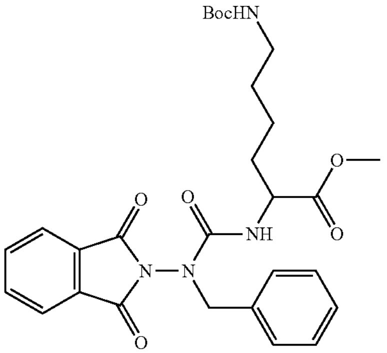 [SMILES: COC(=O)C(CCCCNC(=O)OC(C)(C)C)NC(=O)N(Cc1ccccc1)N1C(=O)c2ccccc2C1=O]

This compound was prepared according to procedure F on 0.076 mmol scale. This reaction gave the titled compound with (35 mg, 86%). $^1$HNMR (400 MHz, Acetone $d_6$) δ 7.83-7.81 (m, 4H), 7.40-7.19 (m, 5H), 6.89 (d, J=8.0 Hz, 1H), 5.89 (bs, 1H), 4.89 (ABq, J=16.0 Hz, 2H), 4.38 (m, 1H), 3.64 (s, 3H), 3.03 (m, 2H), 1.73 (m, 1H), 1.43 (m, 14H); $^{13}$C NMR.

Example 5

Procedures for Solution Phase and Solid Phase Peptide Synthesis

General

Solid phase peptide syntheses (SPPSes) were executed using Tribute® Peptide synthesizer from Gyros Protein Technologies, Inc. The machine is fully automated with two independent reaction vessels with polytetrafluoroethylene frits, five solvent positions and 101 amino acid positions. Preloaded Fmoc-L-Arg(Pbf) Wang resin (200-400 mesh, 0.3 mmol/g) and Rink amide MBHA resin (0.3 mmol/g), and premixed Fmoc amino acids with HATU coupling agent were purchased from Pure Pep™/Gyros Protein Technologies, Inc. All solvents, and reagents used in synthesis are peptide-grade and were purchased from Gyros Protein Technologies. The solvents and reagents were used without further treatment or drying. The Aza-amino acid were synthesized in Applicant's labs and integrated in the synthesis with minimal interruption to the automation, i.e, the activated aza-amino acid residue were added manually, by interrupting the synthesis momentarily, then the rest of the steps including the cleavage, washing, and drying were maintained automated. Analyses were performed using Water's technology HPLC equipped with a 1525 binary pump, and the use of analytical column (Phenomenex kinetex 2.6 μm EVO C18 analytical column 100 Å 150×4.6 mm). Chromatography was performed at ambient temperature with flow rate of 1.0 mL/min with linear gradient from Water (0.05% TFA): $CH_3CN$ (0.05% TFA) [95:5] to Water Water (0.05% TFA): $CH_3CN$ (0.05% TFA) [5:95] and resolved peaks were detected by 2998 photodiode Array (PDA) Detector at 254 and/or 215 nm and characterized by low resolution mass spectrometry instrument (Thermo Scientific LTQXL™) with ESI ion-source and positive mode ionization. Purification of the all peptidomimetics were performed on preparative HPLC purification system (Waters Prep 150 LC system combining 2545 Binary Gradient Module using XSelect Peptide CSH C18 OBD Prep Column, 130 Å, 5 μm, 19 mm×150 mm. Chromatography was performed at ambient temperature with a flow rate of 18 mL/min with a linear gradient from Water (0.1% FA): $CH_3CN$ (0.1% FA)[95:5] to Water (0.1% FA): $CH_3CN$ (0.1% TFA) [5:95] in 12 minutes, monitored by 2998 Photodiode Array (PDA) Detector UV at 254 nm and/or 215. NMR spectra were recorded in acetone-d6, CDCl3, D2O, and DMSO-d6 with TMS for 1H (500 and/or 600 MHz) and 13C (125 and/or 150 MHz) as an internal reference.

General Procedure for SPPS

All solid phase peptide couplings were performed at ambient temperature using Tribute® Peptide synthesizer from Gyros Protein Technologies, Inc following a protocol that included:

1. Swelling: The resin (loaded with the first Fmoc-protected amino acid) was swelled twice successively for 20 minutes in DMF, each swelling step followed by drain and drying step.
2. Fmoc Cleavage: the protected amino acid/or peptide was shaken for 2.0 min with 20% piperidine solution in DMF to remove the Fmoc group. The process was repeated twice, followed by several washing steps with DMF (3-5 times).
3. Amino acid coupling: 5 equivalents of the next acylating component (Fmoc protected amino acid or activated Aza-amino acid), 5 equivalents of Hexafluorophosphate Azabenzotriazole Tetramethyl Uronium coupling reagent ("HATU"), and 10 equivalents of N-methylmorpholine (base) were used to add the next amino acid in the sequence. This step is fully automated and was run according to the software installed on the Tribute® synthesizer. The amino acid with coupling reagent were delivered to the reaction vessel from the specified loading position upon dissolution. Then the base was added as 0.4 M solution in DMF, the total volume of solvent was adjusted to give 0.2 M solution. The coupling time was limited to 15 minutes shacking followed by draining, washing steps. Step 2 and step 3 were repeated until the sequence synthesis was done.
4. Washing: repeated washing steps were performed after each cleavage or coupling event using MDF as solvent (2-3 times). At the final coupling or cleavage steps additional washing with DCM was performed (5-6 times) to remove any trace of DMF. The process usually followed by drying step.
5. Cleavage from the Resin: 5.0 mL of a freshly made solution of TFA/$H_2O$/TIPS (95:2.5:2.5. v/v/v) was cooled down to 0° C. and added at OC to a 0.3 mmol of Resin. The mixture was shaken for 2 hours, then was filtered, the remaining resin was further washed with 0.5-1.0 mL of TFA/H2O) (95:5, v/v) solution. The filtrate was precipitated by adding 10 mL of 1:1 solution of ether: hexane. Upon centrifugation, the resulting solid was dissolved in a 1:1 solution of $CH_3CN$: $H_2O$. The resulting solution was lyophilized.
6. Purification: Purification of the all peptidomimetics were performed on preparative HPLC purification system (Waters Prep 150 LC system combining 2545 Binary Gradient Module using XSelect Peptide CSH C18 OBD Prep Column, 130 Å, 5 μm, 19 mm×150 mm. Chromatography was performed at ambient temperature with a flow rate of 18 mL/min with a linear gradient from Water (0.1% FA): $CH_3CN$ (0.1% FA) [95:5] to Water (0.1% FA): $CH_3CN$ (0.1% TFA) [5:95] in 12 minutes, monitored by 2998 Photodiode Array (PDA) Detector UV at 254 nm and/or 215.

Example 6

Synthesis of Aza-Amino Acid Surrogates

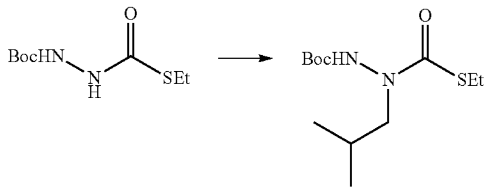

A783

To a solution of the thiocarbazate (110 mg, 0.5 mmol) in anhydrous THE (1.0 mL) $PBu_3$ (187 uL, 0.75 mmol) and isobutanol (47 uL, 0.5 mmol). The reaction mixture was cooled down to 0° C., then a 40% solution of DEAD (327 uL, 0.75 mmol) was added dropwise over 30 min. upon completion of the addition, the reaction mixture was allowed to rt gradually (30 min). Then, the volatiles were removed under vacuum and the residue was purified by FFC and the use of gradient of hexanes/ether. The target compound was collected as colorless crystals (81 mg, 59%); $^1$HNMR (500 MHz, Acetone $d_6$) δ8.63 (bs, 1H), 3.66 (m, 1H), 3.09 (m, 1H), 2.76 (m, 2H), 1.93 (m, 2H), 1.20 (t, J=6.15 Hz, 3H), 0.9 (bd, 6H). $^{13}$C NMR (125 MHz, Acetone $d_6$) δ 172.9, 154.7, 81.3, 56.8, 28.5, 27.3, 24.7, 20.5, 20.3, 15.7. structure was confirmed by X-ray.

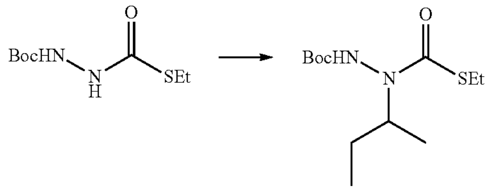

A7123

To a solution of the thiocarbazate (220 mg, 1.0 mmol) in anhydrous THE (1.0 mL), $PBu_3$ (303 uL, 1.2 mmol) and R-2-butanol (200 uL, 2.0 mmol). The reaction mixture was cooled down to 0° C., then a 40% solution of DEAD (522 uL, 1.2 mmol) was added dropwise over 30 min. upon completion of the addition, the reaction mixture was allowed to warm up to room temperature gradually (30 min). Then, the volatiles were removed under vacuum and the residue was purified by FFC and the use of gradient of hexanes/ether. The target compound was collected as colorless crystals (195 mg, 70%); $^1$HNMR (500 MHz, Acetone $d_6$) δ structure was confirmed by X-ray.

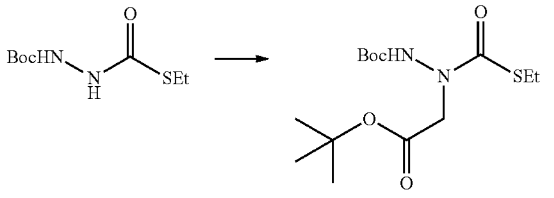

A790

To a solution of the thiocarbazate (110 mg, 0.5 mmol) in anhydrous THE (1.0 mL) $PBu_3$ (187 uL, 0.75 mmol) and tert-butyl 2-hydroxyacetate (99 mg, 0.75 mmol). The reaction mixture was cooled down to 0° C., then a 40% solution of DEAD (300 uL, 1.36 mmol) was added dropwise over 30 minutes. Upon completion of the addition, the reaction mixture was allowed to warm up to room temperature gradually (30 minutes). Then, the volatiles were removed under vacuum and the residue was purified by FFC and the use of gradient of hexanes/ether. $R_f$=0.44 (20% ether/hexane). The target compound was collected as colorless crystals (138 mg, 83%); $^1$HNMR (500 MHz, Acetone $d_6$) δ8.51 (bs, 1H), 4.69 (m, 1H), 3.73 (m, 1H), 2.79 (m, 2H), 1.45 (m, 18H), 1.22 (t, J=6.15 Hz, 3H). $^{13}$C NMR (125 MHz, Acetone $d_6$) δ 173.1, 82.4, 81.8, 51.5, 28.4, 28.2, 24.8, 15.6. Structure was analyzed by X-ray.

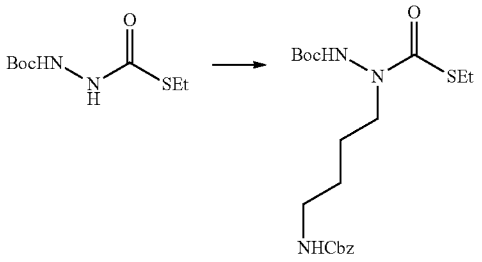

A794

To a solution of the thiocarbazate (60 mg, 0.272 mmol) in anhydrous THE (0.5 mL) $PBu_3$ (83 uL, 0.327 mmol) and benzyl (4-hydroxybutyl)carbamate (73 mg, 0.327 mmol). The reaction mixture was cooled down to 0° C., then a 40% solution of DEAD (327 uL, 0.75 mmol) was added dropwise over 30 minutes. Upon completion of the addition, the reaction mixture was allowed to warm up to room temperature gradually (30 minutes). Then, the volatiles were removed under vacuum and the residue was purified by FFC and the use of gradient of hexanes/ether. The target compound was collected as colorless wax (110 mg, 90%); $^1$HNMR (500 MHz, Acetone $d_6$) δ8.66 (s, 1H), 7.36-7.29 (m, 5H), 6.31 (bs, 1H), 5.05 (s, 2H), 3.86 (m, 1H), 3.31 (m, 1H), 3.16 (m, 2H), 2.74 (m, 2H), 1.57 (m, 2H), 1.54 (m, 2H), 1.46 (m, 9H), 1.20 (t, J=6.15 Hz, 3H). $^{13}$C NMR (125 MHz, Acetone $d_6$) δ 172.6, 157.3, 154.9, 138.6, 129.2, 128.7, 128.6, 81.4, 66.4, 49.0, 41.2, 28.4, 27.9, 25.0, 24.7, 15.7.

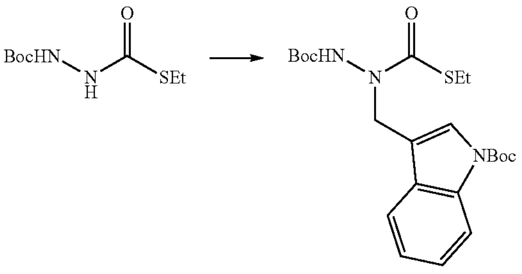

A7122

To a solution of the thiocarbazate (220 mg, 1.0 mmol) in anhydrous THE (1.5 mL) $PBu_3$ (379 uL, 1.5 mmol) and N-Boc indole-3-carbinol (309 mg, 1.25 mmol). The reaction mixture was cooled down to 0° C., then a 40% solution of DEAD (650 uL, 1.5 mmol) was added dropwise over 30 minutes. Upon completion of the addition, the reaction mixture was allowed to warm up to room temperature gradually (30 min). Then, the volatiles were removed under vacuum and the residue was purified by FFC and the use of gradient of hexanes/ether. The target compound was collected as colorless gummy material (380 mg, 85%); $^1$HNMR (500 MHz, Acetone $d_6$) δ

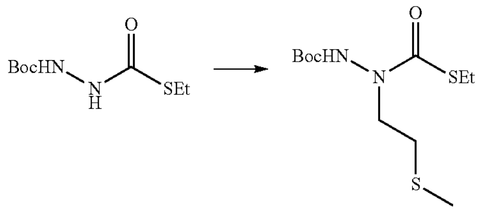

A8113

To a solution of the thiocarbazate (165 mg, 0.75 mmol) in anhydrous THE (1.0 mL) $PBu_3$ (284 uL, 1.125 mmol) and 2-Hydroxyethyl methyl sulfide (92 mg, 0.8 mmol). The reaction mixture was cooled down to 0° C., then a 40% solution of DEAD (489 uL, 1.125 mmol) was added dropwise over 30 minutes. Upon completion of the addition, the reaction mixture was allowed to warm up to room temperature gradually (30 minutes). Then, the volatiles were removed under vacuum and the residue was purified by FFC and the use of gradient of hexanes/ether. The target compound was collected as colorless crystals (150 mg, 68%); $^1$HNMR (500 MHz, Acetone $d_6$) δ.

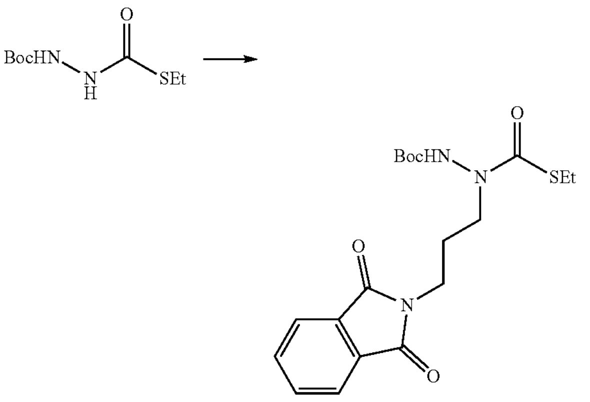

A822

To a solution of the thiocarbazate (160 mg, 0.73 mmol) in anhydrous THE (1.5 mL) $PBu_3$ (193 uL, 0.73 mmol) and N-Phthalimido-1-propanol (150 mg, 0.73 mmol). The reaction mixture was cooled down to 0° C., then a 40% solution of DEAD (660 uL, 1.0 mmol) was added dropwise over 30 minutes. Upon completion of the addition, the reaction mixture was allowed to warm up to room temperature gradually (30 minutes). Then, the volatiles were removed under vacuum and the residue was purified by FFC and the use of gradient of hexanes/ether. The target compound was collected as colorless gummy material (125 mg, 42%); $^1$HNMR (500 MHz, Acetone $d_6$) δ.

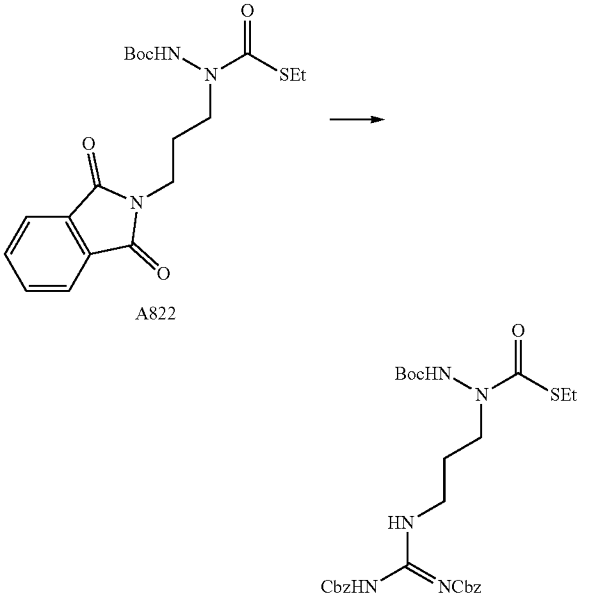

A822

A831

To a solution of semicarbazate A822 (75 mg, 0.18 mmol) in EtOH (2.0 mL) was added Hydrazine (23 uL, 0.37 mmol). The reaction mixture was heated at 40° C. for 2 hours, at which the starting material completely disappeared based on tlc. The organic volatiles were removed under vacuum and the residue was purified using C18 column with gradient of Water/$CH_3CN$. The pure fraction was collected based on the mass spectroscopy analysis. After 16 hour lyophilizing, the resulting amine was subjected to the next step without further treatment. To a solution of the resulting amine the previous step (23.0 mg, 0.08 mmol) in DCM (2.0 mL) was added Cbz-protected methylcarbamidothioate (86.0 mg, 0.24 mmol), DIPEA (15 uL, 0.08 mmol) and one crystal of DMAP. The reaction mixture was stirred at room temperature for 16 hours. Then, the organic volatiles were removed under vacuum and the residue was purified on silica and the use of gradient of EtOAc/Hexane to give 50 mg (45% over two steps).

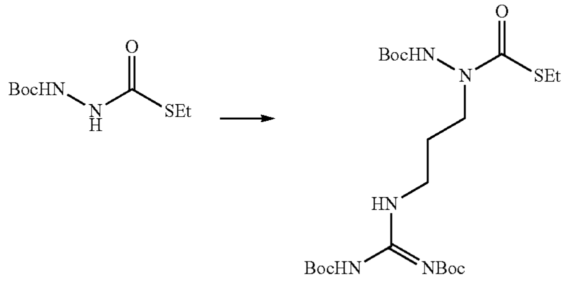

A8161

To a solution of the thiocarbazate (220 mg, 1.0 mmol) in anhydrous THE (2.0 mL) $PBu_3$ (500 uL, 2.0 mmol) and 3-(Di-tert-butyloxycarbonyl)guanidinopropanol (375 mg, 1.18 mmol). The reaction mixture was cooled down to 0° C. Then, a 40% solution of DEAD (870 uL, 2.0 mmol) was added dropwise over 30 minutes. Upon completion of the addition, the reaction mixture was allowed to warm up to room temperature gradually (30 min). Then, the volatiles were removed under vacuum and the residue was purified by FFC and the use of gradient of hexanes/ether. The target compound was collected as colorless gummy material (225 mg, 43%); $^1$HNMR (500 MHz, Acetone $d_6$) δ.

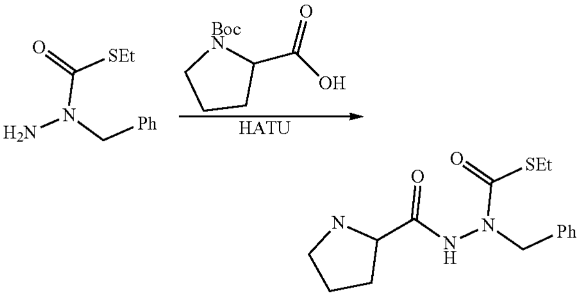

42%
A965

To a solution of S-ethyl 1-benzyl hydrazine-1-carbothioate (304 mg, 1.45 mmol) in DMF (8.0 mL) was added N-Boc Proline (343 mg, 1.59 mmol), HATU (722.4 mg, 1.59 mmol), HOBt (214 mg, 1.59 mmol), and N-methyl morpholine NMM (650 uL, 6.4 mmol). The reaction mixture was stirred at room temperature for 20 hours, then was treated with 0.5 M citric acid solution. The aqueous layer was extracted with EtOAc (15.0 mL×3), the combined organic fractions were washed with saturated $NaHCO_3$ solution, brain, and cold water, the organic layer was dried over $Na_2SO_4$, filtered, and evaporated under vacuum. The cured material was purified over silica by the use of gradient solvent mixture of Hexanes and EtOAc; the purified fraction was dried under high vacuum to give a white crystalline material (248 mg, 42%) LRMS (ESI, $MNa^+$) m/z calc for $C_{20}H_{29}N_3O_4SNa^+$ 430.18, found 430.3.

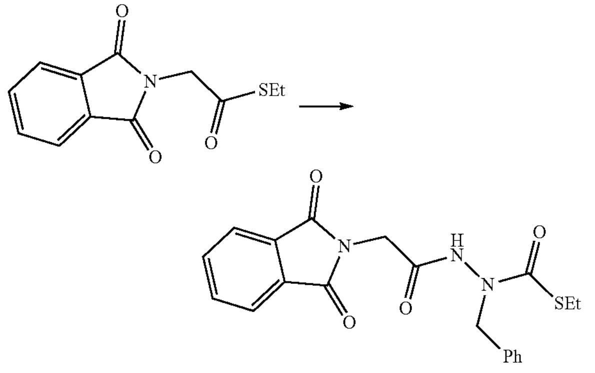

55%
A992

To a solution of phthalimidyl-Sethyl ethanethioate (62.25 mg, 0.25 mmol) in DCM (5.0 mL) was added TBACl (71.0 mg, 0.25 mmol). The reaction mixture was stirred at 0° C. for one min; then, the reaction mixture was treated with TCCA (58.0 mg, 0.25 mmol). The reaction mixture was allowed to warm up to room temperature in 10 minutes. At this time, a solution of thiocarbazate (Azaphe thioate) (52.0 mg, 0.25 mmol), DIPEA (177.0 uL, 1.0 mmol) and one crystal of DMAP in DCM (0.5 mL) was added at 0° C., and the reaction was stirred at room temperature for 2.0 hours before it was stopped by the addition of sodium thiosulfate (1 mL). The organic layer was washed with a saturated solution of sodium hydrogen sulfate, saturated solution of sodium bicarbonate, and brine. The organic layer was dried over sodium sulfate, filtered, and evaporated under vacuum. The residue was purified using FCC and gradient of hexane/ethyl acetate to give a gummy material (55 mg, 55% yield).

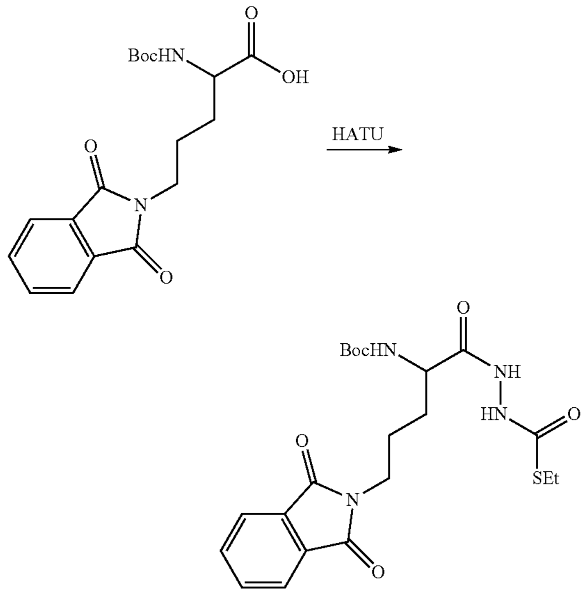

40%
A993

To a solution of S-ethyl hydrazinecarbothioate (240 mg, 2.0 mmol) in DMF (10.0 mL) was added N-alphaBoc-N-delta phthaloyl-L-Ornithine acid (800 mg, 2.0 mmol), HATU (760.5 mg, 2.0 mmol), HOBt (270 mg, 2.0 mmol), and DIPEA (1.4 mL, 4.0 mmol). The reaction mixture was stirred at room temperature for 20 hours, then was treated with 0.5 M citric acid solution. The aqueous layer was extracted with EtOAc (15.0 mL×3), the combined organic fractions were washed with saturated $NaHCO_3$ solution, brain, and cold water, the organic layer was dried over $Na_2SO_4$, filtered, and evaporated under vacuum. The cured material was purified over silica by the use of gradient solvent mixture of Hexanes and EtOAc; the purified fraction was dried under high vacuum to give a white solid material (400 mg, 40%).

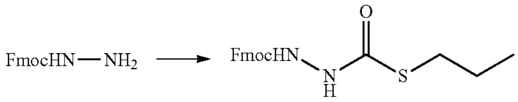

A9130

To a solution of S-propyl chlorothioformate (500 uL, 3.9 mmol) in THF (5 mL) was added DMAP (480 mg, 3.9 mmol) at 0° C. The reaction mixture was stirred at 0° C. until complete dissolution of the DMAP crystals and the appearance of copious white precipitate. At this point, a solution of $FmocNHNH_2$ (1.0 g, 3.9 mmol) in DCM (5 mL) was added slowly. Upon the completion of the addition, the reaction mixture was left to warm up to room temperature gradually. The reaction progress was monitored by TLC; after 2 hours, the reaction was stopped by adding ethyl ether (50 mL), the organic phase was transferred into a separatory funnel. It was treated with 1 M solution of HCl (25 mL). The organic phase was washed with a saturated solution of $NaHCO_3$ (20 mL), Braine (20 mL), dried over $Na_2SO_4$, and filtered. The excess solvent was evaporated under vacuum, and the crude mixture was suspended in 5 mL of $CH_3CN$, then filtered and dried to give 1.25 g of white non-crystalline powder (yield 89%), which was used in the next step without further purification. LRMS (ESI, $MNa^+$) m/z calc for $C_{19}H_{20}N_2NaO_3S$ 379.11, found 379.3.

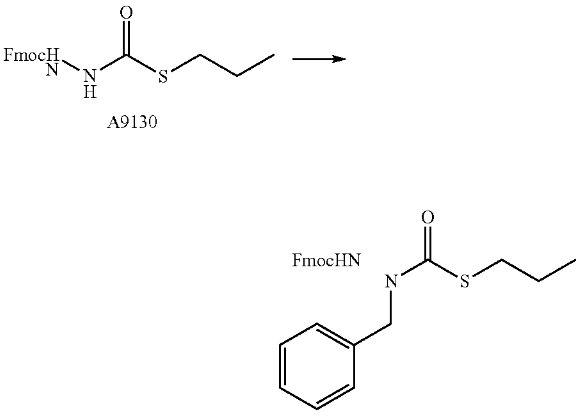

A9130

A9164T
58%

-continued

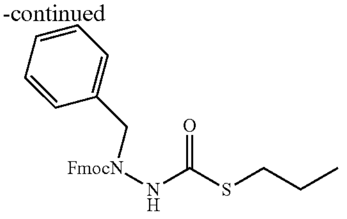

A9164B

14%

To a solution of thiocarbazate A9130 (356 mg, 1.0 mmol) in $CHCl_3$ (3.70 mL) was added $PBu_3$ (379 uL, 1.5 mmol) and BnOH (108 uL, 1.0 mmol) at −10° C. (ice/acetone/Salt). To the reaction mixture was added slowly during one hour a 20% solution of DEAD (1.3 mL, 1.5 mmol). The reaction mixture was left stirring at the same temperature for an additional hour or until the complete disappearance of the thiocarbazate. The reaction was stopped by adding 1 M solution of HCl (5.0 mL), and diethyl ether (10 mL). The organic layer was washed successively with a saturated solution of $NaHCO_3$ and brine. Later, the organic layer was dried over $Na_2SO_4$, filtered, and evaporated under vacuum. The crude material was subjected to FCC using gradient solution of ether and hexanes. The purified weigh 321 mg (72% yield). HPLC analysis indicated that the purified fraction is a mixture of 5:1 of two Regio-isomers, A9164T and A9164B. The purified fraction was suspended in 1 mL of $CH_3CN$ at room temperature then filtered; the purification process was repeated twice to give solely A9164T as a pure compound based on the HPLC analysis. LRMS (ESI, MNa+) m/z calc for $C_{26}H_{26}N_2O_3SNa$ 469.2, found 469.3.

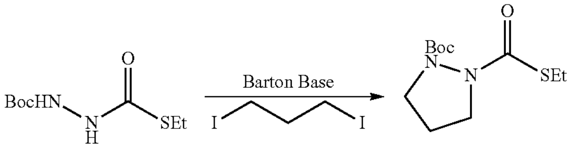

A9188

To a solution of thiosemicarbazide (1100 mg, 5.0 mmol) in anhydrous THF (20.0 mL) was added Barton Base (1.0 mL, 5.0 mmol). The reaction mixture was stirred at 0° C. for 10 min, at which diiodopropane (650 uL, 0.95 mmol) solution in THF (5.0 mL) was added drop-wise (over 30 minutes). The reaction mixture was stirred at 0° C. for 1 hour, then was left to warm up to room temperature gradually. Upon completion, the reaction was treated with 0.5 M HCl (10 mL) and was extracted with EtOAc (25 mL×4). The combined organic layer was washed with saturated $NaHCO_3$ (25 mL), Brine (25 mL), dried over $Na_2SO_4$, filtered and evaporated under vacuum, and the residue was purified by FCC to give the titled compound with (1.25 g, 96%). $^1$HNMR (500 MHz Acetone $d_6$) δ4.00 (m, 2H), 3.15 (m, 1H), 3.04 (m, 1H), 2.88 (m, 2H) 2.06 (m, 2H), 1.46 (s, 9H) 1.23 (t, J=7.32 Hz, 3H); $^{13}$C NMR (125 MHz, Acetone $d_6$) δ175.2, 156.9, 82.6, 46.8, 46.2, 28.3, 25.7, 24.4, 15.2 LRMS (ESI, MNa+) m/z calc for $C_{11}H_{20}N_2O_3SNa$ 283.11, found 283.1. A9188.

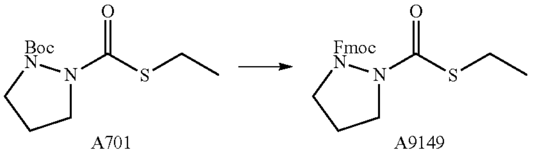

A701 A9149

To a solution of the thiocarbazate A701 (260 mg, 1.0 mmol) in DCM (4.0 mL) was added 1.0 mL of TFA. The reaction mixture was stirred at room temperature for 30 minutes; then, the volatiles was evaporated in vacuum. The residue was dried further under a high vacuum for an additional 30 min. Later, the residue was dissolved in anhydrous THF (5.0 mL) and treated with solid $NaHCO_3$ (840 mg, 10 mmol). The suspension was treated with Fmoc-Cl (258 mg, 1.0 mmol), and the reaction mixture was stirred at room temperature for 2 hours. The $NaHCO_3$ was filtered the filtrate was evaporated to dryness then was purified using FCC and gradient of ether/hexanes. LRMS (ESI, MNa+) m/z calc for $C_{21}H_{22}N_2O_3SNa$ 405.12, found 405.3.

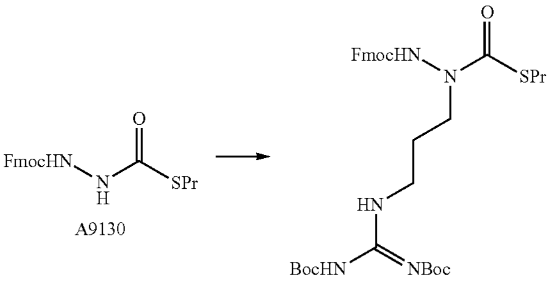

A9130

42%

A1006

To a solution of thiocarbazate A9130 (356 mg, 1.0 mmol) in $CHCl_3$ (3.70 mL) was added $PBu_3$ (379 uL, 1.5 mmol) and 3-(Di-tert-butyloxycarbonyl)guanidinopropanolii (317 mg, 1.0 mmol) at −10° C. (ice/acetone/Salt). To the reaction mixture was added slowly a 20% solution of DEAD (1.3 mL, 1.5 mmol) during one hour. The reaction mixture was left stirring at the same temperature for an additional hour or until the complete disappearance of the thiocarbazate. The reaction was stopped by adding 1 M solution of HCl, 5.0 mL, and diethyl ether 10 mL. The organic layer was washed successively with a saturated solution of $NaHCO_3$ and brine. Later, the organic layer was dried over $Na_2SO_4$, filtered, and evaporated under vacuum. The crude material was subjected to FCC using gradient solution of ether and hexanes. The purified material weigh 350 mg (42% yield) or 80% based on recovered thiocarbazate A9130. LRMS (ESI, MH+) m/z calc for $C_{33}H_{45}N_5O_7SH^+$656.31, found 656.3.

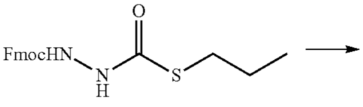

A9130

-continued

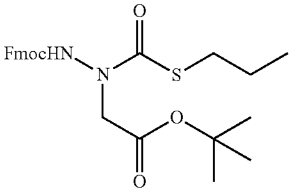

A1019

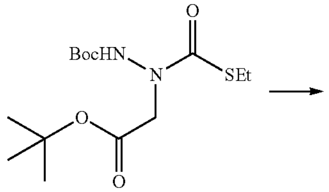

A790

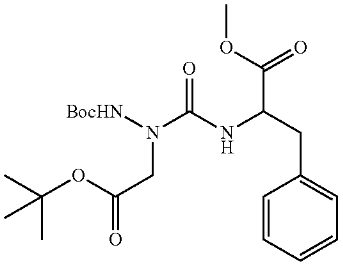

A791

To a solution of thiocarbazate A9130 (356 mg, 1.0 mmol) in CHCl3 (4.5 mL) was added PBu3 (379 uL, 1.5 mmol) and tert-butyl 2-hydroxy acetate (132 mg, 1.0 mmol) at −10° C. (ice/acetone/Salt). A 20% solution of DEAD (1.3 mL, 1.5 mmol) was added dropwise to the reaction mixture during one-hour using a syringe pump with an addition rate of 1.3 mL/h. The reaction mixture was left stirring at the same temperature for an additional hour or until the complete disappearance of the starting material. The volatile solvents were removed under vacuum, and the residue was loaded into a silica column and eluted with gradient solvent of Hexane/EtOAc up to 20% EtOAc. LRMS (ESI, MH+) m/z calc for C25H30N2O5SNa+493.18, found 493.2.

Example 7

Coupling Aza-Amino Acids Surrogates with Native Amino Acids

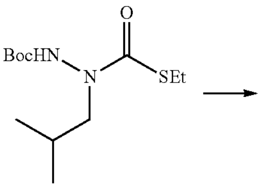

A783

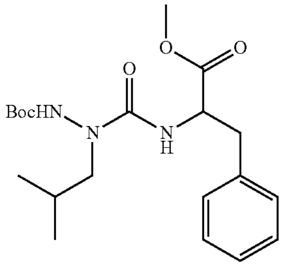

A787

To a solution of thiocarbazate A783 (28.0 mg, 0.1 mmol) in DCM (1.0 mL) was added TBACl (28 mg, 0.1 mmol). The reaction mixture was stirred at 0° C. for one min; then, the reaction mixture was treated with TCCA (23 mg, 0.1 mmol). The reaction mixture was allowed to warm up to room temperature in 15 minutes. At this time, a solution of phenylalanine methyl ester (32.3 mg, 0.15 mmol) and DIPEA (71 uL, 0.4 mmol) in DCM (0.5 mL) was added at 0° C., and the reaction was stirred at room temperature for 30 minutes before it was stopped by the addition of sodium thiosulfate (1 mL). The organic layer was washed with a saturated solution of sodium hydrogen sulfate, saturated solution of sodium bicarbonate, and brine. The organic layer was dried over sodium sulfate, filtered, and evaporated under vacuum. The residue was purified using FCC and gradient of hexane/ethyl acetate to give a white solid material$_6$).

To a solution of thiocarbazate A790 (22.0 mg, 0.065 mmol) in DCM (1.0 mL) was added TBACl (18.24 mg, 0.065 mmol). The reaction mixture was stirred at 0° C. for one minute; then, the reaction mixture was treated with TCCA (15 mg, 0.065 mmol). The reaction mixture was allowed to warm up to room temperature in 15 minutes. At this time, a solution of phenylalanine methyl ester (21.5 mg, 0.1 mmol) and DIPEA (46 uL, 0.26 mmol) in DCM (0.5 mL) was added at 0° C., and the reaction was stirred at room temperature for 30 minutes before it was stopped by the addition of sodium thiosulfate (1 mL). The organic layer was washed with a saturated solution of sodium hydrogen sulfate, saturated solution of sodium bicarbonate, and brine. The organic layer was dried over sodium sulfate, filtered, and evaporated under vacuum. The residue was purified using FCC and gradient of hexane/ethyl acetate to give a white solid material (25.5 mg, 87% yield). $R_f$=0.375 (30% EtOAc/Hexane). $^1$HNMR (500 MHz, Acetone $d_6$) δ7.90 (bs, 1H), 7.32-7.20 (m, 5H), 6.35 (m, 1H), 4.60 (m, 1H), 3.66 (s, 3H), 3.09 (m, 2H) 2.8 (s, 2H), 1.44 (m, 18H). $^{13}$C NMR (125 MHz, Acetone $d_6$) δ.

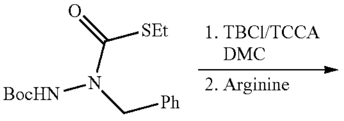

A738

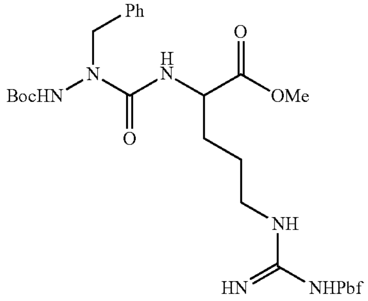

A8163

48%

To a solution of thiocarbazate A738 (310.0 mg, 1.0 mmol) in DCM (18.0 mL) was added TBACl (277 mg, 1.0 mmol). The reaction mixture was stirred at 0° C. for one minute; then, the reaction mixture was treated with TCCA (232, 1.0 mmol). The reaction mixture was allowed to warm up to room temperature in 15 minutes. At this time, a solution of Arginine (Pbf) methyl ester (715.5 mg, 1.5 mmol) and DIPEA (750 uL, 4.0 mmol) in DCM (2.0 mL) was added at 0° C., and the reaction was stirred at room temperature for 30 minutes before it was stopped by the addition of sodium thiosulfate (5.0 mL). The organic layer was washed with a saturated solution of sodium hydrogen sulfate, saturated solution of sodium bicarbonate, and brine. The organic layer was dried over sodium sulfate, filtered, and evaporated under vacuum. The residue was purified using FCC and gradient of hexane/ethyl acetate to give a white solid material (330 mg, 48% yield). LRMS (ESI, MH+) m/z calc for $C_{33}H_{48}N_6O_8SH^+$689.33, found 689.3.

Azapeptide A8163 (95.0 mg, 0.138 mmol) was treated with 4M HCl (2.0 mL) at 0° C. the reaction was stirred for one hour with gradual warm up to room temperature. Upon completion based on TLC and mass spec, the excess solvent was evaporated under vacuum, and the residue was dried further under high vacuum. Later, the deprotected Aza peptide (81.0 mg, 0.138) was dissolved in DMF (1.0 mL) and then was treated with acid A8192 (7.0 mg, 0.138 mmol), HATU (53.0 mg, 0.138 mmol), HOBt (19.0 mg, 0.138 mmol), and DIPEA (103 uL, 0.56 mmol). The reaction mixture was stirred at room temperature for 16 hours; then, the reaction was treated with a saturated solution of sodium hydrogen sulfate (2.0 mL). The aqueous layer was extracted with DCM (2.0 mL×4). The combined organic layer was washed with the brain, dried over sodium sulfate, filtered, and evaporated under vacuum, the resulting residue was purified using silica gel and gradient of EtOAc/MeOH, up to

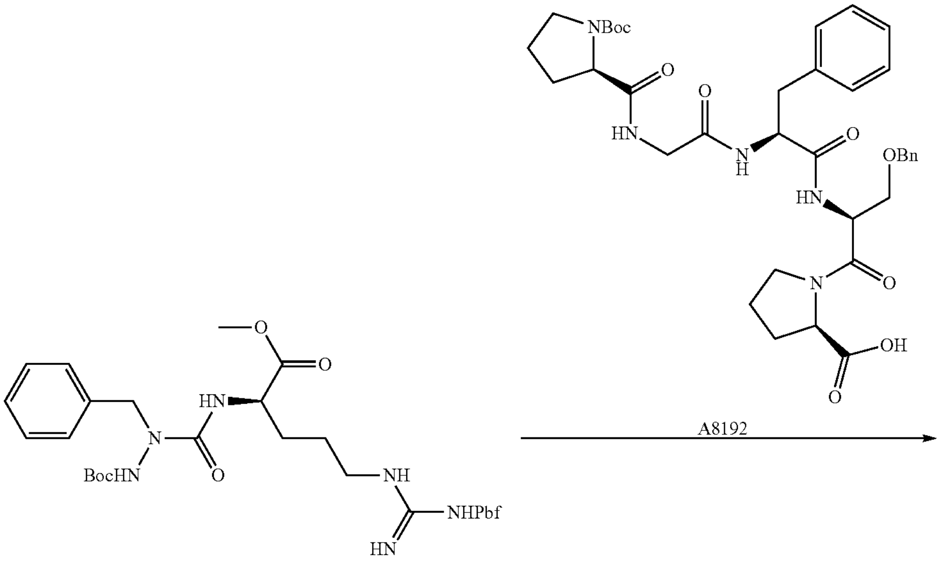

A8163

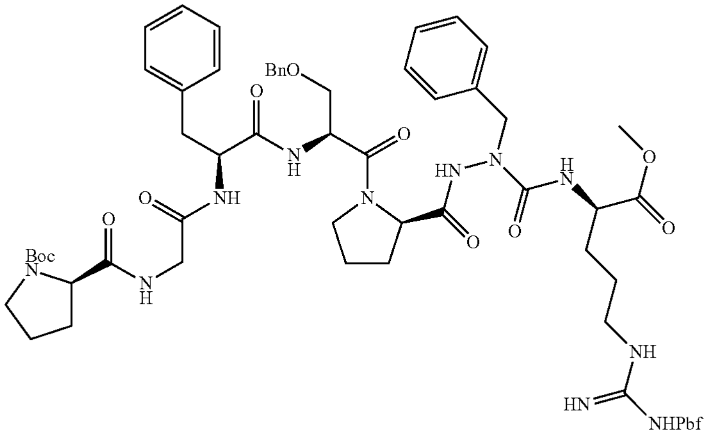

A8194

5% MeOH. The purified fraction was assessed by HPLC. LRMS (ESI, MH+) m/z calc for $C_{64}H_{85}N_{11}O_{14}SH^{+}$1264.60, found 12264.6.

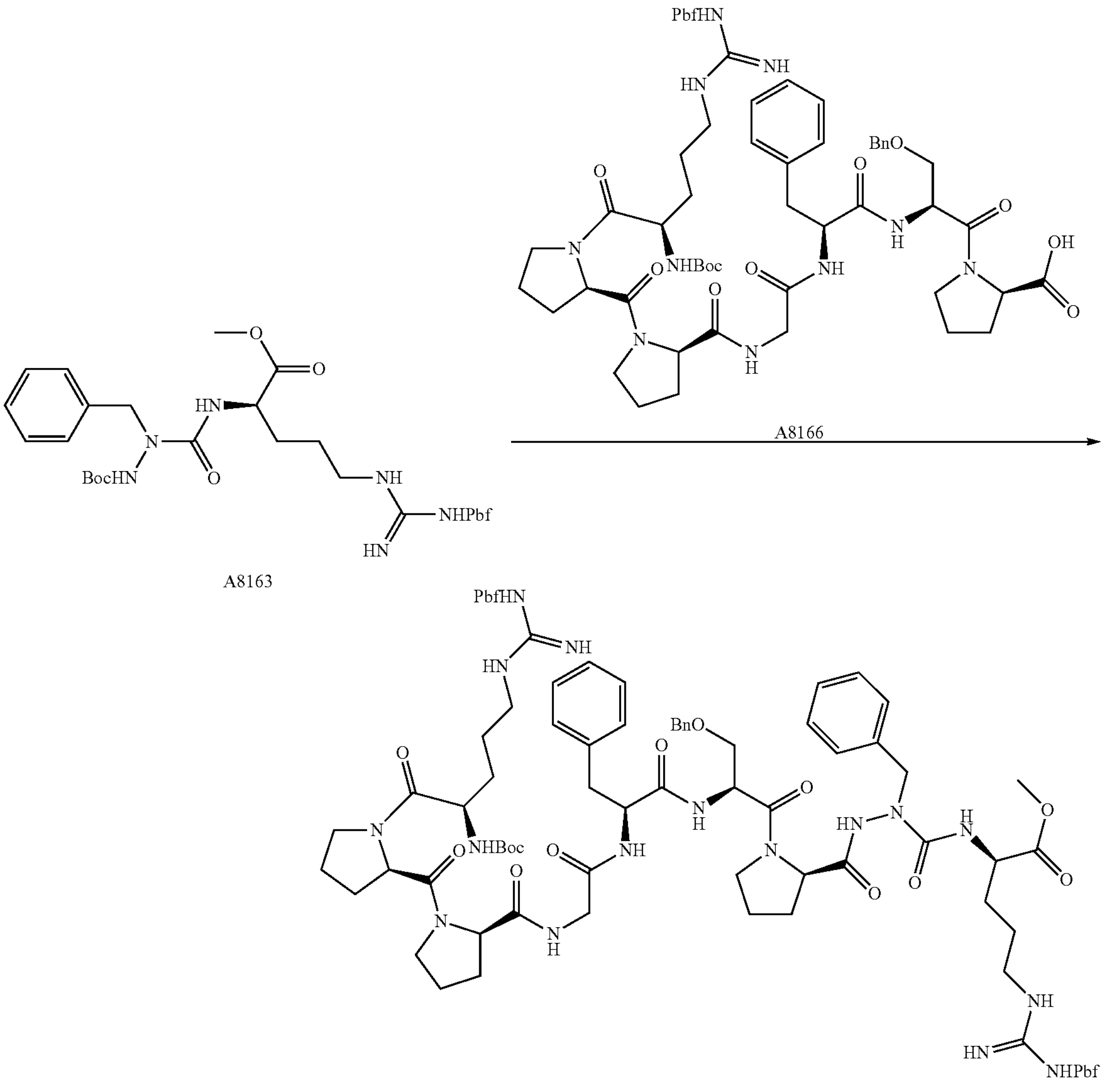

A8163

A8168 protected 8AzaBK

Azapeptide A8163 (81.0 mg, 0.1177 mmol) was treated with 4M HCl (2.0 mL) at 0° C. the reaction was stirred for one h with gradual warm up to room temperature. Upon completion based on TLC and mass spec (mass found 589.26), the excess solvent was evaporated under vacuum, and the residue was dried further under high vacuum. Later, the deprotected Aza peptide (69.0 mg, 0.1177) was dissolved in DMF (1.0 mL) and then was treated with acid A8166 (130 mg, 0.107 mmol), HATU (45.0 mg, 0.1177 mmol), HOBt (16.0 mg, 0.1177 mmol), and NMM (79 uL, 0.43 mmol). The reaction mixture was stirred at room temperature for 16 hours; then, the reaction was treated with a saturated solution of sodium hydrogen sulfate (2.0 mL). The aqueous layer was extracted with DCM (2.0 mL×4). The combined organic layer was washed with the brain, dried over sodium sulfate, filtered, and evaporated under vacuum, the resulting residue was purified using silica gel and gradient of EtOAc/MeOH, up to 5% MeOH. The purified fraction was assessed by HPLC. LRMS (ESI, MH+) m/z calc for $C_{88}H_{120}N_{16}O_{19}S2H^{+}$1769.84, found 1769.8.

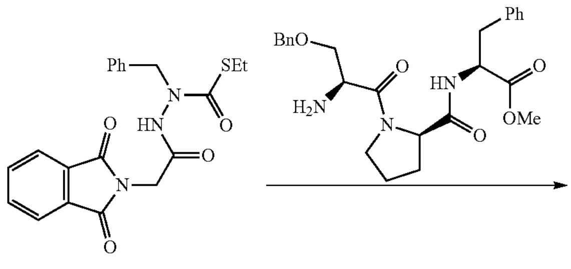

A992

-continued

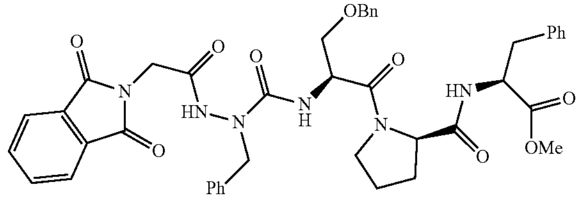

A995

To a solution of thiocarbazate A992 (20.0 mg, 0.05 mmol) in DCM (1.0 mL) was added TBACl (14.0 mg, 0.05 mmol). The reaction mixture was stirred at 0° C. for one minute; then, the reaction mixture was treated with TCCA (12 mg, 0.05 mmol). The reaction mixture was allowed to warm up to room temperature in 15 minutes. At this time, a solution of the free amine tripeptide (SPF) (34.0 mg, 0.075 mmol) and DIPEA (35 uL, 0.2 mmol) in DCM (1.0 mL) was added at 0° C., and the reaction was stirred at room temperature for 30 minutes before it was stopped by the addition of sodium thiosulfate (5.0 mL). The organic layer was washed with a saturated solution of sodium hydrogen sulfate, saturated solution of sodium bicarbonate, and brine. The organic layer was dried over sodium sulfate, filtered, and evaporated under vacuum. The residue was purified using FCC and gradient of hexane/ethyl acetate to give a white foamy material. LRMS (ESI, MNa+) m/z calc for $C_{43}H_{44}N_6O_9H^+$ 789.32, found 789.3.

Example 8

Integration of the AzaPhenylalanine in SPPS

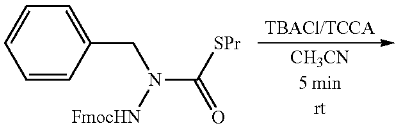

4 equiv.

A9164T

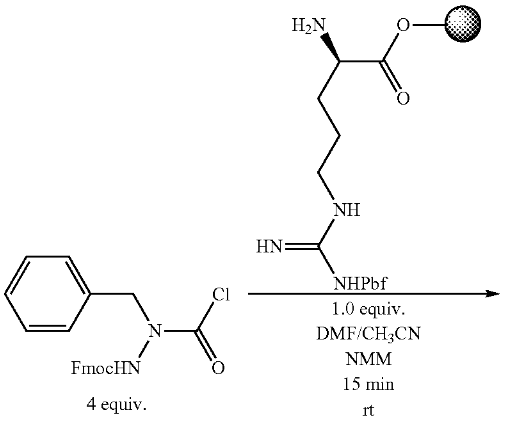

4 equiv.

-continued

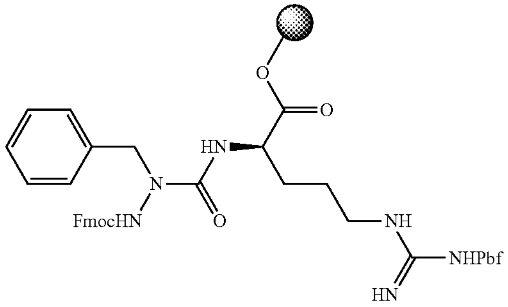

A9171

Wang Arginine-loaded Resin® was swelled in DMF for 20 minutes, followed by treatment with a 20% solution of Piperidine in DMF for 2 min using two cycles to cleave the Fmoc group. After successive washes with DMF, the resin was suspended in DMF mixed with 10 equivalents of the N-Methyl morpholine base (NMN) for 10 minutes. During this time, and separately, 4 equivalents of the thiocarbazate A9164T in 2 mL of $CH_3CN$, then was treated with an equal molar ratio of TBACl, after shacking the mixture for 1 minute, equal molar ratio of TCCA was added to activate the thiocarbazate scaffold. The reaction mixture was stirred at room temperature for 5 min, then was centrifuged. The clear supernatant was introduced into the suspended resin and the pH value was adjusted to 8.0 by adding additional 10 equivalents of NMM (neat). The Reaction mixture was shaken for 15 minutes, followed by 5 cycles of washing then, drying. The resulting dipeptide was treated with acetic anhydride ($Ac_2O$) and Diisopropylethylamine (DIPEA) to cap any left arginine (two cycles). A small amount of the resin was cleaved using TFA/DCM mixture, and the resulting peptide was analyzed by HPLC, which indicated a complete conversion and absence of capped products. LRMS (ESI, MH+) m/z calc for $C_{29}H_{32}N_6O_5H$ 545.25, found 545.4.

Example 9

Functionalization of Aza-Peptide with Native Amino Acid

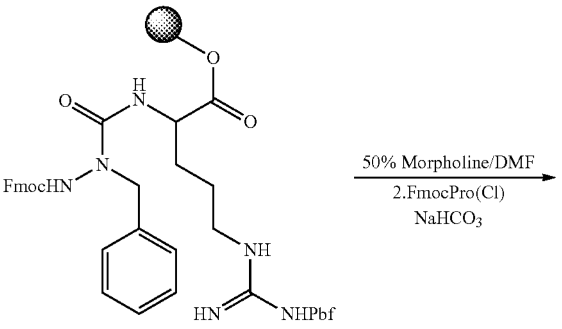

A9171

-continued

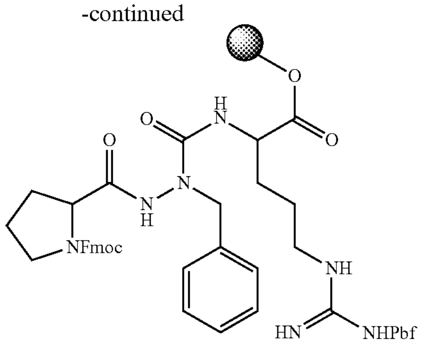

A9180

1. Preparation of the Fmoc-Pro(Cl): To a solution of Fmoc-Proline (1.0 g, 3.0 mmol) in DCM (10 mL) was added 0.1 mL of DMF. At 0° C., the reaction mixture was treated with thionyl chloride (2.0 mL). The reaction mixture was brought gradually to room temperature and left stirring for an additional 2 h. The volatiles was removed under vacuum, and the residue was triturated with a solution of ether: hexane (1:1, v/v) (10 mL). The residue was dried under high vacuum for 30 min and used in the next step without further treatment.
2. Cleavage of the Fmoc group from the dipeptide that bound to the resin: Dipeptide A19171 (34 mg, 0.01 mmol) was suspended in 250 uL of DMF. The mixture was then agitated for 10 minutes, followed by removal of the solvent by filtration, then the process was repeated one more time. The swelled resin was treated with 50% solution of morpholine in DMF (250 uL), the mixture was shaken for 2 min, then the solvent was drained, and the process was repeated one more time. The Fmoc cleavage process was followed by several washes with DMF (250 uL×3). The resulting resin-bound peptide from the previous step (approx. 0.01 mmol) was suspended in dioxane (200 uL), treated with $NaHCO_3$ (16.8 mg, 0.2 mmol), and shaken for 10 minutes. Fmoc-Pro(Cl) from the first step (18.0 mg, 0.05 mmol) was dissolved in dioxane (200 uL) and introduced to the SPPS reaction vessel containing the $NaHCO_3$ in Dioxane. The resin was shaken at ambient temperature for 45 min. Then, the solvent was drained, and the resin was washed successively with H2O (300 uL×2), DMF (300 uL×3), and DCM (300 uL×5). The resin was dried, and a small sample was cleaved with TFA for analysis.

Example 10

Using SPPS and following the above-mentioned protocol, 2-azabradykinin ("2AzaBK"), 5-azabradykinin ("5AzaBK"), 8-azabradykinin ("8AzaBK"), 7-azabradykinin ("7AzaBK"), and 2,8azabradykin ("2,8AzaBK") were producted. The chemical formulas for 2AzaBK, 8AzaBK, 7AzaBK, 2,8AzaBK are follows:

2AzaBK

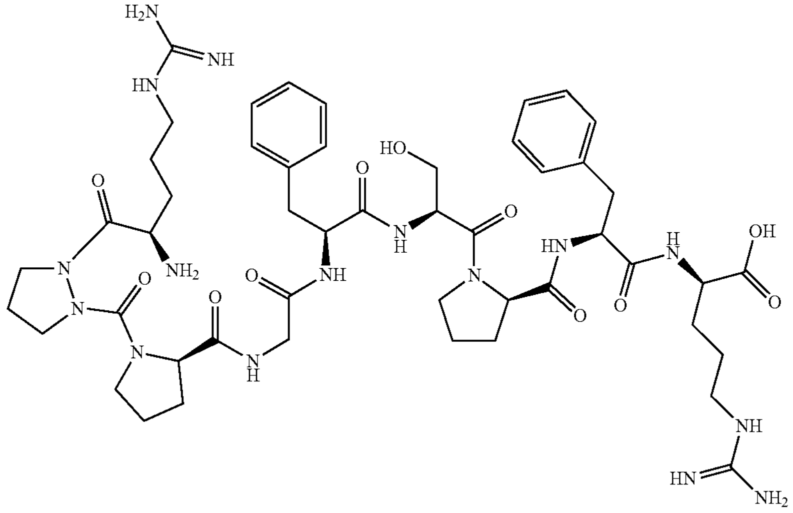

-continued
5AzaBK
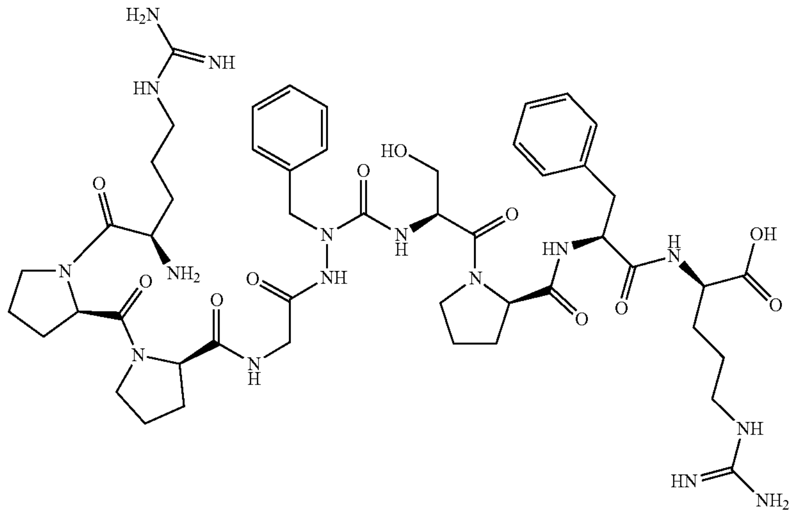
7AzaBK
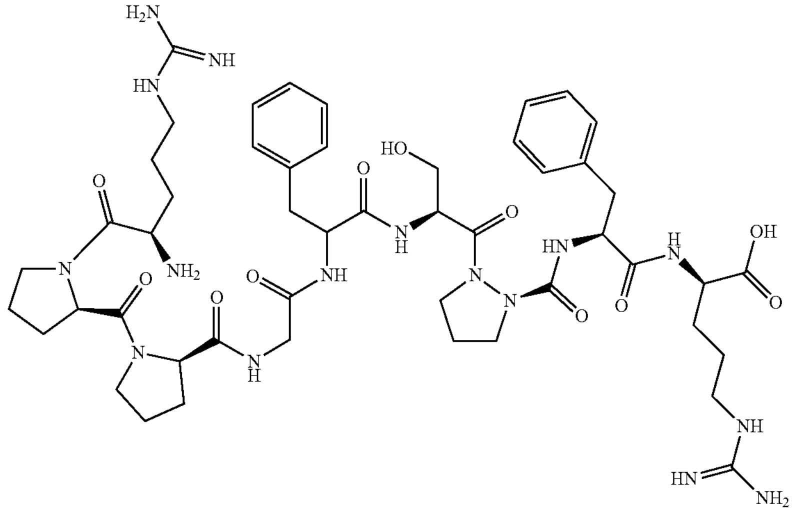
8AzaBK
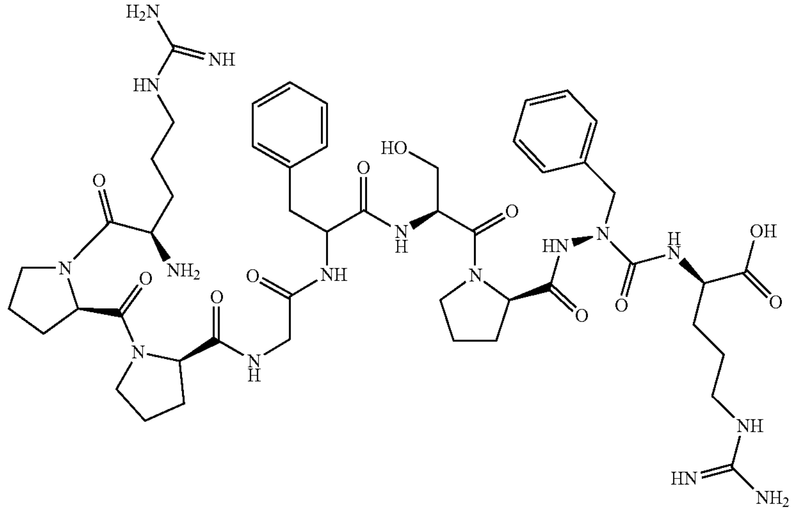

-continued 2,8AzaBK

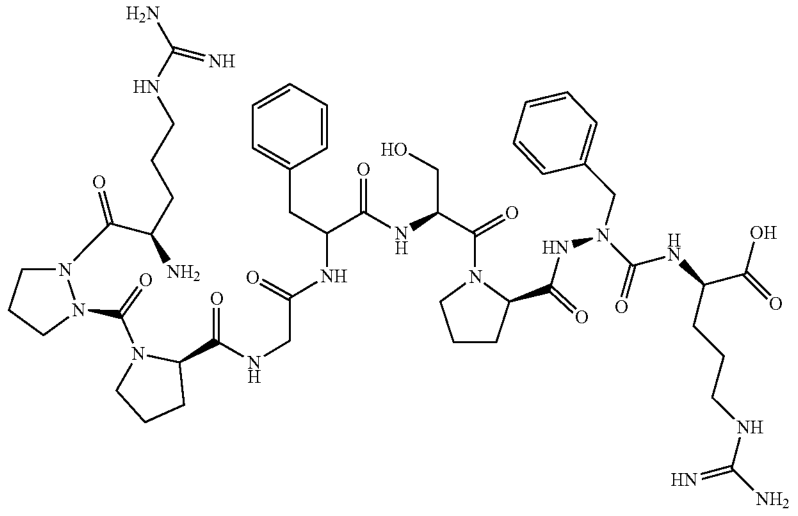

The yield and purity of the synthesized compounds is provided in Table 1.

TABLE 1

| Entry | AzaBK code | $T_R$* Min | Purity HPLC | Mass Found |
|---|---|---|---|---|
| 1 | 2 AzaBK | 4.891 | 97% | 1060.56 |
| 2 | 5 AzaBK | 7.45 | 70% Crude | 1282.62 |
| 3 | 7 AzaBK | 5.066 | 92.6% | 1060.56 |
| 4 | 8 AzaBK | 5.072 | 97.7% | 1060.56 |
| 5 | 2,8AzaBK | 4.940 | 98.5% | 1061.55 |

*$T_R$ = retention time which is the time when the peak of the corresponding peptide eluite from the C18 chromatography column during the HPLC analysis.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense. All documents cited herein, as well as text appearing in the figures, are hereby incorporated by reference in their entirety for all purposes to the same extent as if each were so individually denoted.

What is claimed is:

1. A compound of the Formula (I):

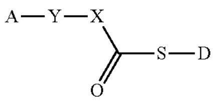

(I)

wherein

A is a protecting group selected from the group consisting of tert-butoxycarbonyl, 9-fluorenylmethoxycarbonyl, carboxybenzyl, 2-(3,5-dimethoxyphenyl) propan-2-yloxycarbonyl, 2,2,4,6,7,-pendamethyl-dihydrobenzofuran-5-sulfonyl, triphenylmethyl, tert-butylcarbonyl, t-butoxy, allyloxycarbonyl, methoxytrimethylbenzene sulfonyl, 4,4-dimethoxy benzhydryl, 2,2,5,7,8-pentamethylchroman-6-sulfonyl, 2,4,6-trimethoxybenzyl, allylcarbonyl, and acetamidomethyl;

Y is $NR_1$;

X is $NR_5$;

D is H, Cl, substituted or unsubstituted alkyl, substituted or unsubstituted aryl, or substituted or unsubstituted heteroaryl;

$R_1$ is H, substituted or unsubstituted alkyl, substituted or unsubstituted alkoxy, substituted or unsubstituted alkoxyalkylene, optionally protected alkyl amine, or a side chain radical of an amino acid, which is unsubstituted or substituted; and $R_5$ is H, an unsubstituted alkyl, unsubstituted alkoxy, substituted or unsubstituted alkoxyalkylene, optionally protected alkyl amine, or a side chain radical of an amino acid, which is substituted or unsubstituted, or an alkyl substituted one or more times by one or more substituents selected from the group consisting of halo, $C_1$-$C_6$ alkyl, —COOR, —COR, methoxy, ethoxy, propoxy, $C_1$-$C_6$ haloalkyl, and a protecting group, wherein R is an alkyl; or $R_1$ and $R_5$ are together joined by $—(CH_2—CH_2—CH_2)—$.

2. The compound according to claim 1, wherein A is selected from the group consisting of tert-butoxycarbonyl, 9-fluorenylmethoxycarbonyl, and carboxybenzyl.

3. A compound of the Formula (I):

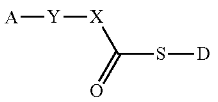

(I)

wherein

A is a protecting group selected from the group consisting of tert-butoxycarbonyl, 9-fluorenylmethoxycarbonyl, carboxybenzyl, 2-(3,5-dimethoxyphenyl) propan-2-yloxycarbonyl, 2,2,4,6,7,-pendamethyl-dihydrobenzofuran-5-sulfonyl, triphenylmethyl, tert-butylcarbonyl, t-butoxy, allyloxycarbonyl, methoxytrimethylbenzene sulfonyl, 4,4-dimethoxy benzhydryl, 2,2,5,7,8-pentamethylchroman-6-sulfonyl, 2,4,6-trimethoxybenzyl, allylcarbonyl, and acetamidomethyl;

Y is $NR_1$;

X is $NR_5$;

D is H, Cl, substituted or unsubstituted alkyl, substituted or unsubstituted aryl, or substituted or unsubstituted heteroaryl;

$R_1$ is a radical of an amino acid, wherein the amino acid is selected from the group consisting of aspartic acid, phenylalanine, alanine, histidine, glutamic acid, tryptophan, valine, leucine, lysine, methionine, tyrosine, isoleucine, arginine, glycine, asparagine, serine, and glutamine, which are unsubstituted or substituted by one or more substituents selected from the group consisting of halo, $C_1$-$C_6$ alkyl, —COOR, —COR, methoxy, ethoxy, propoxy, $C_1$-$C_6$ haloalkyl, and a protecting group, wherein R is alkyl; and $R_5$ is H, substituted or unsubstituted alkyl, substituted or unsubstituted alkoxy, substituted or unsubstituted alkoxyalkylene, optionally protected alkyl amine, or a side chain radical of an amino acid, which is substituted or unsubstituted.

4. A compound of the Formula (I):

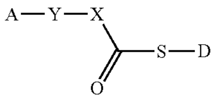

(I)

wherein

A is a protecting group selected from the group consisting of tert-butoxycarbonyl, 9-fluorenylmethoxycarbonyl, carboxybenzyl, 2-(3,5-dimethoxyphenyl) propan-2-yloxycarbonyl, 2,2,4,6,7,-pendamethyl-dihydrobenzofuran-5-sulfonyl, triphenylmethyl, tert-butylcarbonyl, t-butoxy, allyloxycarbonyl, methoxytrimethylbenzene sulfonyl, 4,4-dimethoxy benzhydryl, 2,2,5,7,8-pentamethylchroman-6-sulfonyl, 2,4,6-trimethoxybenzyl, allylcarbonyl, and acetamidomethyl;

Y is $NR_1$;

X is $NR_5$;

D is H, Cl, substituted or unsubstituted alkyl, substituted or unsubstituted aryl, or substituted or unsubstituted heteroaryl;

$R_1$ is H, substituted or unsubstituted alkyl, substituted or unsubstituted alkoxy, substituted or unsubstituted alkoxyalkylene, optionally protected alkyl amine, or a side chain radical of an amino acid, which is unsubstituted or substituted; and $R_5$ is a radical of an amino acid wherein the amino acid is selected from the group consisting of aspartic acid, phenylalanine, alanine, histidine, glutamic acid, tryptophan, valine, leucine, lysine, methionine, tyrosine, isoleucine, arginine, glycine, asparagine, serine, and glutamine, which are unsubstituted or substituted by one or more substituents selected from the group consisting of halo, a $C_1$-$C_6$ alkyl, —COOR, —COR, methoxy, ethoxy, propoxy, $C_1$-$C_6$ haloalkyl, and a protecting group, wherein R is alkyl.

5. A compound of the Formula (I):

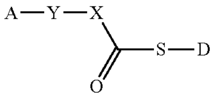

(I)

wherein

A is a protecting group selected from the group consisting of tert-butoxycarbonyl, 9-fluorenylmethoxycarbonyl, carboxybenzyl, 2-(3,5-dimethoxyphenyl) propan-2-yloxycarbonyl, 2,2,4,6,7,-pendamethyl-dihydrobenzofuran-5-sulfonyl, triphenylmethyl, tert-butylcarbonyl, t-butoxy, allyloxycarbonyl, methoxytrimethylbenzene sulfonyl, 4,4-dimethoxy benzhydryl, 2,2,5,7,8-pentamethylchroman-6-sulfonyl, 2,4,6-trimethoxybenzyl, allylcarbonyl, and acetamidomethyl;

Y is $NR_1$;

X is $NR_5$;

D is substituted or unsubstituted alkyl, substituted or unsubstituted aryl, or substituted or unsubstituted heteroaryl, and the substituents are selected from the group consisting of halo, $C_1$-$C_6$ alkyl, —COOR, —COR, methoxy, ethoxy, propoxy, and $C_1$-$C_6$ haloalkyl, wherein R is alkyl, $R_1$ is H, substituted or unsubstituted alkyl, substituted or unsubstituted alkoxy, substituted or unsubstituted alkoxyalkylene, optionally protected alkyl amine, or a side chain radical of an amino acid, which is unsubstituted or substituted; and $R_5$ is H, substituted or unsubstituted alkyl, substituted or unsubstituted alkoxy, substituted or unsubstituted alkoxyalkylene, optionally protected alkyl amine, or a side chain radical of an amino acid, which is substituted or unsubstituted.

6. The compound according to claim 1, A compound of the Formula (I):

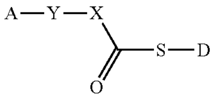

(I)

wherein

A is a protecting group selected from the group consisting of tert-butoxycarbonyl, 9-fluorenylmethoxycarbonyl, carboxybenzyl, 2-(3,5-dimethoxyphenyl) propan-2-yloxycarbonyl, 2,2,4,6,7,-pendamethyl-dihydrobenzofuran-5-sulfonyl, triphenylmethyl, tert-butylcarbonyl, t-butoxy, allyloxycarbonyl, methoxytrimethylbenzene sulfonyl, 4,4-dimethoxy benzhydryl, 2,2,5,7,8-pentamethylchroman-6-sulfonyl, 2,4,6-trimethoxybenzyl, allylcarbonyl, and acetamidomethyl;

Y is $NR_1$;

X is $NR_5$;

D is H, Cl, substituted or unsubstituted alkyl, substituted or unsubstituted aryl, or substituted or unsubstituted heteroaryl, $R_1$ is a radical of an amino acid wherein the amino acid is an unnatural amino acid, and $R_5$ is H, substituted or unsubstituted alkyl, substituted or unsubstituted alkoxy, substituted or unsubstituted alkoxyalkylene, optionally protected alkyl amine, or a side chain radical of an amino acid, which is substituted or unsubstituted.

7. The compound according to claim 1, A compound of the Formula (I):

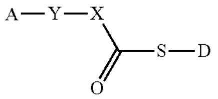

(I)

wherein

A is a protecting group selected from the group consisting of tert-butoxycarbonyl, 9-fluorenylmethoxycarbonyl, carboxybenzyl, 2-(3,5-dimethoxyphenyl) propan-2-yloxycarbonyl, 2,2,4,6,7,-pendamethyl-dihydrobenzofuran-5-sulfonyl, triphenylmethyl, tert-butylcarbonyl, t-butoxy, allyloxycarbonyl, methoxytrimethylbenzene sulfonyl, 4,4-dimethoxy benzhydryl, 2,2,5,7,8-pentamethylchroman-6-sulfonyl, 2,4,6-trimethoxybenzyl, allylcarbonyl, and acetamidomethyl;

Y is $NR_1$;

X is $NR_5$;

D is H, Cl, substituted or unsubstituted alkyl, substituted or unsubstituted aryl, or substituted or unsubstituted heteroaryl, $R_1$ is H, substituted or unsubstituted alkyl, substituted or unsubstituted alkoxy, substituted or unsubstituted alkoxyalkylene, optionally protected alkyl amine, or a side chain radical of an amino acid, which is unsubstituted or substituted; and $R_5$ is a radical of an amino acid wherein the amino acid is an unnatural amino acid.

8. The compound according to claim 1, which is of the formula:

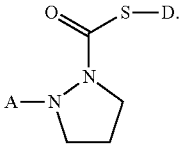

(III)

9. The compound according to claim 8, wherein A is selected from the group consisting of tert-butoxycarbonyl, 9-fluorenylmethoxycarbonyl, and carboxybenzyl.

10. The compound according to claim 1, which is of the formula:

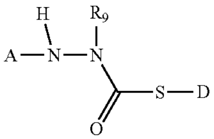

(IV)

wherein $R_9$ is H, substituted or unsubstituted alkyl, substituted or unsubstituted alkoxy, alkoxyalkylene, optionally protected alkyl amine, or a side chain radical of an amino acid, which is substituted or unsubstituted.

11. A compound of the Formula (V):

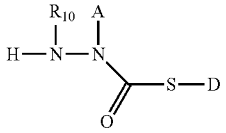

(V)

wherein

A is a protecting group selected from the group consisting of tert-butoxycarbonyl, 9-fluorenylmethoxycarbonyl, carboxybenzyl, 2-(3,5-dimethoxyphenyl) propan-2-yloxycarbonyl, 2,2,4,6,7,-pendamethyl-dihydrobenzofuran-5-sulfonyl, triphenylmethyl, tert-butylcarbonyl, t-butoxy, allyloxycarbonyl, methoxytrimethylbenzene sulfonyl, 4,4-dimethoxy benzhydryl, 2,2,5,7,8-pentamethylchroman-6-sulfonyl, 2,4,6-trimethoxybenzyl, allylcarbonyl, and acetamidomethyl;

D is H, Cl, substituted or unsubstituted alkyl, substituted or unsubstituted aryl, or substituted or unsubstituted heteroaryl; and $R_{10}$ is H, substituted or unsubstituted alkyl, substituted or unsubstituted alkoxy, substituted or unsubstituted alkoxyalkylene, optionally protected alkyl amine, or a side chain radical of an amino acid, which is substituted or unsubstituted.

12. The compound according to claim 1, wherein $R_1$ is a radical of an amino acid, wherein the amino acid is selected from the group consisting of aspartic acid, phenylalanine, alanine, histidine, glutamic acid, tryptophan, valine, leucine, lysine, methionine, tyrosine, isoleucine, arginine, glycine, asparagine, serine, and glutamine, which are unsubstituted or substituted by one or more substituents selected from the group consisting of halo, $C_1$-$C_6$ alkyl, —COOR, —COR, methoxy, ethoxy, propoxy, $C_1$-$C_6$ haloalkyl, and a protecting group, wherein R is alkyl.

13. The compound according to claim 12, wherein $R_5$ is a radical of an amino acid, wherein the amino acid is selected from the group consisting of aspartic acid, phenylalanine, alanine, histidine, glutamic acid, tryptophan, valine, leucine, lysine, methionine, tyrosine, isoleucine, arginine, glycine, asparagine, serine, and glutamine, which are unsubstituted or substituted by one or more substituents selected from the group consisting of halo, $C_1$-$C_6$ alkyl, —COOR, —COR, methoxy, ethoxy, propoxy, $C_1$-$C_6$ haloalkyl, and a protecting group, wherein R is alkyl.

14. A process for synthesizing an aza-peptide comprising activating an acyl thiol with TCCA or a combination of TCCA and TBACl to form an acyl chloride and coupling the acyl chloride with an amine, wherein the acyl thiol is a compound according to claim 1.

15. A process for preparing a compound according to claim 1, which comprises forming the compound by reacting a semi-protected hydrazine with chlorothioformate to form an S-alkylthiocarbazate, and alkylating the resulting S-alkylthiocarbazate selectively via Mitsunobu reaction, a direct alkylation with a combination of NaH or Barton's base and an alkyl halide.

16. The compound according to claim 1, wherein:

$R_1$ is H, substituted or unsubstituted alkyl, substituted or unsubstituted alkoxy, substituted or unsubstituted alkoxyalkylene, optionally protected alkyl amine, or a side chain radical of an amino acid, which is unsubstituted or substituted; and $R_5$ is substituted or unsubstituted alkyl, substituted or unsubstituted alkoxy, substituted or unsubstituted alkoxyalkylene, optionally protected alkyl amine, or a side chain radical of an amino acid, which is substituted or unsubstituted.

17. The compound according to claim 1, wherein:

$R_1$ is H, substituted or unsubstituted alkyl, or a side chain radical of an amino acid, which is unsubstituted or substituted; and $R_5$ is substituted or unsubstituted alkyl, or a side chain radical of an amino acid, which is substituted or unsubstituted.

18. The compound according to claim 1, wherein A is fluorenylmethoxycarbonyl.

19. The compound according to claim 1, wherein D is ethyl.

20. The compound according to claim 1, wherein A is fluorenylmethoxycarbonyl, and D is ethyl.

21. The compound according to claim 1, wherein A is 9-fluorenylmethoxycarbonyl, $R_1$ is H; and D is ethyl.

* * * * *